(12) United States Patent
Walther et al.

(10) Patent No.: US 9,605,283 B2
(45) Date of Patent: Mar. 28, 2017

(54) MICROORGANISM MODIFIED FOR THE PRODUCTION OF 1,3-PROPANEDIOL

(71) Applicant: INSTITUT NATIONAL DES SCIENCES APPLIQUÉES, Toulouse (FR)

(72) Inventors: Thomas Walther, Lacroix-Falgarde (FR); Jean Marie Francois, Toulouse (FR)

(73) Assignee: INSTITUT NATIONAL DES SCIENCES APPLIQUÉES, Toulouse (FR)

( * ) Notice: Subject to any disclaimer, the term of this patent is extended or adjusted under 35 U.S.C. 154(b) by 14 days.

(21) Appl. No.: 14/410,732

(22) PCT Filed: Jul. 10, 2013

(86) PCT No.: PCT/EP2013/064616
§ 371 (c)(1),
(2) Date: Dec. 23, 2014

(87) PCT Pub. No.: WO2014/009432
PCT Pub. Date: Jan. 16, 2014

(65) Prior Publication Data
US 2015/0147795 A1    May 28, 2015

Related U.S. Application Data

(60) Provisional application No. 61/670,389, filed on Jul. 11, 2012.

(51) Int. Cl.
| | | |
|---|---|---|
| C12P 7/18 | (2006.01) |
| C12N 15/78 | (2006.01) |
| C12N 9/04 | (2006.01) |
| C12N 9/02 | (2006.01) |
| C12N 9/12 | (2006.01) |
| C12N 9/88 | (2006.01) |
| C12N 15/52 | (2006.01) |

(52) U.S. Cl.
CPC ............ *C12P 7/18* (2013.01); *C12N 9/0006* (2013.01); *C12N 9/0008* (2013.01); *C12N 9/1205* (2013.01); *C12N 9/88* (2013.01); *C12N 15/52* (2013.01); *C12Y 101/01001* (2013.01); *C12Y 101/01027* (2013.01); *C12Y 101/01037* (2013.01); *C12Y 101/01202* (2013.01); *C12Y 401/01001* (2013.01); *C12Y 401/01072* (2013.01); *C12Y 401/01* (2013.01)

(58) Field of Classification Search
CPC .............. C12N 1/20; C12N 15/52; C12P 7/18
USPC ......................... 435/190, 193, 232, 252.33
See application file for complete search history.

(56) References Cited

U.S. PATENT DOCUMENTS 8,900,838 B2 * 12/2014 Soucaille ................ C12N 1/20
                                                    435/158

FOREIGN PATENT DOCUMENTS

| WO | 00/70057 A2 | 11/2000 |
| WO | 01/12833 A2 | 2/2001 |
| WO | 2012/004247 A1 | 1/2012 |
| WO | 2012/056318 A1 | 5/2012 |

OTHER PUBLICATIONS

Written Opinion—PCT/EP2013/064616 (2013).*
Nakamura C E et al: "Metabolic engineering for the microbial production of 1, 3-propanediol," Current Opinion in Biotechnology, London, GB, vol. 14, No. 5, Oct. 1, 2003 (Oct. 1, 2003), pp. 454-459.
Claudia E Vickers et al: "Examining the feasibility of bulk commodity production in *Escherichia coli*," Biotechnology Letters, Springer Netherlands, Dordrecht, vol. 34, No. 4, Dec. 10, 2011 (Dec. 10, 2011), pp. 585-596.

* cited by examiner

*Primary Examiner* — Tekchand Saidha
(74) *Attorney, Agent, or Firm* — Oliff PLC

(57) ABSTRACT

The invention relates to a modified microorganism for the production of PDO from a carbon substrate wherein the microorganism includes a three-step metabolic pathway including a first step of conversion of 2,4-dihydroxybutyrate (DHB) to obtain 2-oxo-4-hydroxybutyrate (OHB) by an enzyme having 2,4-DHB dehydrogenase activity, a second step of decarboxylation of the OHB to obtain 3-hydroxypropionaldehyde by an enzyme having 2-oxo-4-hydroxybutyrate decarboxylase activity, and a third step of reduction of the obtained 3-hydroxypropionaldehyde to obtain PDO with an enzyme having 3-hydroxypropionaldehyde reductase activity and the genes enabling the microorganism for the synthesis of DHB.

23 Claims, 4 Drawing Sheets

MICROORGANISM MODIFIED FOR THE PRODUCTION OF 1,3-PROPANEDIOL

The present invention relates to a modified microorganism capable of the production of 1,3-propanediol from a carbon substrate by the implementation of a synthetic pathway that comprises enzymes having 2,4-dihydroxybutyrate dehydrogenase, 2-oxo-4-hydroxybuturate decarboxylase, and 3-hydroxypropionaldehyde reductase activity, respectively, and which is capable of the synthesis of 2,4-dihydroxybutyrate from a carbon substrate.

BACKGROUND OF THE INVENTION 1,3-propanediol (PDO) is a chemical building block that finds its main application in the production of polyesters. PDO can also be used as a low cost biocide and as an additive in a large number of chemical products (reviewed in (Saxena, Anand, Saran, & Isar, 2009)).

PDO can be produced by chemical synthesis using acrolein, ethylene oxide, or glycerol as starting materials. However, comparatively low product yields, harsh reaction conditions, and the production of toxic waste streams hamper cost-efficient and environmentally friendly chemical production of PDO.

PDO can also be produced by microorganisms. Natural organisms such as members of the genera *Klebsiella, Citrobacter, Clostridia*, and *Enterobacter* produce PDO during the anaerobic fermentation of glycerol where PDO synthesis serves to reoxidize excess NAD(P)H molecules produced during the conversion of glycerol into the glycolytic intermediate dihydroxyacetone phosphate. The natural biosynthesis pathway of PDO consists of a vitamin B12-dependent glycerol dehydratase which converts glycerol into 3-hydroxypropionaldehyde (3-HPA), and a 1,3-propandiol oxidoreductase which converts 3-HPA into PDO. Glycerol dehydratase and PDO oxidoreductase encoding genes are commonly grouped in an operon together with genes that encode the dehydratase reactivation factor and genes encoding enzymes for glycerol assimilation (Saxena, Anand, Saran, & Isar, 2009).

Recent approaches aim at the production of PDO from glucose by using genetically engineered microorganisms and preferentially *Escherichia coli* (Emptage, Haynie, Laffend, Pucci, & Whited, 2000) (Laffend, Nagarajan, & Nakamura, 1995). *E. coli* is not naturally capable of producing PDO. This organism was equipped with enzymes that enhance both the production of glycerol (GPD1, GPP2 of *Saccharomyces cerevisiae*), and the conversion of glycerol into PDO (dhaB1-3, orfZ, orfX of *Klebsiella pneumoniae*). It was found that its natural NADP-dependent alcohol dehydrogenase, YqhD, was capable of converting 3-HPA into PDO rendering the expression of an additional PDO oxidoreductase (e.g. dhaT) optional and even somewhat less beneficial. In addition, all genes responsible for glycerol assimilation were deleted in the production strain. The attenuation of the phosphoenolpyruvate (PEP)-dependent phosphotransferase system, and the attenuation of glyceraldehyde-3-phosphate dehydrogenase activity further increased PDO yield and productivities. This technology is currently exploited by DuPont who announced productivities of 3.5 g/Lh, final product titers of 135 g/L and carbon yields of 51% (on weight basis) in 2003 (Nakamura & Whited, 2003).

One significant drawback of this technology is the use of the vitamin B12-dependent glycerol dehydratase enzyme for PDO biosynthesis which requires supplementation of the fermentation broth with expensive vitamin B12. In addition, PDO biosynthetic pathways that employ glycerol as an intermediate depend on the utilization of fermentable sugars or glycerol as the starting material. The use of alternative carbon sources such as short and medium chain organic acids alone or in co-fermentations with sugars requires significant gluconeogenic activity therefore rendering PDO synthesis inefficient and limiting the spectrum of potential raw materials. The development of PDO-yielding pathways with entry points other than glycerol can therefore strongly contribute to increase product yield on sugars, reduce production costs by avoiding vitamin B12 dependent enzymes, and/or increase metabolic flexibility to adapt PDO production organisms to a larger panel of starting materials.

Recently, a pathway was disclosed (WO2012/004247) that describes production of PDO departing from oxaloacetate, and which proceeds through the amination of oxaloacetate to yield aspartate, the transformation of aspartate into homoserine, the deamination of homoserine to yield 2-oxo-4-hydroxybutyrate (OHB), and the conversion of OHB into PDO via 2-oxo-4-hydroxybutyratedecarboxylase and 1,3-propanediol dehydrogenase. The disclosed invention employs naturally available enzymes to build up the required reaction sequence. The theoretical PDO yield on glucose for this pathway equals the yield of PDO production from glucose via glycerol. However, since this pathway employs two transamination steps this theoretical yield will only be attained if the amino group could be entirely recycled in the transamination reactions and if NADPH-consuming de novo synthesis of glutamate would not be required. This is not very likely to occur.

The present invention represents an alternative to the existing technology by producing PDO from the organic acid malate without the need of gluconeogenic activity, without the need for metabolically costly transamination reactions, and without employing vitamin B12-dependent enzymes. In particular, the invention comprises the production of PDO from 2,4-dihydroxybutyric acid (DHB) via a non-natural synthetic pathway, and the functional expression of this pathway in a host organism to zymotically produce PDO from, for example, sugars such as glucose.

GENERAL DESCRIPTION OF THE INVENTION

Accordingly, one object of the present invention is a modified microorganism for the production of PDO from a carbon substrate wherein the microorganism expresses a three step metabolic pathway comprising the following steps: a first step of conversion of 2,4-dihydroxybutyrate (DHB) to obtain 2-oxo-4-hydroxybutyrate (OHB) by an enzyme having DHB dehydrogenase activity, a second step of decarboxylation of the OHB to obtain 3-hydroxypropionaldehyde by an enzyme having 2-oxo-4-hydroxybutyrate decarboxylase activity, and a third step of reduction of the obtained 3-hydroxypropionaldehyde in PDO with an enzyme having 3-hydroxypropionaldehyde reductase activity, and the pathway enabling the microorganism to synthesize DHB.

In a preferred aspect of the invention the modified organism that expresses the pathway to convert DHB into PDO additionally expresses a pathway to convert malate into DHB comprising the following steps: a first step of conversion of malate into 4-phospho-malate by an enzyme having malate kinase activity, a second step of conversion of 4-phospho-malate into malate semialdehyde by an enzyme having malate semialdehyde dehydrogenase activity, and a third step of conversion of malate semialdehyde into DHB by an enzyme having malate semialdehyde reductase activity.

DETAILED DESCRIPTION OF THE PRESENT INVENTION

The present invention deals with a modified microorganism for the production of PDO from a carbon substrate (which is preferentially a sugar or a sugar mixture that preferentially contains glucose), wherein said microorganism comprises a three step metabolic pathway catalyzing the synthesis of PDO from DHB. As DHB is not naturally available within microorganisms, said microorganism additionally expresses a pathway for the synthesis of DHB, and preferentially a pathway for the conversion of malate into DHB.

According to the present invention, each of the three pathway steps is catalyzed by enzymes defined by their activity. Said enzymes are coded by genes defined below. Functional homologues, functional variants and functional fragments of said genes and proteins are encompassed by the definition. Enzymes with mutation(s) are also encompassed by the present definition as long as the mutated enzymes retain the enzymatic activity or have an enhanced activity.

The designation of these genes has a more general meaning according to the invention and covers the corresponding genes in other organisms.

Within the meaning of the invention, the conversion of DHB in OHB is catalyzed by an enzyme having DHB dehydrogenase activity, said enzyme may be obtained by at least one mutation of an enzyme, said mutation improving the activity and/or the substrate affinity of the mutated enzyme for DHB.

Enzymes having DHB dehydrogenase can be identified among enzymes having soluble (cytosolic) or membrane-associated lactate dehydrogenase activity. In a more specific aspect of the invention, the soluble DHB dehydrogenase activity is encoded by IdhA from *Lactococcus lactis* (SEQ ID No. 119), and the membrane associated DHB dehydrogenase activity is encoded by lldD from *E. coli* (SEQ ID No. 121).

Within another aspect of the invention, the DHB dehydrogenase activity of Ec-LldD can be improved by mutating position Val108.

Within a further aspect of the invention, the enzyme having DHB dehydrogenase activity can be obtained by mutating natural cytosolic or membrane-associated malate dehydrogenase enzymes.

According to another aspect the mutated cytosolic malate dehydrogenases are encoded by mdh from *E. coli* (SEQ ID No. 123) or mdh from *Bacillus subtilis* (SEQ ID No. 125), and carry mutations in at least one of the following positions (by reference to the mdh from *E. coli*, SEQ ID No. 124): Ile12, Arg81, Lys82, Met85, Asp86, Val93, Ile117, Gly179, Thr211, or Met227

According to another aspect the conversion of OHB in 3-HPA is catalyzed by an enzyme having 2-oxo-4-hydroxybutyrate decarboxylase activity, said enzyme may be obtained by at least one mutation of an enzyme, said mutation improving the activity and/or the substrate affinity of the mutated enzyme for OHB.

Said activity can be identified among enzymes having 2-keto acid decarboxylase activity. Genes coding for a 2-keto acid decarboxylase activity are well known in the art, including pdc genes from various species, and more particularly the PDC1, PDC5, PDC6, ARO10 and THI3 genes from *Saccharomyces cerevisiae*, kivD, or kdcA genes from *Lactococcus lactis*; pdc gene from *Clostridium acetobutylicum*; PDC2 and PDC3 genes from *Arabidopsis thaliana*; PDC1, PDC2 and ARO10 genes from *Pichia stipitis*; and the pdc gene from *Zymomonas mobilis*. The first subunit of the 2-ketoglutarate decarboxylase complex, encoded by the gene sucA from *Escherichia coli*, also possesses 2-keto acid decarboxylase activity, as well as the enzyme encoded by the gene dxs of *Escherichia coli*. Functional homologues, functional variants and functional fragments of said genes and proteins are encompassed by the definition.

According to another aspect of the invention, the OHB decarboxylase activity of above listed enzymes can be improved by mutations.

Within a further aspect of the invention, the improved OHB decarboxylase enzyme is encoded by pdc from *Z. mobilis* (SEQ ID No. 127) carrying a mutation in at least one of the following positions: Tyr290, Trp392, Gly413, or Ile476 (*Z. mobilis* numbering, SEQ ID No. 128).

Within a further aspect of the invention, the improved OHB decarboxylase enzyme is encoded by kdcA from *L. lactis* (SEQ ID No. 129) carrying a mutation in at least one of the following positions: Gln377, Phe381, Phe382, Gly402, Val461, Ile465, Met538, or Phe542 (by reference to the kdcA from *L. lactis* SEQ ID No. 130).

According to another aspect the conversion of 3-HPA in PDO is catalyzed by an enzyme having PDO dehydrogenase activity. Said activity can be identified among enzymes having hydroxylaldehyde reductase activity, alcohol dehydrogenase activity, lactaldehyde reductase activity, or methylglyoxal reductase activity, said enzyme may be obtained by at least one mutation of an enzyme, said mutation improving the activity and/or the substrate affinity of the mutated enzyme for 3-HPA.

Genes coding for an aldehyde reductase activity are well known in the art, and include the yqhD, fucO, dkgA, dkgB genes from *Escherichia coli*, the dhaT gene of *K. pneumoniae*, and the ADH1 and ADH2 genes from *Saccharomyces cerevisiae*. Functional homologues, functional variants and functional fragments of said genes and proteins are encompassed by the definition.

Proteins/nucleic acids sharing substantial homology with the above enzymes/nucleic acids are also another aspect of the invention such as functional variants or functional fragments.

The expression "substantial homology" covers homology with respect to structure and/or amino acid components and/or biological activity.

More generally, within the meaning of the invention the homology between two protein or nucleic sequences can be determined by methods well known by the skilled man in the art. It is generally defined as a percentage of sequence identity between a reference sequence and the sequence of a protein: nucleic acid of interest.

As used herein, "percent (%) sequence identity" with respect to the amino acid or nucleotide sequences identified herein is defined as the percentage of amino acid residues or nucleotides in a candidate sequence that are identical with the amino acid residues or nucleotides in an enzyme sequence, after aligning the sequences and introducing gaps, if necessary, to achieve the maximum percent sequence identity, and not considering any conservative substitutions as part of the sequence identity. Methods for performing sequence alignment and determining sequence identity are known to the skilled artisan, may be performed without undue experimentation, and calculations of identity values may be obtained with definiteness. See, for example, Ausubel, et al., eds. (1995) Current Protocols in Molecular Biology, Chapter 19 (Greene Publishing and Wiley-Interscience, New York); and the ALIGN program (Dayhoff (1978) in Atlas of Protein Sequence and Structure 5:Suppl. 3 (National Biomedical Research Foundation, Washington, D.C.). A number of algorithms are available for aligning sequences and determining sequence identity and include, for example, the homology alignment algorithm of Needleman et al. (1970) J. Mol. Biol. 48:443; the local homology algorithm of Smith, et al. (1981) Adv. Appl. Math. 2:482; the search for similarity method of Pearson, et al. (1988) Proc. Natl. Acad. Sci. 85:2444; the Smith-Waterman algorithm (Meth. Mol. Biol. 70:173-187 (1997); and BLASTP, BLASTN, and BLASTX algorithms (see Altschul, et al. (1990) J. Mol. Biol. 215:403-410). Computerized programs using these algorithms are also available, and include, but are not limited to: ALIGN or Megalign (DNASTAR) software, or WU-BLAST-2 (Altschul, et al., Meth. Enzym., 266:460-480 (1996)); or GAP, BESTFIT, BLAST (Altschul, et al.), supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can be determined by the Smith-Waterman homology search algorithm (Meth. Mol. Biol. 70:173-187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum62 amino acid substitution matrix, with a gap weight of 12 and a length weight of 2. With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for increased sequence identity associated with inclusion of gaps in the derivative's amino acid sequence can be made by assigning gap penalties.

The enzymes according to the present invention having the same activity share at least about 50%, 70% or 85% amino acid sequence identity, preferably at least about 85% amino acid sequence identity, more preferably at least about 90% amino acid sequence identity, even more preferably at least about 95% amino acid sequence identity and yet more preferably 98% amino acid sequence identity. Preferably, any amino acid substitutions are "conservative amino acid substitutions" using L-amino acids, wherein one amino acid is replaced by another biologically similar amino acid. Conservative amino acid substitutions are those that preserve the general charge, hydrophobicity/hydrophilicity, and/or steric bulk of the amino acid being substituted. Examples of conservative substitutions are those between the following groups: Gly/Ala, Val/Ile/Leu, Lys/Arg, Asn/Gln, Glu/Asp, Ser/Cys/Thr, and Phe/Trp/Tyr. A derivative may, for example, differ by as few as 1 to 10 amino acid residues, such as 6-10, as few as 5, as few as 4, 3, 2, or even 1 amino acid residue.

The term functional variant encompasses enzymes that may present substantial sequence modifications when compared to the sequences specifically described within the present application but that still retain the original enzymatic activity.

It also means that the sequence of the enzyme may comprise less amino acids than the original one but said truncated enzyme still retains the original enzymatic activity.

According to an aspect of the invention, the activity of the enzyme catalyzing the first and/or, the second and/or the third step of the method of the present invention is enhanced. This enhancement can be measured by an enzymatic assay as described in Examples 1 to 5.

Improvement of said enzymes can be obtained by at least one mutation, said mutation(s) (i) improving the activity and/or substrate affinity of the mutated enzyme for 2,4-DHB, OHB, 3-HPA respectively, and or (ii) decreasing the activity and/or substrate affinity of the mutated enzyme for their natural substrate.

Within the present invention, the expression "improve the activity and/or substrate affinity" means that the enzyme before mutation, was either unable to use the substrate, and/or synthesized the product of the reaction at a maximum specific rate at least three times lower, and/or had an affinity for 2,4-DHB, OHB or 3-HPA that was at least three times lower, and/or.

had a maximum specific activity on the natural substrate that was at least three times higher, and/or.

had an affinity for the natural substrate that was at least three times higher.

Any metabolic pathway catalyzing the synthesis of DHB from a carbon substrate is encompassed by the present invention. The synthesis of DHB from malate constitutes a preferred aspect of the invention.

In a specific aspect of the invention the DHB is synthesized by a three step pathway starting from malate such as described in the patent application published under WO 2012/056318 wherein:

The conversion of malate into 4-phospho-malate is catalyzed by an enzyme having malate kinase activity. Said malate kinase activity can be identified among enzymes having aspartate kinase activity or homoserine kinase activity. Said malate kinase activity can be obtained by mutation of a natural amino acid kinase, for example the *E coli* aspartate kinase mutant LysC E119G or *E. coli* aspartate kinase mutant LysC E119G E250K.

The conversion of phospho-malate into malate-4-semialdehyde is catalyzed an enzyme which possesses malate semialdehyde dehydrogenase activity. Said malate semialdehyde dehydrogenase activity can be identified among enzymes having aspartate semialdehyde dehydrogenase activity. Said malate semialdehyde dehydrogenase activity can be obtained by mutation of a natural amino acid dehydrogenase, for example the *E coli* aspartate semialdehyde dehydrogenase mutant Asd E241Q.

The conversion of malate-4-semialdehyde into DHB is catalysed by the action of an enzyme which possesses malate-4-semialdehyde reductase activity. Said malate-4-semialdehyde reductase activity can be identified among enzyme having succinic semialdehyde reductase (SSR)

activity, such as the malate-4-semialdehyde reductase encoded by *Metallosphaera sedula* ssr gene or the mutant *M. sedula* SSR H39R N43H.

In accordance with this invention, a "nucleic acid sequence" refers to a DNA or RNA molecule in single or double stranded form, preferably a DNA molecule. An "isolated DNA", as used herein, refers to a DNA which is not naturally-occurring or no longer in the natural environment wherein it was originally present, e.g., a DNA coding sequence associated with other regulatory elements in a chimeric gene, a DNA transferred into another host cell, or an artificial, synthetically-made DNA sequence having a different nucleotide sequence compared to any naturally-occurring DNA sequence.

The present invention also relates to a chimeric gene comprising, functionally linked to one another, at least one promoter which is functional in a host organism, a polynucleotide encoding anyone of the enzymes of the invention, and a terminator element that is functional in the same host organism. The various elements which a chimeric gene may contain are, firstly, elements regulating transcription, translation and maturation of proteins, such as a promoter, a sequence encoding a signal peptide or a transit peptide, or a terminator element constituting a polyadenylation signal and, secondly, a polynucleotide encoding a protein. The expression "functionally linked to one another" means that said elements of the chimeric gene are linked to one another in such a way that the function of one of these elements is affected by that of another. By way of example, a promoter is functionally linked to a coding sequence when it is capable of affecting the expression of said coding sequence. The construction of the chimeric gene according to the invention and the assembly of its various elements can be carried out using techniques well known to those skilled in the art, in particular those described in [18]. The choice of the regulatory elements constituting the chimeric gene depends essentially on the host organism in which they must function, and those skilled in the art are capable of selecting regulatory elements which are functional in a given host organism. The term "functional" is intended to mean capable of functioning in a given host organism.

The promoters which the chimeric gene according to the invention may contain are either constitutive or inducible. By way of example, the promoters used for expression in bacteria may be chosen from the promoters mentioned below. For expression in *Escherichia coli* mention may be made of the lac, trp, lpp, phoA, recA, araBAD, prou, cst-I, tetA, cadA, nar, tac, trc, lpp-lac, Psyn, cspA, PL, PL-9G-50, PR-PL, T7, [lambda]PL-PT7, T3-lac, T5-lac, T4 gene 32, nprM-lac, VHb and the protein A promoters [19]; [20]) or else the Ptrp promoter (WO 99/64607). For expression in Gram-positive bacteria such as *Corynebacteria* or *Streptomyces*, mention may be made of the PtipA [21] or PS1 and PS2 (FR91/09870) promoters or those described in application EP0629699A2. For expression in yeasts and fungi, mention may be made of the *K. lactis* PLAC4 promoters [22] or the *K. lactis* Ppgk promoter (patent application FR 91/05294), the *Trichoderma reesei* tef1 or cbh1 promoter (WO 94/04673), the *Penicillium funiculosumhis*, csl or apf promoter (WO 00/68401) and the *Aspergillus niger* gla promoter [23].

According to the invention, the chimeric gene may also comprise other regulatory sequences, which are located between the promoter and the coding sequence, such as transcription activators (enhancers).

As such, the chimeric gene of the invention comprises in a specific embodiment at least, in the direction of transcription, functionally linked, a promoter regulatory sequence which is functional in a host organism, a nucleic acid sequence encoding enzymes of the invention and a terminator regulatory sequence which is functional in said host organism The present invention also relates to a cloning and/or expression vector comprising a chimeric gene according to the invention or a nucleic acid sequence of the invention. The vector according to the invention is of use for transforming a host organism and expressing in this organism anyone of the enzymes for the biosynthesis of PDO. This vector may be a plasmid, a cosmid, a bacteriophage or a virus. Preferentially, the transformation vector according to the invention is a plasmid. Generally, the main qualities of this vector should be an ability to maintain itself and to self-replicate in the cells of the host organism, in particular by virtue of the presence of an origin of replication, and to express anyone of the enzymes therein. For the purpose of stable transformation of a host organism, the vector may also integrate into the genome. The choice of such a vector, and also the techniques of insertion of the chimeric gene according to the invention into this vector, are thoroughly described in [18] and are part of the general knowledge of those skilled in the art. Advantageously, the vector used in the present invention also contains, in addition to the chimeric gene according to the invention, a chimeric gene encoding a selectable marker. This selectable marker makes it possible to select the host organisms which are effectively transformed, i.e. those which incorporated the vector. According to a particular embodiment of the invention, the host organism to be transformed is a bacterium, a yeast, a fungus. Among the selectable markers which can be used, mention may be made of markers containing genes for resistance to antibiotics, such as, for example, the hygromycinphosphotransferase gene [24]; [25]. Other markers may be genes to complement an auxotrophy, such as the pyrA, pyrB, pyrG, pyr4 [26], arg4, argB [27] and trpC [28] genes, the molybdopterin synthase gene[29] [30] or that of acetamidase [31]. Mention may also be made of genes encoding readily identifiable enzymes such as the GUS enzyme, or genes encoding pigments or enzymes regulating the production of pigments in the transformed cells. Such selectable marker genes are in particular described in patent applications WO 91/02071, WO 95/06128, WO 96/38567 and WO 97/04103.

The present invention also relates to transformed host organisms containing at least one chimeric gene according to the invention, either integrated into their genome or carried on an extrachromosomal genetic element, for example a plasmid. In a more specific aspect of the invention, the transformed host organism comprises a nucleic acid of the invention or a chimeric gene comprising a nucleic acid or an expression vector comprising a nucleic acid encoding a malate kinase and/or, a malate semialdehyde dehydrogenase, and/or a malate semialdehyde reductase, and/or a DHB dehydrogenase, and/or a OHB decarboxylase and/or a 3-PHA reductase.

The term "host organism" is intended to mean any lower monocellular organism into which the chimeric gene(s), nucleic acid(s) or vector(s) according to the invention may be introduced in order to produce PDO. Preferably, the host organism is a microorganism, in particular a bacterium, preferentially selected among Enterobacteriaceae, Clostridiaceae, Bacillaceae, Streptomycetaceae, Streptococcaceae, Methylobacteriacae, and Corynebacteriaceae, most preferentially *Escherichia coli, Bacillus subtilis, Corynebacterium glutamicum, Clostridium acetobutylicum, Methylobacterium extorquens*, or *Lactococcus lactis*, or a yeast preferentially selected among Saccharomycetaceae, Pichiaceae, and Schizosaccharomycetaceae, most preferentially *Saccharomyces cerevisiae, Schizosaccharomyces pombe, Kluyveromyces lactis, Kluyveromyces marxianus, Pichia jadinii, Pichia stipitis*, or *Pichia pastoris* or a fungus, for example of the *Penicillium, Aspergillus* and more particularly *Aspergillus flavus, Chrysosporium* or *Trichoderma* genus or a baculovirus.

The host organism can be a host organism that naturally overproduces malate or succinate from sugars such as glucose or a host organism that was engineered to overproduce malate or succinate from sugars such as glucose and in which all potential membrane transporters that facilitate export of organic acids, such as malate, pyruvate, succinate, and fumarate have been deleted. The host organism can be an organism that was engineered to overproduce DHB and in which all membrane transporters that facilitate export of organic acids such as DHB, malate, pyruvate, succinate, and fumarate have been deleted. Examples of permeases that facilitate export of malate and other organic acids are Mae1 from *Schizosaccharomyces pombe* (Camarasa et al., 2001; Grobler et al., 1995), DctA from *Bacillus subtilis* (Groeneveld et al., 2010), Dct 1-4 from *E. coli*, Jen1 from *S. cerevisiae* (Akita et al., 2000). For an expert it will be possible to identify candidate permeases in other microorganisms based on sequence homology. These constructions will serve to keep DHB, malate and other organic acids inside the cell to make them available for PDO production.

To obtain the host organisms according to the invention, those skilled in the art may use one of the many known transformation methods.

One of these methods consists in bringing the cells of the host organisms to be transformed into contact with polyethylene glycol (PEG) and with the vectors according to the invention. Electroporation is another method, which consists in subjecting the cells to be transformed and the vectors of the invention to an electric field. Another method consists in directly injecting the vectors into the cells or the tissues by microinjection. The "biolistic" method may be used. It consists in bombarding cells or tissues with particles onto which the vectors of the invention are adsorbed (U.S. Pat. No. 4,945,050).

Several methods for transforming bacteria are described in the literature for *Escherichia coli* and other Gram-negative bacteria. Conjugation may also be used. For Gram-positive bacteria, electroporation may be used, and also protoplast transformation, in particular for bacteria of the *Streptomyces* genus.

Several methods for transforming fungi are also described in the literature. Protoplast transformation with PEG is described for *Aspergillus* in EP 0260762, and an adaptation of this method to the species *Penicillium funiculosum* is described in WO 00/36120. Transformation by restriction enzyme mediated integration, or REMI, is also known, as is protoplast transformation using bacteria of the *Agrobacterium* genus. Techniques for transforming yeasts are also described in the literature, In a further aspect, the invention deals with a method of production of PDO comprising the steps of contacting the modified microorganism with a carbon substrate in an appropriate culture medium, and recovering PDO from the culture medium.

In a more preferred aspect of the invention the carbon substrate is a sugar or a sugar mixture.

In a more preferred aspect of the invention, the PDO is further purified.

The following examples illustrate the invention. These examples are for purposes of illustration only and are not to be construed as limiting the scope of the invention in any manner.

EXAMPLES

Example 1

Demonstration of 2,4-dihydroxybutyrate Dehydrogenase Activity

Figure 1:
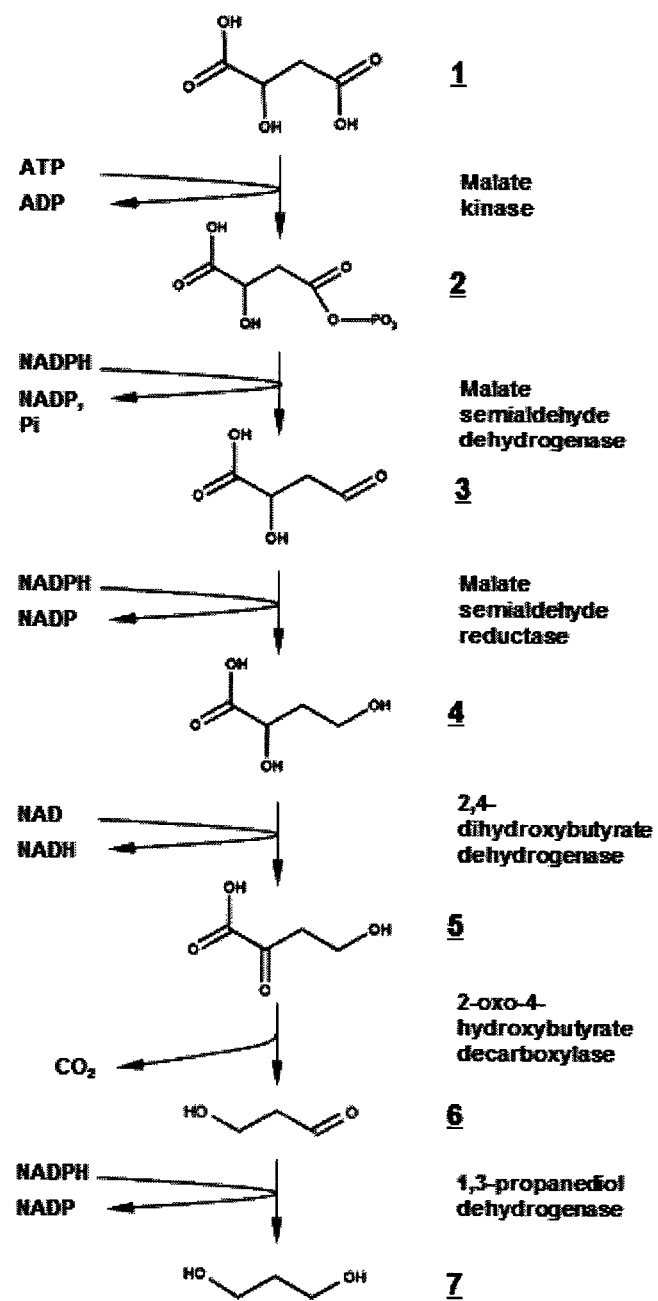
FIG. 1: Schematic representation of the synthetic 1,3-propanediol-yielding pathway. 1—malate, 2—malyl-4-phosphate, 3—malate-4-semialdehyde, 4—2,4-dihydroxybutyrate, 5—2-oxo-4-hydroxybutyrate, 6—3-hydroxypropionaldehyde, 7—1,3-propanediol.

Construction of Plasmids Containing Wild-Type Genes Coding for Candidate DHB Dehydrogenase Enzymes:

The genes coding for (L)-lactate dehydrogenase of *Lactococcus lactis*, ldhA, (L)-malate dehydrogenase of *Escherichia coli*, mdh, (L)-malate dehydrogenase of *Bacillus subtilis*, mdh, and for the membrane associated (L)-lactate dehydrogenase of *E. coli*, lldD, were amplified by PCR using the high-fidelity polymerase Phusion™ (Fermentas) and the primers listed in Table 1. Genomic DNAs of *E. coli* MG1655, *L. Lactis* IL1403, and *B. subtilis* strain 168 were used as the template. The primers introduced restriction sites (Table 1) upstream of the start codon and downstream of the stop codon, respectively, facilitating the ligation of the digested PCR products into the corresponding sites of the pET28a+ (Novagen) expression vector using T4 DNA ligase (Fermentas). Ligation products were transformed into *E. coli* DH5α cells. The resulting pET28-Ec-mdh, pET28-Ll-ldh, pET28-Bs-mdh, and pET28-Ec-lldD plasmids were isolated and shown by DNA sequencing to contain the correct full-length sequence of the *E. coli* mdh (SEQ ID No. 123), *L. lactis* ldhA (SEQ ID No. 119), *B. subtilis* mdh (SEQ ID No. 125), and *E. coli* lldD (SEQ ID No. 121) genes, respectively. The corresponding protein sequences are represented by SEQ ID No. 124, SEQ ID No. 120, SEQ ID No. 126 and SEQ ID No. 122, respectively.

TABLE 1

Primer sequences and restriction sites used for amplification and cloning of candidate enzymes

| Gene | Forward and reverse primer sequence 5'-3' | Restriction sites |
|---|---|---|
| Ec-mdh | TATAATCATATGAAAGTCGCAGTCCTC (SEQ ID No. 131) | NdeI |
| | TATAATGGATCCTTACTTATTAACGAA CTC (SEQ ID No. 132) | BamHI |
| Ll-ldhA | TATAATCATATGGCTGATAAACAACGT AAAAAA (SEQ ID No. 133) | NdeI |
| | TATAATGGATCCTTAGTTTTTAACTGC AGAAGCAAA (SEQ ID No. 134) | BamHI |
| Bs_mdh | CATATGGGAAATACTCGTAAAAAAGTT (SEQ ID No. 135) | Nde1 |
| | GGATCCTTAGGATAATACTTTCATGAC (SEQ ID No. 136) | BamH1 |
| Ec-lldD | CATATGATTATTTCCGCAGCCAGC (SEQ ID No. 137) | Nde1 |
| | AGATCTCTATGCCGCATTCCCTTTC (SEQ ID No. 138) | BgI2 |

Expression of Enzymes:

E. coli BL21 (DE3) star cells were transformed with the appropriate plasmids using standard genetic protocols (Sambrook, Fritsch, & Maniatis, 1989). Enzymes with an N-terminal hexa-His tag were expressed in 50 mL LB cultures that were inoculated from an overnight culture at $OD_{600}$ of 0.1 and grown to $OD_{600}$ of 0.6 before protein expression was induced by addition of 1 mM isopropyl β-D-1-thiogalactopyranoside (IPTG) to the culture medium. After 3 h of protein expression, cells were harvested by centrifugation at 4000 g at 4° C. for 10 min and discarding the supernatant. Cell pellets were stored at 20° C. until further analysis. Growth and protein expression were carried out at 37° C. Culture media contained 50 μg/mL kanamycin.

Purification of Enzymes:

Frozen cell pellets of expression cultures were resuspended in 0.5 mL of breakage buffer (50 mM Hepes, 300 mM NaCl, pH 7.5) and broken open by four successive rounds of sonication (sonication interval: 20 s, power output: 30%, sonicator: Bioblock Scientific, VibraCell™ 72437). Cell debris was removed by centrifuging the crude extracts for 15 min at 4° C. at 4000 g and retaining the clear supernatant. RNA and DNA were removed from the extracts by adding 15 mg/mL streptomycin sulfate (Sigma), centrifuging the samples at 13000 g for 10 min at 4° C. and retaining the supernatant. Clear protein extract was incubated for 1 h at 4° C. with 0.75 mL (bed volume) of Talon™ Cobalt affinity resin (Clontech). The suspension was centrifuged at 700 g in a table top centrifuge and supernatant was removed. The resin was washed with 10 bed volumes of wash buffer (50 mM Hepes, 300 mM NaCl, 15 mM Imidazole, pH 7.5) before proteins were eluted with 0.5 mL of elution buffer (50 mM Hepes, 300 mM NaCl, 250 mM Imidazole, pH 7.5). Purity of eluted enzymes was verified by SDS-PAGE analysis. Protein concentrations were estimated with the method of Bradford (Sambrook, Fritsch, & Maniatis, 1989). To stabilize the lactate dehydrogenase of L. lactis, the elution buffer was systematically exchanged by 100 mM phosphate buffer adjusted to pH 7. The protein sample was transferred to an Amicon™ Ultra centrifugal filter (cut-off 10 kDa), and centrifuged during 8 min at 4000 g at 4° C. to remove the buffer. The protein was re-diluted into phosphate buffer and the procedure was repeated 4 times.

Enzymatic Assay:

Activity of the cytosolic DHB dehydrogenases (Ec-Mdh, Bs-Mdh, Ll-LdhA) was assayed by following the DHB-dependent reduction of $NAD^+$.

(L)-2,4-dihydroxybutyrate+$NAD^+$→2-oxo-4-hydroxybutyrate+NADH     Reaction Scheme 1:

The reaction mixture contained 60 mM Hepes (pH 8), 50 mM potassium chloride, 5 mM $MgCl_2$, 10 mM NAD, (optionally, 5 mM fructose-1,6-bisphosphate (F16bP)) (all products from Sigma), and appropriate amounts of purified enzyme or cell extract. Reactions were started by adding 50 mM (L)-2,4-dihydroxybutyrate (Rhodia).

Activity of the membrane-associated DHB dehydrogenase (Ec-LldD) was assayed by following the DHB-dependent reduction of 2,6-dichloroindophenol (DCIP).

(L)-2,4-dihydroxybutyrate+$DCIP_{ox}$→2-oxo-4-hydroxybutyrate+$DCIP_{red}$     Reaction scheme 2:

The reaction mixture contained 60 mM Hepes (pH 7), 50 mM potassium chloride, 5 mM $MgCl_2$, 0.06 mM DCIP (all products from Sigma), and appropriate amounts of purified enzyme or cell extract. Reactions were started by adding 20 mM (L)-2,4-dihydroxybutyrate (Rhodia).

All enzymatic assays were carried out at 37° C. in 96-well flat bottomed microtiter plates in a final volume of 250 μL. The reactions were followed by the characteristic absorption of NADH at 340 nm ($\epsilon_{NADH}$=6.22 $mM^{-1}$ $cm^{-1}$) or the absorbtion of DCIP at 655 nm ($\epsilon_{DCIP}$=5.9 $mM^{-1}$ $cm^{-1}$) in a microplate reader (BioRad 680XR).

Results:

The results of the enzymatic measurements are summarized in Table 2. It was shown that Ec-Mdh and Bs-Mdh have no measurable DHB dehydrogenase activity. Both the cytosolic and membrane-associated lactate dehydrogenases Ll-LdhA and Ec-LldD, respectively, have DHB dehydrogenase activity.

TABLE 2

Summary of kinetic parameters of selected candidate enzymes on their natural substrate and DHB

| | Max. specific activity [μmol/(mg min)] | | Substrate affinity, Km [mM] | |
|---|---|---|---|---|
| Enzyme | Natural substrate[a] | DHB[b] | Natural substrate[a] | DHB |
| Ec-Mdh | 52.5 | 0 | 0.56 | nd |
| Bs-Mdh | 10.5 | 0 | 2.6 | nd |
| Ll-LdhA | 8.8 | 1 | 21.2 | ns |
| Ec-LldD | 6.22 | 0.37 | 0.13 | 1.31 |

[a]Natural substrates for malate dehydrogenases and lactate dehydrogenases are (L)-malate and (L)-lactate, respectively
[b]When enzymes could not be saturated, maximum specific activity refers to the activity estimated at 50 mM substrate concentration
ns—not saturated
nd—not determined Example 2

Construction of Malate Dehydrogenase Enzymes with Improved DHB Dehydrogenase Activity Site-directed mutagenesis of the E. coli mdh and the B. subtilis mdh genes were carried out using the oligonucleotide pairs listed in Table 3 and the pET28-Ec-mdh and the pET28-Bs-mdh plasmids as the templates. Point mutations to change the amino acid sequence were introduced by PCR (Phusion 1U, HF buffer 20% (v/v), dNTPs 0.2 mM, direct and reverse primers 0.04 μM each, template plasmid 50 ng, water) using the oligonucleotide pairs listed in Table 3. Mutated genes contained a new restriction site listed in Table 3 (introduced using silent mutations) in addition to the functional mutation to facilitate identification of mutated clones. The PCR products were digested by DpnI at 37° C. for 1 h to remove template DNA, and transformed into competent E. coli DH5-alpha cells (NEB). The mutated plasmids were identified by restriction site analysis and verified to carry the desired mutations by DNA sequencing.

TABLE 3

Oligonucleotides used to mutate malate dehydrogenase mdh from E. coli and mdh from B. subtilis. (nnk denotes a degenerated codon with k representing either thymine or cytosine)

| Protein | Mutation | Primer sequences 5'-3' | Restr. site |
|---|---|---|---|
| Bs-Mdh | R87A | TTACAGCCGGTATCGCAGCAAA ACCCGGGATGAGCAGAGAT (SEQ ID No. 139) ATCTCTGCTCATCCCGGGTTTT GCTGCGATACCGGCTGTAA (SEQ ID No. 140) | SmaI |
| Ec-Mdh | R81nnk | TTATCTCTGCAGGCGTAGCGNN KAAACCCGGGATGGATCGTTC (SEQ ID No. 141) GAACGATCCATCCCGGGTTTMN NCGCTACGCCTGCAGAGATAA (SEQ ID No. 142) | SmaI |
| Ec-Mdh | R81AM85E | TTATCTCTGCAGGCGTAGCGGC TAAACCGGGTGAGGATCGTTCC GACCTG (SEQ ID No. 143) CAGGTCGGAACGATCCTCACCC GGTTTAGCCGCTACGCCTGCAG AGATAA (SEQ ID No. 144) | no SmaI |
| Ec-Mdh | R81AM85Q | TTATCTCTGCAGGCGTAGCGGC TAAACCGGGTCAGGATCGTTCC GACCTG (SEQ ID No. 145) CAGGTCGGAACGATCCTGACCC GGTTTAGCCGCTACGCCTGCAG AGATAA (SEQ ID No. 146). | no SmaI |
| Ec-Mdh | I12V | GTCGCAGTCCTCGGCGCCGCTG GCGGTGTCGGCCAGGCGCTTGC AC (SEQ ID No. 147) GTGCAAGCGCCTGGCCGACACC GCCAGCGGCGCCGAGGACTGCG AC (SEQ ID No. 148) | NarI |
| Ec-Mdh | G179D | CCG GTT ATT GGC GGC CAC TCT GAT GTT ACC ATT CTG CCG CTG CTG (SEQ ID No. 149) CAGCAGCGGCAGAATGGTAACAT CAGAGTGGCCGCCAATAACCGG (SEQ ID No. 150) | EaeI |
| Ec-Mdh | R81AD86S | GGCGTAGCGGCTAAACCGGGTAT GTCTCGTTCCGACCTG (SEQ ID No. 151) CAGGTCGGAACGAGACATACCCG GTTTAGCCGCTACGCC (SEQ ID No. 152) | no SmaI |

Mutant enzymes were expressed, purified and tested for DHB dehydrogenase activity as described in Example 1.

Figure 2:
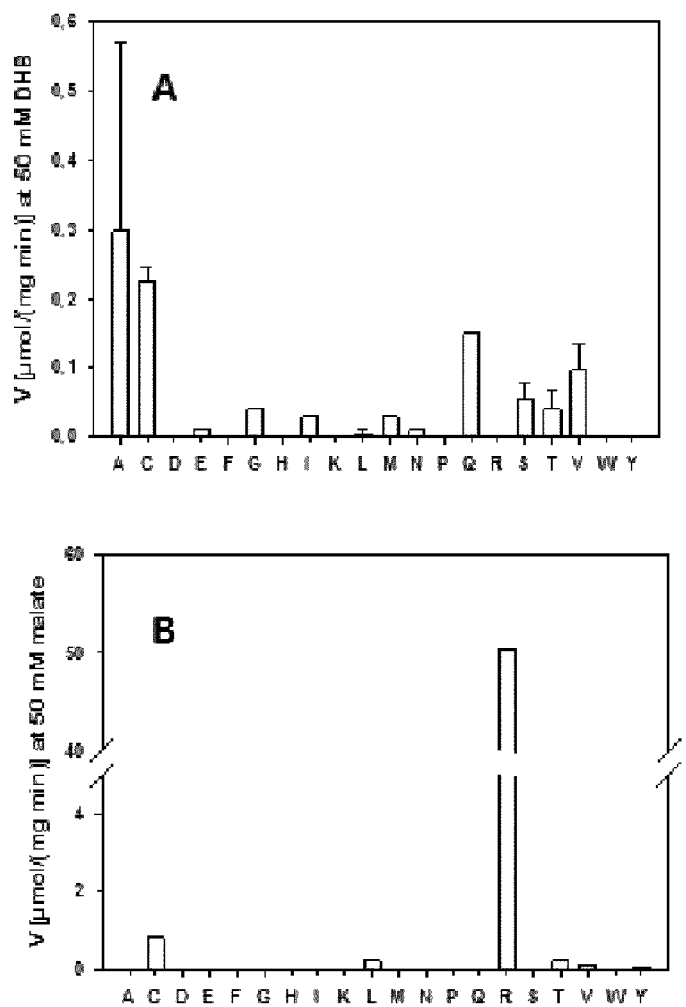
FIG. 2: Specific activities of purified *E. coli* malate dehydrogenase, Ec-Mdh, mutated in position R81. (A) Specific activities on DHB, (B) specific activities on malate. Activities were measured at a substrate concentration of 50 mM DHB or 50 mM malate.

The activities on DHB and malate obtained upon mutating Arg81 in Ec-Mdh are summarized in FIG. 2. The results demonstrate that replacement of Arg81 by alanine, cysteine, glycine, isoleucine, methionine, asparagine, glutamine, serine, threonine, or valine confer significant DHB dehydrogenase activity, and concomitant decrease of malate dehydrogenase activity. Introduction of mutation R87C into Bs-Mdh (by reference to SEQ ID No. 126) increased the maximum activity of this mutant on DHB from 0 to 0.06 μmol/(mg min) and decreased its activity on malate from 10.9 to 0.13 μmol/(mg min).

The mutation R81A in Ec-Mdh (by reference to SEQ ID No. 124) was combined with additional changes in the protein sequence. The results are listed in Table 4. It can be demonstrated that the introduction of mutation M85Q, M85E, I12V, G179D, and/or D86S in addition to mutation R81A results in a further increased activity on DHB.

TABLE 4

Summary of kinetic parameters of malate dehydrogenase mutants from E. coli and B. subtilis on malate and DHB

| Mutant | | Max. specific activity [μmol/(mg min)] | | Km [mM] | |
|---|---|---|---|---|---|
| Enzyme | Seq ID | malate[a] | DHB[b] | malate | DHB |
| Bs-MdhR87C | SEQ ID No. 154 | 0.13 | 0.06 | 6.8 | 5.4 |
| Ec-MdhR81A | SEQ ID No. 156 | 0.12 | 0.3 | 0.7 | 33 |
| Ec-MdhR81A M85Q | SEQ ID No. 158 | 0.57 | 2.98 | 2.2 | 29 |
| Ec-MdhR81A M85E | SEQ ID No 160 | 0.65 | 2.38 | 8.6 | 48 |
| Ec-MdhR81A I12V | SEQ ID No. 162 | 0.66 | 2.5 | 8.5 | ns |
| Ec-MdhR81A M85Q I12V | SEQ ID No. 164 | 0.98 | 7.1 | 12.5 | 19 |
| Ec-MdhR81A M85E I12V | SEQ ID No. 166 | 0.91 | 10.3 | 11.2 | 20 |
| Ec-MdhR81A G179D | SEQ ID No. 168 | 0.52 | 2.1 | nd | ns |
| Ec-MdhR81A D86S | SEQ ID No. 170 | 0.42 | 0.79 | 10.3 | 28 |
| Ec-MdhR81A D86S G179D | SEQ ID No 172 | 0.64 | 2.51 | 4 | 25 |

[a]activity was measured at 50 mM malate
[b]activity was measured at 50 mM DHB
ns—not saturated at concentrations of up to 100 mM Example 3

Construction of (L)-Lactate Dehydrogenase Enzymes with Improved DHB Dehydrogenase Activity Site-directed mutagenesis of the E. coli lldD gene was carried out using the oligonucleotide pairs listed in Table 5 and the pET28-Ec-lldD plasmid as the template.

Table 5

Oligonucleotides used to mutate (L)-lactatedehydrogenase lldD from E. coli.

| Protein | Mutation | Primer sequences 5'-3' | Restriction site |
|---|---|---|---|
| Ec-LldD | V108C | TTCCGTTTACTCTGTC GACGTGTTCCGTTTGC | HincII |

Table 5-continued

Oligonucleotides used to mutate
(L)-lactatedehydrogenase
lldD from E. coli.

| Protein | Mutation | Primer sequences 5'-3' | Restriction site |
|---|---|---|---|
| | | CCGA (SEQ ID NO. 173) TCGGGCAAACGGAACC CGTCGACAGAGTAAAC GGAA (SEQ ID NO. 174) | |

Mutant enzymes were expressed, purified and tested for DHB dehydrogenase and lactate dehydrogenase activity as described in Example 1. The results of the enzymatic measurements are summarized in Table 6. It was demonstrated that replacement of Val108 by cysteine changes the specificity of the enzyme in favour of DHB.

TABLE 6

Summary of kinetic parameters of E. coli lactate dehydrogenase, LldD, mutants on lactate and DHB

| Mutant | | Max. specific activity [µmol/(mg min)] | | Km [mM] | | |
|---|---|---|---|---|---|---|
| Enzyme | Seq ID | lactate | DHB | lactate | DHB | Specificity[a] |
| Wild-type | SEQ ID No. 122 | 6.22 | 0.37 | 0.13 | 1.31 | 0.006 |
| V108C | SEQ ID No. 174 | 0.55 | 0.24 | 0.42 | 0.85 | 0.21 |

[a]Specificity is expressed as $(Vmax/Km)_{DHB}/(Vmax/Km)_{nat.\ substrate}$

Example 4

Demonstration of 2-Oxo-4-Hydroxybutyrate Decarboxylase Activity

The branched-chain alpha-ketoacid decarboxylase encoding gene Ll-kdcA from L. lactis B1157-NIZO was codon-optimized for expression in E. coli. The whole optimized coding sequence flanked with NheI and EcoRI restriction sites upstream of the start codon and downstream of the stop codon respectively was synthesized by Eurofins MWG and cloned into the corresponding sites of pET28a+ (Novagen) in frame with a N-terminal hexa-His tag. The resulting pET28-Ll-kdcA plasmid was shown by DNA sequencing to have the correct sequence.

The pyruvate decarboxylases of Saccharomyces cerevisiae, Sc-PDC1 and of Zymomonas mobilis, Zm-PDC, were amplified by PCR using the high-fidelity polymerase Phusion™ (Fermentas) and the primers listed in Table 7. Genomic DNAs of S. cerevisiae BY4741, and Z. mobilis (Lindner) Kluyver and van Niel (ATCC® 31821) were used as the template. The primers introduced restriction sites (Table 7) upstream of the start codon and downstream of the stop codon, respectively, facilitating the ligation of the digested PCR products into the corresponding sites of the pET28a+ (Novagen) expression vector using T4 DNA ligase (Fermentas). Ligation products were transformed into competent E. coli DH5α cells (NEB). The resulting pET28-Sc-pdc1, and pET28-Zm-pdc plasmids were isolated and shown by DNA sequencing to contain the correct full-length sequence of the S. cerevisiae PDC1, and Z. mobilis PDC genes, respectively. The corresponding protein sequences are represented by SEQ No. 208 and SEQ ID No. 208 128 respectively.

TABLE 7

Primer sequences and restriction sites used for amplification and cloning of candidate enzymes

| Gene | Forward and reverse primer sequence 5'-3' | Restriction sites |
|---|---|---|
| Sc-PDC1 | CATATGTCTGAAATTACTTTG GGTAA (SEQ ID No. 175) | Nde1 |
| | GGATCCTTATTGCTTAGCGTT GGT (SEQ ID No. 176) | BamH1 |
| Zm-PDC | CATATGAGTTATACTGTCGGT ACC (SEQ ID No. 177) | Nde1 |
| | GGATCCCTAGAGGAGCTTGTT AAC (SEQ ID No. 178) | BamH1 |

The plasmids were used to transform E. coli BL21 (DE3) star cells and the enzymes carrying an N-terminal hexa-His tag were expressed and purified as described in Example 1. Decarboxylase activity on 2-oxo-4-hydroxybutyrate (OHB), pyruvate (Sigma), and 4-methyl-2-oxovaleric acid (Sigma) was quantified.

Enzymatic Assays:

OHB decarboxylase activity was assayed by coupling the decarboxylase activity to the NADPH-dependent reduction of the released 3-hydroxypropanal by purified aldehyde reductase, YqhD, from E. coli. The decarboxylation of pyruvate was coupled to the NADH-dependent reduction of acetaldehyde catalysed by yeast alcohol dehydrogenase. Branched-chain alpha-ketoacid decarboxylase activity was measured on 4-methyl-2-oxovaleric acid by coupling to the NADH-dependent reduction of 3-methylbutanal catalysed by horse liver alcohol dehydrogenase. The reaction mixtures contained 60 mM Hepes (pH 7), 50 mM potassium chloride, 2 mM $MgCl_2$, 0.25 mM NAD(P)H, (all products from Sigma), 0.5 mM thiamine pyrophosphate, 10 Unit/mL purified E. coli YqhD, or horse liver alcohol dehydrogenase (Sigma), or yeast alcohol dehydrogenase (Sigma), and appropriate amounts of purified enzyme or cell extract. Reactions were started by adding 20 mM 2-oxo-4-hydroxybutyrate (OHB), 10 mM 4-methyl-2-oxovaleric acid (MOV), or 5 mM pyruvate. Enzymatic assays were carried out at 37° C. in 96-well flat bottomed microtiter plates in a final volume of 250 µL. The reactions were followed by the characteristic absorption of NAD(P)H at 340 nm ($\epsilon_{NAD(P)H}$=6.22 $mM^{-1}$ $cm^{-1}$) in a microplate reader (BioRad 680XR).

Results:

The results of the decarboxylase assays are summarized in Table 8. It was demonstrated that the enzymes KdcA from L. lactis and the pyruvate decarboxylases Sc-Pdc1 and Zm-Pdc have significant OHB decarboxylase activity.

TABLE 8

Summary of kinetic parameters of selected candidate enzymes on their natural substrate and OHB

| | Max. specific activity [µmol/(mg min)] | | Substrate affinity, Km [mM] | |
|---|---|---|---|---|
| Enzyme | Natural substrate[a] | OHB[b] | Natural substrate[a] | OHB |
| Ll-KdcA SEQ ID No. 130 | 4 | 0.08 | 0.15 | 4 |

TABLE 8-continued

Summary of kinetic parameters of selected candidate enzymes on their natural substrate and OHB

| Enzyme | Max. specific activity [μmol/(mg min)] | | Substrate affinity, Km [mM] | |
|---|---|---|---|---|
| | Natural substrate[a] | OHB[b] | Natural substrate[a] | OHB |
| Zm-Pdc SEQ ID No .128 | 65 | 0.052 | 2.5 | 1.5 |
| Sc-Pdc1 SEQ ID No. 208 | 1.3 | 0.055 | nd | nd |

[a]Natural substrates for KdcA and pyruvate decarboxylases are 4-methyl-2-oxovaleric and pyruvate, respectively
[b]When enzymes could not be saturated, maximum specific activity refers to the activity estimated at 20 mM substrate concentration
ns—not saturated
nd—not determined Example 5

Construction of Enzymes with Improved OHB Decarboxylase Activity

Site-directed mutagenesis of the *L. lactis* kdcA and the *Z. mobilis* Pdc genes was carried out using the oligonucleotide pairs listed in Table 9 and the pET28-Ll-kdcA and pET28-Zm-Pdc plasmids, respectively, as the template.

TABLE 9

Oligonucleotides used to mutate branched chain 2-oxoacid decarboxylase, kdcA, from *L. lactis* and pyruvate decarboxylase, PDC, from *Z. mobilis*

| Protein | Mutation | Primer sequences 5'-3' | Restr. site |
|---|---|---|---|
| Zm-Pdc. | W392Q | GTTATTGCTGAAACCGGTGACT CTCAGTTCAATGCGCAGCGCAT GAAGC (SEQ ID NO. 179) GCTTCATGCGCTGCGCATTGAA CTGAGAGTCACCGGTTTCAGCA ATAAC (SEQ ID NO. 180) | FSP1 |
| Zm-Pdc | W392L | ACGGTTATTGCTGAAACCGGTG ACTCTTTATTCAATGCGCAGCG CATGAAGCTC (SEQ ID NO. 181) GAGCTTCATGCGCTGCGCATTG AATAAAGAGTCACCGGTTTCAG CAATAACCGT (SEQ ID NO. 182) | FSP1 |
| Zm-Pdc | G413N | TATGAAATGCAGTGGAACCACA TTGGTTGGTCGGTACCTGCCGC CTTC (SEQ ID NO. 183) GAAGGCGGCAGGTACCGACCAA CCAATGTGGTTCCACTGCATTT CATA (SEQ ID NO. 184) | KPNI |
| Ll-Kdc | G402S | GGACAACCGCTGTGGTCCAGTA TTGGGTATACGTTTCCAGCG (SEQ ID NO. 185) CGCTGGAAACGTATACCCAATA CTGGACCACAGCGGTTGTCC (SEQ ID NO. 186) | ACC1 |
| Ll-Kdc | V461I | TTTGCTTTATCATTAATAATGA CGGCTACACAATCGAGCGCGAA ATTCA ((SEQ ID NO. 187) TGAATTTCGCGCTCGATTGTGT | ASE1 |

TABLE 9-continued

Oligonucleotides used to mutate branched chain 2-oxoacid decarboxylase, kdcA, from *L. lactis* and pyruvate decarboxylase, PDC, from *Z. mobilis*

| Protein | Mutation | Primer sequences 5'-3' | Restr. site |
|---|---|---|---|
| | | AGCCGTCATTATTAATGATAAA GCAAA (SEQ ID NO. 188) | |

Mutant enzymes were expressed, purified and tested for OHB decarboxylase, pyruvate decarboxylase and MOV decarboxylase activity as described in Example 4. The results of the enzymatic measurements are summarized in Table 10. It was demonstrated that mutations W392Q, W392L and G413N in Zm-Pdc, and mutations G402S and V461I in Ll-KdcA increased activity and/or specificity for OHB.

TABLE 10

Summary of kinetic parameters of decarboxylase mutants on OHB, pyruvate and MOV

| Mutant Enzyme | Seq ID | Max. specific activity [μmol/(mg min)] | | Km [mM] | |
|---|---|---|---|---|---|
| | | Natural substrate[a] | OHB[b] | Natural substrate | OHB |
| Zm-Pdc W392Q | SEQ ID No. 190) | 1.39 | 0.19 | 9.2 | 2.9 |
| Zm-Pdc W392L | SEQ ID No. 192) | 0.09 | 0.04 | ns | 3.7 |
| Zm-Pdc G413N | SEQ ID No. 194) | 0.1 | 0.04 | ns | 1.4 |
| Ll-KdcA G402S | SEQ ID No. 196) | 3.1 | 0.09 | 1.5 | 1.5 |
| Ll-KdcA V461I | SEQ ID No. 198) | 2.76 | 0.24 | 0.15 | 2.8 |

[a]activity was measured at 10 mM MOV in case of KdcA mutants and 50 mM pyruvate in case of Pdc mutants
[b]activity was measured at 20 mM OHB
ns—not saturated at concentrations of up to 50 mM Example 6

Demonstration of 1,3-Propanediol Dehydrogenase Activity

The coding region of the alcohol dehydrogenase yqhD from *Escherichia coli* was amplified by PCR using high fidelity polymerase Phusion™ (Finnzymes) and the direct and reverse primers 5 '-TATCGTGCTAGCAT-GAACAACTTTAATCTGCACA-3' (SEQ ID No. 199) and 5'-TATAATGAATTCTTAGCGGGCGGCTTCG-TATATACGGCGGCTGACA-3' (SEQ ID No. 200) that introduced NheI and EcoRI restriction sites upstream of the start codon and downstream of the stop codon, respectively. Genomic DNA from *E. coli* MG1655 was used as the template. The PCR product was digested with NheI and EcoRI, ligated into the corresponding sites of pET28a+ (Novagen), in frame with a N-terminal hexa-His tag, using T4 DNA ligase (Biolabs). The ligation product was transformed into *E. coli* DH5α cells. The resulting pET28-Ec-yqhD plasmid was isolated and shown by DNA sequencing to contain the correct full-length sequence of the *E. coli* yqhD gene. The plasmid was used to transform *E. coli* BL21 (DE3) star cells and the enzyme with an N-terminal hexa-His tag was expressed and purified as described in Example 1.

Enzymatic assay:

PDO dehydrogenase activity was assayed by following the PDO-dependent reduction of NADP.

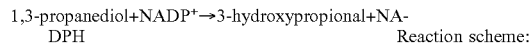

Reaction scheme:

The reaction mixture contained 60 mM Hepes (pH 8), 50 mM potassium chloride, 2 mM ZnSO$_4$, 10 mM NADP, (all products from Sigma), and appropriate amounts of purified enzyme or cell extract. Reactions were started by adding 100 mM 1,3-propanediol (PDO, Sigma). Enzymatic assays were carried out at 37° C. in 96-well flat bottomed microtiter plates in a final volume of 250 µL. The reactions were followed by the characteristic absorption of NADPH at 340 nm ($\epsilon_{NADH}$=6.22 mM$^{-1}$ cm$^{-1}$) in a microplate reader (Bio-Rad 680XR). The enzyme exhibited a PDO dehydrogenase activity of 0.15 µmol/(min mg).

Example 6

Demonstration of In Vitro Production of 1,3-Propanediol by the Synthetic Pathway The enzymes DHB dehydrogenase (Ec-Mdh R81A or Ec-LldD), OHB decarboxylase (Zm-Pdc or Sc-Pdc), and PDO dehydrogenase (Ec-YqhD) were expressed and purified as described in Example 1. In vitro synthesis of PDO was demonstrated by adding 20 mM DHB to a reaction mixture that contained 50 mM Hepes (pH 7), 50 µM thiamine pyrophosphate, 2 mM NADPH, 2 mM MgCl$_2$, 10 mM NAD or 1 mM DCIP, 160 µg/mL of DHB dehydrogenase, 10 µg/mL OHB decarboxylase, and 20 µg/mL PDO dehydrogenase. Control reactions contained all components but were lacking either DHB dehydrogenase (Control 1) or OHB decarboxylase (Control 2).

After 10 h of incubation at 37° C., the reaction mixtures were analysed by gas chromatography [GCMS-QP2010 Ultra Shimadzu; equipped with a FID detector (FID-2010 Plus Shimadzu); autosampler AOC20s (Shimadzu); splitless injector AOC20i (Shimadzu) (240° C.); column: Zebron ZB-WAX, 30 m×0.25 mm, d$_f$ 0.25 µm; and liner: Tapered focus Liner5×95×3.4 mm (SGE). Carrier gas was hydrogen at a total flow rate of 4.9 mL/min. Flame ionization was carried out using an air-hydrogen mixture (flow rates were 400 mL/min and 40 mL/min, respectively). Detector temperature was 250° C. Injected sample volume was 1 µL. The temperature program is provided in Table 11.

TABLE 11

Temperature program used for GC-FID analyses of reaction mixtures

| Columntemperature [° C.] | Hold [min] | Gradient [° C./min] | Runtime [min] |
|---|---|---|---|
| 50 | 0 | 0 | 0 |
| 95 | 0 | 20 | 2.15 |
| 160 | 5 | 40 | 3.52 |
| 230 | 2 | 50 | 12.27 |

Figure 3:
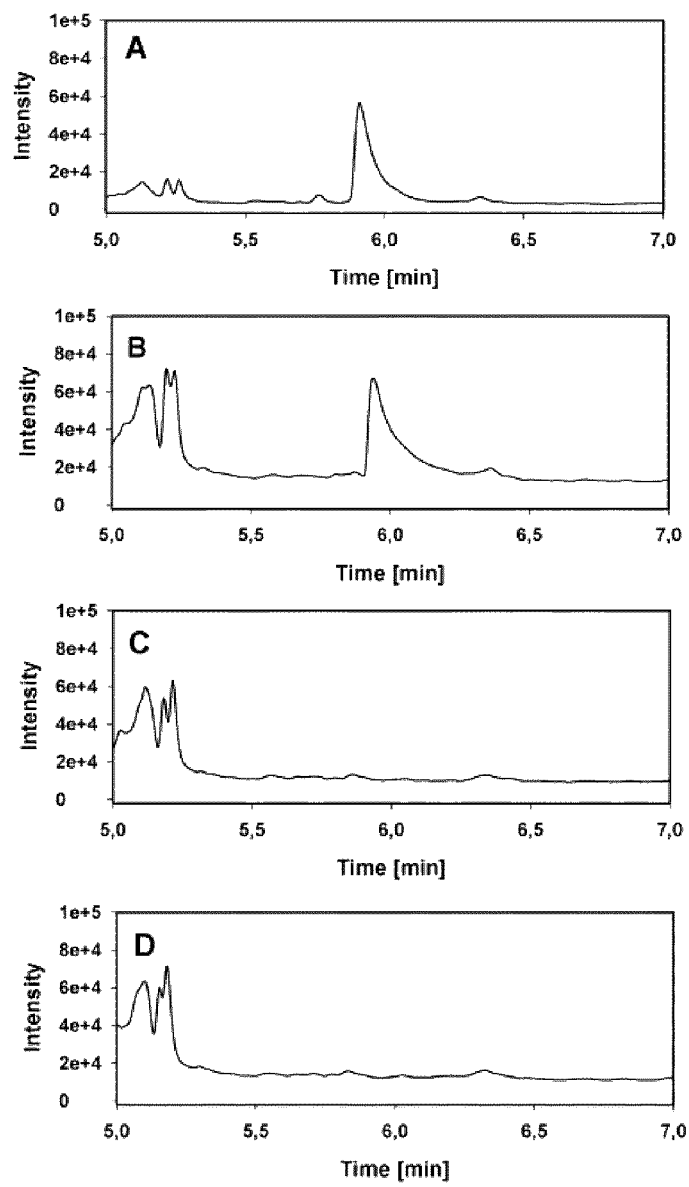
FIG. 3: GC-FID chromatograms showing the presence of 1,3-propanediol (PDO) after incubation of 20 mM DHB, 1 mM DCIP, 2 mM NADPH, and 50 µM thiamine pyrophosphate with different combinations of PDO pathway enzymes. (A) PDO standard at 1 mM, (B) Reaction 1: DHB dehydrogenase (160 µg/mL Ec-LldD), OHB decarboxylase (10 µg/mL Zm-Pdc), and PDO dehydrogenase (20 µg/mL Ec-YqhD); (C) Control 1: same as reaction 1 but without DHB dehydrogenase; (D) Control 2: same as reaction 1 but without OHB decarboxylase.
Figure 4:
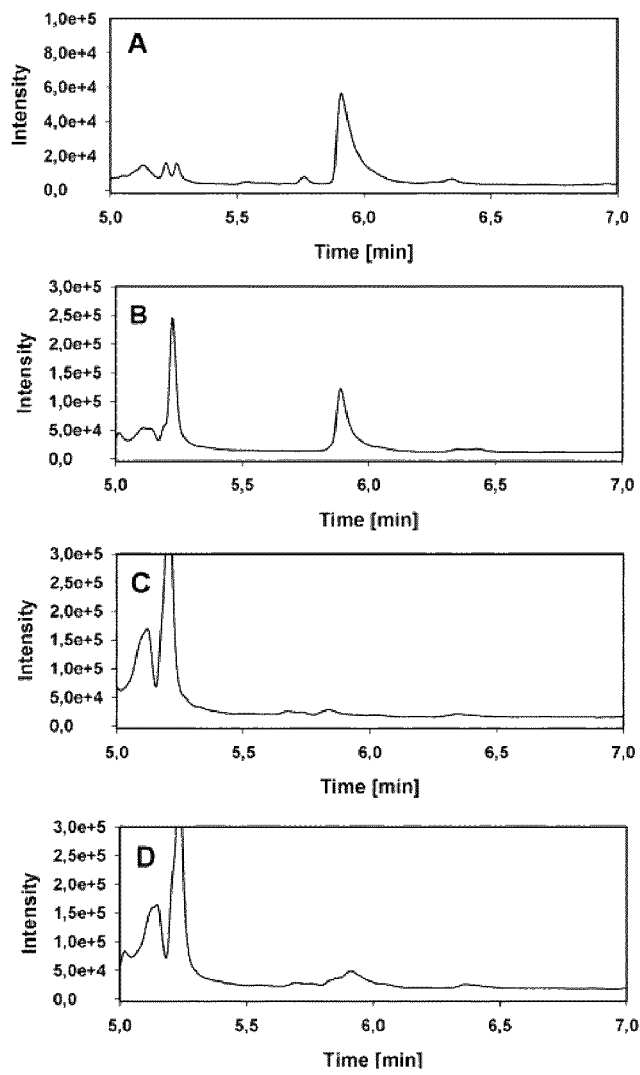
FIG. 4: GC-FID chromatograms showing the presence of 1,3-propanediol (PDO) after incubation of 20 mM DHB, 10 mM $NAD^+$, 2 mM NADPH, and 50 µM thiamine pyrophosphate with different combinations of PDO pathway enzymes. (A) PDO standard at 1 mM, (B) Reaction 1: DHB dehydrogenase (160 µg/mL Ec-Mdh R81A), OHB decarboxylase (10 µg/mL Ll-KdcA), and PDO dehydrogenase (20 µg/mL Ec-YqhD); (C) Control 1: same as reaction 1 but without PDO dehydrogenase; (D) Control 2: same as reaction 1 but without DHB dehydrogenase.

Chromatograms showing presence of PDO in the reactions containing all pathway enzymes and absence of PDO in samples containing only two out of three pathway enzymes are shown in FIGS. 3 and 4.

Example 7

Construction of Optimized Propanediol Producer Strains

Construction of the Plasmid pACT3-Op-PDO for Expression of DHB Dehydrogenase (Ec-Mdh R81A), OHB Decarboxylase (Zm-Pdc), and PDO Dehydrogenase (Ec-YqhD)

Vector pACT3-yqhD was constructed by amplifying the coding sequence of yqhD using the forward and reverse primers 5'-TATAATGAGCTCTTTAACTTTAAGAAGGA-GATATACCATGAACAACTTTAAT CTGCACAC-CCCAACC-3' (SEQ ID No. 201) and 5 '-TATAATGGATC-CTTAGCGGGCGGCTTCGTA-3' (SEQ ID No. 202) that added a SacI and a BamH1 restriction site upstream of the start codon and downstream of the stop codon. Plasmid pET28-yqhD was used as the template. The PCR fragment was purified and ligated into the SacI and BamHI sites of vector pACT3 (Dykxhoorn, et al. (1996) A set of compatible tac promoter expression vectors. Gene 177, 133-136.). Vector pACT3-yqhD was then digested in XbaI and HindIII sites, situated at the end of the Ec-yqhD coding sequence. Ec-mdh R81A and Zm-pdc genes were amplified by PCR using the primer pairs 5'-GCCCGCTAAGGATC-CTCTAGGGAGGTCTAGAATGAAAGTCGCAGTC-CTCG GC-3' (SEQ ID No. 203); 5'-CGAGCCTCCTTACT-TATTAACGAACTCTTCGCC-3' (SEQ ID No. 204), and 5'-CATAGGGAGGCTCGAGATGTATACCGTTGGGGAT-TATCTG-3' (SEQ ID No. 205); 5'-CGCCAAAACA-GAAGCTTGACGTCCTAGAGGAGCTTGTTAACAG-GCTT-3', (SEQ ID No. 206) respectively. Amplified PCR fragments (2 µL each) and digested pACT-yqhD plasmid (3 µL) were mixed and incubated with 2 µL of In-fusion enzyme (Clontech) for 20 min at 50° C. 2 µL of the reaction mix were then transformed into Stellar™ Competent Cells. Presence of the complete operon in the resulting plasmid pACT3-op-PDO was confirmed by sequencing isolated plasmid DNA recovered from transformed clones.

Construction of Strains with Optimized Carbon Flux Repartitioning for Propanediol Production Several genes were disrupted in E. coli strain MG1655 in order to optimise carbon flux repartitioning and cofactor supply for PDO production. Gene deletions were carried out using the lambda red recombinase method according to Datsenko et al. (Datsenko & Wanner, 2000), which can be refined to allow for more efficient multiple gene deletions using the protocol of Mizoguchi (Mizoguchi, Tanaka-Masuda, & Mori, 2007). Another alternative to introduce multiple chromosomal gene deletions in E coli relies on the transfer of mutations from one strain to another by P1 phage transduction (Thomason, Costantino, Shaw, & Court, 2007).

The deletion cassettes were prepared by PCR using high fidelity polymerase Phusion™ (Finnzymes), and the FRT-flanked kanamycin resistance gene (kan) of plasmid pKD4 as the template (Datsenko & Wanner, 2000). Sense primers contained sequences corresponding to the 5' end of each targeted gene (underlined) followed by 20 bp corresponding to the FRT-kan-FRT cassette of pKD4. Anti-sense primers contained sequences corresponding to the 3' end region of each targeted gene (underlined) followed by 20 bp corresponding to the cassette. The primers are described in Table 11. PCR products were digested with DpnI and purified prior to transformation.

E. coli MG1655 strain was rendered electro-competent by growing the cells to an OD$_{600}$ of 0.6 in LB liquid medium at 37° C., concentrating the cells 100-fold, and washing them twice with ice-cold 10% glycerol. The cells were transformed with plasmid pKD46 (Datsenko & Wanner, 2000) by electroporation (2.5 kV, 200 Ω, 25 µF, in 2 mm gap cuvettes). Transformants were selected at 30° C. on ampicillin (100 µg/mL) LB solid medium.

Disruption cassettes were transformed into electro-competent E. coli strains harbouring the lambda Red recombinase-expressing plasmid pKD46. The cells were grown at 30° C. in liquid SOB medium containing ampicillin (100

µg/mL). The lambda red recombinase system was induced by adding 10 mM arabinose when $OD_{600}$ of the cultures reached 0.1. Cells were further grown to an $OD_{600}$ of 0.6 before they were harvested by centrifugation, washed twice with ice-cold 10% glycerol, and transformed with the disruption cassette by electroporation. After an overnight phenotypic expression at 30° C. in LB liquid medium, cells were plated on solid LB medium containing 25 µg/mL kanamycin. Transformants were selected after cultivation at 30° C.

The gene replacement was verified by colony PCR using Crimson Taq polymerase (NEB). A first reaction was carried out with the flanking locus-specific primers (see Table 12) to verify simultaneous loss of the parental fragment and gain of the new mutant specific fragment. Two additional reactions were done by using one locus-specific primer together with one of the corresponding primers k1 rev, or k2 for (see Table 6) that align within the FRT-kanamycin resistance cassette (sense locus primer/k1 rev and k2 for/reverse locus primer).

The resistance gene (FRT-kan-FRT) was subsequently excised from the chromosome using the FLP recombinase-harbouring plasmid pCP20 (Cherepanov & Wackernagel, 1995) leaving a scar region containing one FRT site. pCP20 is an ampicillin and CmR plasmid that shows temperature-sensitive replication and thermal induction of FLP recombinase synthesis. Kanamycin resistant mutants were transformed with pCP20, and ampicillin-resistant transformants were selected at 30° C. Transformants were then grown on solid LB medium at 37° C. and tested for loss of all antibiotic resistances. Excision of the FRT-kanamycin cassette was analysed by colony PCR using crimson taq polymerase and the flanking locus-specific primers (Table 13). Multiple deletions were obtained by repeating the above described steps.

TABLE 12

Primers used for gene disruptions. Sequences homologous to target genes are underlined

| Gene | Primer | Sequence |
|---|---|---|
| ldhA | Δ_ldhA_for | gaaggttgcgcctacactaagcatagttg ttgatgagtgtaggctggagctgcttc (SEQ ID No. 1) |
| | Δ_ldhA_rev | ttaaaccagttcgttcgggcaggtttcgc cttttcatgggaattagccatggcc SEQ ID No. 2) |
| adhE | Δ_adhE_for | atggctgttactaatgtcgctgaacttaa cgcactcgtagagcgtgtgtaggctggag ctgcttc (SEQ ID No. 3) |
| | Δ_adhE_rev | ttaagcggatttttttcgcttttttctcag ctttagccggagcagccatatgaatatcc tccttag (SEQ ID No. 4) |
| ackA | Δ_ackA_for | atgtcgagtaagttagtactggttctgaa ctgcggtagttcttcagtgtaggctggag ctgcttc (SEQ ID No. 5) |
| | Δ_ackA_rev | tcaggcagtcaggcggctcgcgtcttgcg cgataaccagttcttccatatgaatatcc tccttag (SEQ ID No. 6) |
| focA-pflB | Δ_focA-pflB_for | ttactccgtatttgcataaaaaccatgcg agttacgggcctataagtgtaggctggag ctgcttc (SEQ ID No. 7) |
| | Δ_focA-pflB_rev | atagattgagtgaaggtacgagtaataac gtcctgctgctgttctcatatgaatatcc tccttag (SEQ ID No. 8) |
| pta | Δ_pta_for | gtgtcccgtattattatgctgatccctac cggaaccagcgtcggtgtgtaggctggag ctgcttc (SEQ ID No. 9) |

TABLE 12-continued

Primers used for gene disruptions. Sequences homologous to target genes are underlined

| Gene | Primer | Sequence |
|---|---|---|
| | Δ_pta_rev | ttactgctgctgtgcagactgaatcgcag tcagcgcgatggtgtacatatgaatatcc tccttag (SEQ ID No. 10) |
| poxB | Δ_poxB_for | atgaaacaaacggttgcagcttatatcgc caaaacactcgaatcggtgtaggctggag ctgcttc (SEQ ID No. 11) |
| | Δ_poxB_rev | ttaccttagccagtttgttttcgccagtt cgatcacttcatcacccatatgaatatcc tccttag (SEQ ID No. 12) |
| sad | Δ_sad_for | atgaccattactccggcaactcatgcaat ttcgataaatcctgccgtgtaggctggag ctgcttc (SEQ ID No. 13) |
| | Δ_sad_rev | tcagatccggtctttccacaccgtctgga tattacagaattcgtgcatatgaatatcc tccttag (SEQ ID No. 14) |
| gabD | Δ_gabD_for | atgaaacttaacgacagtaacttattccg ccagcaggcgttgattgtgtaggctggag ctgcttc (SEQ ID No. 15) |
| | Δ_gabD_rev | ttaaagaccgatgcacatatatttgattt ctaagtaatcttcgatcatatgaatatcc tccttag (SEQ ID No. 16) |
| gadA | Δ_gadA_for | atggaccagaagctgttaacggatttccg ctcagaactactcgatgtgtaggctggag ctgcttc (SEQ ID No. 17) |
| | Δ_gadA_rev | tcaggtgtgtttaaagctgttctgctggg caatacccctgcagtttcatatgaatatcc tccttag (SEQ ID No. 18) |
| gadB | Δ_gadB_for | atggataagaagcaagtaacggatttaag gtcggaactactcgatgtgtaggctggag ctgcttc (SEQ ID No. 19) |
| | Δ_gadB_rev | tcaggtatgtttaaagctgttctgttggg caatacccctgcagtttcatatgaatatcc tccttag (SEQ ID No. 20) |
| gadC | Δ_gadC_for | atggctacatcagtacagacaggtaaagc taagcagctcacattagtgtaggctggag ctgcttc (SEQ ID No. 21) |
| | Δ_gadC_rev | ttagtgtttcttgtcattcatcacaatat agtgtggtgaacgtgccatatgaatatcc tccttag (SEQ ID No. 22) |
| sfcA | Δ_sfcA_for | atggaaccaaaaacaaaaaaacagcgttc gctttatatcccttacgtgtaggctggag ctgcttc (SEQ ID No. 23) |
| | Δ_sfcA_rev | ttagatggaggtacggcggtagtcgcggt attcggcttgccagaacatatgaatatcc tccttag (SEQ ID No. 24) |
| maeB | Δ_maeB_for | atggatgaccagttaaaacaaagtgcact tgatttccatgaatttgtgtaggctggag ctgcttc (SEQ ID No. 25) |
| | Δ_maeB_rev | ttacagcggttgggtttgcgcttctacca cggccagcgccaccatcatatgaatatcc tccttag (SEQ ID No. 26) |
| pykA | Δ_pykA_for | atgtccagaaggcttcgcagaacaaaaat cgttaccacgttaggcgtgtaggctggag ctgcttc (SEQ ID No. 27) |
| | Δ_pykA_rev | ttactctaccgttaaaatacgcgtggtat tagtagaacccacggtcatatgaatatcc tccttag (SEQ ID No. 28) |
| pykF | Δ_pykF_for | atgaaaaagaccaaaattgtttgcaccat cggaccgaaaaccgaagtgtaggctggag ctgcttc (SEQ ID No. 29) |
| | Δ_pykF_rev | ttacaggacgtgaacagatgcggtgttag tagtgccgctcggtaccatatgaatatcc tccttag (SEQ ID No. 30) |

TABLE 12-continued

Primers used for gene disruptions. Sequences homologous to target genes are underlined

| Gene | Primer | Sequence |
|---|---|---|
| mgsA | Δ_mgsA_for | atggaactgacgactcgcactttacctgcgcggaaacatattgcggtgtaggctggagctgcttc (SEQ ID No. 31) |
|  | Δ_mgsA_rev | ttacttcagacggtccgcgagataacgctgataatcgggatcagcatatgaatatcctccttag (SEQ ID No. 32) |
| iclR | Δ_iclR_for | atggtcgcacccattcccgcgaaacgcggcagaaaacccgccgttgtgtaggctggagctgcttc (SEQ ID No. 33) |
|  | Δ_iclR_rev | tcagcgcattccaccgtacgccagcgtcacttccttcgccgctttcatatgaatatcctccttag (SEQ ID No. 34) |
| icd | Δ_icd_for | atggaaagtaaagtagttgttccggcacaaggcaagaagatcaccgtgtaggctggagctgcttc (SEQ ID No. 35) |
|  | Δ_icd_rev | ttacatgttttcgatgatcgcgtcaccaaactctgaacatttcagcatatgaatatcctccttag (SEQ ID No. 36) |
| sucA | Δ_sucA_for | atgcagaacagcgctttgaaagcctggttggactcttcttacctcgtgtaggctggagctgcttc (SEQ ID No. 37) |
|  | Δ_sucA_rev | ttattcgacgttcagcgcgtcattaaccagatctgttgctgtttcatatgaatatcctccttag (SEQ ID No. 38) |
| sucB | Δ_sucB_for | atgagtagcgtagatattctggtccctgacctgcctgaatccgtagtgtaggctggagctgcttc (SEQ ID No. 39) |
|  | Δ_sucB_rev | ctacacgtccagcagcagacgcgtcggatcttccagcaactctttcatatgaatatcctccttag (SEQ ID No. 40) |
| frdA | Δ_frdA_for | gtcaaacctttcaagccgatcttgccatgtaggcgccggtggcgtgtaggctggagctgcttc (SEQ ID No. 41) |
|  | Δ_frdA_rev | tcagccattcgccttctccttcttattggctgcttccgccttatccatatgaatatcctccttag (SEQ ID No. 42) |
| frdB | Δ_frdB_for | atggctgagatgaaaaacctgaaaattgaggtggtgcgctataacgtgtaggctggagctgcttc (SEQ ID No. 43) |
|  | Δ_frdB_rev | ttagcgtggtttcagggtcgcgataagaaagtctttcgaactttccatatgaatatcctccttag (SEQ ID No. 44) |
| frdC | Δ_frdC_for | atgacgactaaacgtaaaccgtatgtacggccaatgacgtccaccgtgtaggctggagctgcttc (SEQ ID No. 45) |
|  | Δ_frdC_rev | ttaccagtacagggcaacaaacaggattacgatggtggcaaccaccatatgaatatcctccttag (SEQ ID No. 46) |
| frdD | Δ_frdD_for | atgattaatccaaatccaaagcgttcgacgaaccggtattctgggtgtaggctggagctgcttc (SEQ ID No. 47) |
|  | Δ_frdD_rev | ttagattgtaacgacaccaatcagcgtgacaactgtcaggatagccatatgaatatcctccttag (SEQ ID No. 48) |
| ptsI | Δ_ptsI_for | atgatttcaggcattttagcatccccgggtatcgctttcggtaaagtgtaggctggagctgcttc (SEQ ID No. 49) |
|  | Δ_ptsI_rev | ttagcagattgttttttcttcaatgaacttgttaaccagctcatcatatgaatatcctccttag (SEQ ID No. 50) |
| ptsG | Δ_ptsG_for | atgtttaagaatgcatttgctaacctgcaaaaggtcggtaaatcggtgtaggctggagctgcttc (SEQ ID No. 51) |
|  | Δ_ptsG_rev | ttagtggttacggatgtactcatccatctcggttttcaggttatccatatgaatatcctccttag (SEQ ID No. 52) |
| lacI | Δ_lacI_for | gtgaaaccagtaacgttatacgatgtcgcagagtatgccggtgtcgtgtaggctggagctgcttc (SEQ ID No. 53) |
|  | Δ_lacI_rev | tcactgcccgctttccagtcgggaaacctgtcgtgccagctgcatcatatgaatatcctccttag (SEQ ID No. 54) |
| pgi | Δ_pgi_for | atgaaaaacatcaatccaacgcagaccgctgcctggcaggcactagtgtaggctggagctgcttc (SEQ ID No. 55) |
|  | Δ_pgi_rev | ttaaccgcgccacgctttatagcggttaatcagaccattggtcgacatatgaatatcctccttag (SEQ ID No. 56) |
| eda | Δ_eda_for | atgaaaaactggaaaacaagtgcagaatcaatcctgaccaccgcgtaggctggagctgcttc (SEQ ID No. 57) |
|  | Δ_eda_for | ctcgatcgggcattttgacttttacgcttagcgccttctacagcatatgaatatcctccttag (SEQ ID No. 58) |

TABLE 13

Primer pairs used for verification of gene disruptions

| Deleted-gene | Forward primer | Reverse primer |
|---|---|---|
| K2 for/ k1 rev | cggtgccctgaatgaactgc (SEQ ID No. 59) | cagtcatagccgaatagcct (SEQ ID No. 60) |
| ldhA | atacgtgtcccgagcggtag (SEQ ID No. 61) | tacacatcccgccatcagca (SEQ ID No. 62) |
| adhE | gaagtaaacgggaaaatcaa (SEQ ID No. 63) | agaagtggcataagaaaacg (SEQ ID No. 64) |
| ackA | ccattggctgaaaattacgc (SEQ ID No. 65) | gttccattgcacggatcacg (SEQ ID No. 66) |
| focA_pflB | atgccgtagaagccgccagt (SEQ ID No. 67) | tgttggtgcgcagctcgaag (SEQ ID No. 68) |
| pta | gcaaatctggtttcatcaac (SEQ ID No. 69) | tcccttgcacaaaacaaagt (SEQ ID No. 70) |
| poxB | ggatttggttctcgcataat (SEQ ID No. 71) | agcattaacggtagggtcgt (SEQ ID No. 72) |
| sad | gctgattctcgcgaataaac (SEQ ID No. 73) | aaaaacgttcttgcgcgtct (SEQ ID No. 74) |
| gabD | tctgtttgtcaccaccccgc (SEQ ID No. 75) | aagccagcacctggaagcag (SEQ ID No. 76) |
| gadA | aagagctgccgcaggaggat (SEQ ID No. 77) | gccgccctcttaagtcaaat (SEQ ID No. 78) |
| gadB | ggattttagcaatattcgct (SEQ ID No. 79) | cctaatagcaggaagaagac (SEQ ID No. 80) |
| gadC | gctgaactgttgctggaaga (SEQ ID No. 81) | ggcgtgcttttacaactaca (SEQ ID No. 82) |
| sfcA | tagtaaataacccaaccggc (SEQ ID No. 83) | tcagtgagcgcagtgtttta (SEQ ID No. 84) |

TABLE 13-continued

Primer pairs used for verification of gene disruptions

| Deleted-gene | Sequence (5'-3') | |
|---|---|---|
| | Forwardprimer | Reverse primer |
| maeB | attaatggtgagagtttgga (SEQ ID No. 85) | tgcttttttttattattcgc (SEQ ID No. 86) |
| pykA | tttatatgcccatggtttct (SEQ ID No. 87) | atctgttagaggcggatgat (SEQ ID No. 88) |
| pykF | ctggaacgttaaatctttga (SEQ ID No. 89) | ccagtttagtagctttcatt (SEQ ID No. 90) |
| iclR | gatttgttcaacattaactcatcgg (SEQ ID No. 91) | tgcgattaacagacaccctt (SEQ ID No. 92) |
| mgsA | tctcaggtgctcacagaaca (SEQ ID No. 93) | tatggaagaggcgctactgc (SEQ ID No. 94) |
| icd | cgacctgctgcataaacacc (SEQ ID No. 95) | tgaacgctaaggtgattgca (SEQ ID No. 96) |
| sucA | acgtagacaagagctcgcaa (SEQ ID No. 97) | catcacgtacgactgcgtcg (SEQ ID No. 98) |
| sucB | tgcaactttgtgctgagcaa (SEQ ID No. 99) | tatcgcttccgggcattgtc (SEQ ID No. 100) |
| frdA | aaatcgatctcgtcaaatttcagac (SEQ ID No. 101) | aggaaccacaaatcgccata (SEQ ID No. 102) |
| frdB | gacgtgaagattactacgct (SEQ ID No. 103) | agttcaatgctgaaccacac (SEQ ID No. 104) |
| frdC | tagccgcgaccacggtaagaaggag (SEQ ID No. 105) | cagcgcatcacccggaaaca (SEQ ID No. 106) |
| frdD | atcgtgatcattaacctgat (SEQ ID No. 107) | ttaccctgataaattaccgc (SEQ ID No. 108) |
| lacI | gaatctggtgtatatggcga (SEQ ID No. 109) | tcttcgctattacgccagct (SEQ ID No. 110) |
| pgi | ttgtcaacgatggggtcatg (SEQ ID No. 111) | aaaaatgccgacataacgtc (SEQ ID No. 112) |
| ptsG | ccatccgttgaatgagtttt (SEQ ID No. 113) | tggtgttaactggcaaaatc (SEQ ID No. 114) |
| ptsI | gtgacttccaacggcaaaag (SEQ ID No. 115) | ccgttggtttgatagcaata (SEQ ID No. 116) |
| eda | Gacagacaggcgaactgacg (SEQ ID No. 117) | Gcgcagatttgcagattcgt (SEQ ID No. 118) |

The plasmid expressing the enzymes that build up the pathway leading from DHB to PDO (pACT3-op-PDO) was transformed into the E. coli MG1655 wild-type strain. Transformants were selected on solid LB medium containing chloramphenicol (25 μg/mL) and kanamycin (50 μg/mL). Non-exclusive examples of constructed strains are listed in Table 14.

TABLE 14

Examples of strains constructed for DHB production

| Strain | Relevant Genotype |
|---|---|
| MG1655 | Wild-type |
| ECE90 | pACT3 (empty plasmid) |
| ECE91 | pACT3-op-PDO |

Example 8

Zymotic Production of Propanediol

Strains and medium: Experiments were carried out with strains listed in Table 14. 1 Liter culture medium contained, 20 g glucose, 18 g $Na_2HPO_4*12H_2O$, 3 g $KH_2PO_4$, 0.5 g NaCl, 2 g $NH_4Cl$, 0.5 g $MgSO_4*7H_2O$, 0.015 $CaCl_2*2H_2O$, 1 mL of 0.06 mol/L $FeCl_3$ stock solution prepared in 100 times diluted concentrated HCl, 2 mL of 10 mM thiamine HCl stock solution, 20 g MOPS, and 1 mL of trace element solution (containing per liter: 0.04 g $Na_2EDTA*2H_2O$, 0.18 g $CoCl_2*6H_2O$, $ZnSO4*7H_2O$, 0.04 g $Na_2MoO4*2H_2O$, 0.01 g $H_3BO_3$, 0.12 g $MnSO_4*H_2O$, 0.12 g $CuCl_2*H2O$). Medium pH was adjusted to 7 and medium was filter-sterilized. Chloramphenicol (Sigma) was added at a concentration of 25 μg/mL.

Cultivation Conditions:

All cultivations were carried out at 37° C. on an Infors rotary shaker running at 170 rpm. Cells were grown on glucose-containing mineral medium. PDO production was assayed under two conditions:

(A) Growth on glucose-containing mineral medium in the presence of 20 mM DHB, or
(B) Incubation of a cell suspension in phosphate buffer with 20 mM DHB.

Experimental details for condition (A): Overnight cultures (3 mL medium in test tube) were inoculated from glycerol stocks and used to adjust an initial $OD_{600}$ of 0.05 in 100 mL growth cultures cultivated in 500 mL shake flasks. IPTG was added at a concentration of 1 mmol/L when $OD_{600}$ in the growth cultures reached 1. At the same time DHB was added to the cultures at a concentration of 20 mM. Supernatant of the cultures was analysed after 20 h of incubation.

Experimental details for condition (B): Overnight cultures (3 mL medium in test tube) were inoculated from glycerol stocks and used to adjust an initial $OD_{600}$ of 0.05 in 100 mL growth cultures cultivated in 500 mL shake flasks. IPTG was added at a concentration of 1 mmol/L when $OD_{600}$ in the growth cultures reached 1. Cells were harvested by centrifugation after having been incubated with IPTG during 4 h. Cells were washed twice with distilled water and were resuspended in 0.5 mL of 50 mM phosphate buffer at pH 7 to adjust a cell concentration of 5.5 g (cellular dry weight)/L. DHB was added at a concentration of 20 mM. PDO content was quantified after 20 h of incubation.

Estimation of PDO Concentration by LC-MS Analyses:

Liquid anion exchange chromatography was performed on an ICS-3000 system from Dionex (Sunnyvale, USA) equipped with an automatic eluent (KOH) generator system (RFIC, Dionex), and an autosampler (AS50, Dionex) holding the samples at 4° C. Analytes were separated on an IonPac AS11 HC (250×2 mm, Dionex) column protected by an AG11 HC (50×2 mm, Dionex) pre-column. Column temperature was held at 25° C., flow rate was fixed at 0.25 mL/min, and analytes were eluted applying the KOH gradient described earlier (Groussac E, Ortiz M & Francois J (2000): Improved protocols for quantitative determination of metabolites from biological samples using high performance ionic-exchange chromatography with conductimetric and pulsed amperometric detection. *Enzyme. Microb. Technol.* 26, 715-723). Injected sample volume was 15 µL. For background reduction, an ASRS ultra II (2 mm, external water mode, 75 mA) anion suppressor was used. Analytes were quantified using a mass-sensitive detector (MSQ Plus, Thermo) running in ESI mode (split was ⅓, nitrogen pressure was 90 psi, capillary voltage was 3.5 kV, probe temperature was 450° C.).

Results:

Condition A: The PDO concentration in the supernatant of strains ECE 90 and ECE91 after 20 h of incubation was 0 mg/L and 0.92 mg/L, respectively.

Condition B: The PDO concentration in the supernatant of strains ECE 90 and ECE91 after 20 h of incubation was 0.11 mg/L and 7.56 mg/L, respectively.

Zymotic production of PDO via the synthetic pathway was therefore demonstrated.

REFERENCES

Cherepanov, P. P. & Wackernagel, W. (1995). Gene disruption in *Escherichia coli*: TcR and KmR cassettes with the option of Flp-catalyzed excision of the antibiotic-resistance determinant. *Gene* 158, 9-14.

Datsenko, K. A. & Wanner, B. L. (2000). One-step inactivation of chromosomal genes in *Escherichia coli* K-12 using PCR products. *Proc. Natl. Acad. Sci. U.S.A* 97, 6640-6645.

Emptage, M., Haynie, S. L., Laffend, L. A., Pucci, J. P. & Whited, G. M. (2000). process for the biological production of 1,3-propanediol with high titer.

Hadicke, O. & Klamt, S. (2010). CASOP: a computational approach for strain optimization aiming at high productivity. *J. Biotechnol* 147, 88-101.

Klamt, S., Saez-Rodriguez, J. & Gilles, E. D. (2007). Structural and functional analysis of cellular networks with CellNetAnalyzer. *BMC Syst Biol* 1, 2.

Laffend, L. A., Nagarajan, V. & Nakamura, C. E. (1995). Bioconversion of a fermentable carbon source to 1,3-propanediol by a single microorganism.

Mizoguchi, H., Tanaka-Masuda, K. & Mori, H. (2007). A simple method for multiple modification of the *Escherichia coli* K-12 chromosome. *Biosci. Biotechnol. Biochem* 71, 2905-2911.

Nakamura, C. E. & Whited, G. M. (2003). Metabolic engineering for the microbial production of 1,3-propanediol. *Curr. Opin. Biotechnol* 14, 454-459.

Sambrook, J., Fritsch, E. F. & Maniatis, T. (1989). Molecular Cloning: A Laboratory Manual, 2 éd. Cold Spring Harbor: Cold Spring Harbor Laboratory Press.

Saxena, R. K., Anand, P., Saran, S. & Isar, J. (2009). Microbial production of 1,3-propanediol: Recent developments and emerging opportunities. *Biotechnol. Adv* 27, 895-913.

Schuster, S., Dandekar, T. & Fell, D. A. (1999). Detection of elementary flux modes in biochemical networks: a promising tool for pathway analysis and metabolic engineering. *Trends Biotechnol* 17, 53-60.

Thomason, L. C., Costantino, N., Shaw, D. V. & Court, D. L. (2007). Multicopy plasmid modification with phage lambda Red recombineering. *Plasmid* 58, 148-158.

The invention claimed is:

1. A modified microorganism for producing 1,3-propanediol (PDO) from a carbon substrate, the microorganism comprising:
   a pathway for synthesis of 2,4-dihydroxybutyrate (DHB); and
   a three-step metabolic pathway comprising:
   conversion of DHB to obtain 2-oxo-4-hydroxybutyrate (OHB) by an enzyme having 2,4-DHB dehydrogenase activity,
   decarboxylation of the OHB to obtain 3-hydroxypropionaldehyde by an enzyme having 2-oxo-4-hydroxybutyrate decarboxylase activity, and
   reduction of the obtained 3-hydroxypropionaldehyde to obtain PDO with an enzyme having 3-hydroxypropionaldehyde reductase activity,
   wherein the modified microorganism has been transformed by the introduction of at least three genes respectively encoding the enzyme having DHB dehydrogenase activity, the enzyme having 2-oxo-4-hydroxybutyrate decarboxylase activity, and the enzyme having 3-hydroxypropionaldehyde reductase activity.

2. The modified microorganism of claim 1, wherein the pathway for the synthesis of DHB is from malate.

3. The modified microorganism according to claim 2, wherein the microorganism has been further modified by the introduction of genes encoding:
   a malate kinase catalyzing the transformation of malate into 4-phospho-malate,
   a malate semialdehyde dehydrogenase catalyzing the transformation of 4-phospho-malate into malate-4-semialdehyde, and
   a malate semialdehyde reductase catalyzing the transformation of malate-4-semialdehyde into 2,4-DHB.

4. The modified microorganism of claim 1, wherein the enzymes are encoded by an endogenous or a heterologous gene.

5. The modified microorganism of claim 1, wherein the enzyme having 2,4-DHB dehydrogenase activity is an enzyme having lactate dehydrogenase or malate dehydrogenase activity.

6. The modified microorganism of claim 1, wherein the enzyme having 2,4-DHB dehydrogenase activity is obtained by at least one mutation of an enzyme, said mutation improving activity and/or substrate affinity of the enzyme for DHB.

7. The modified microorganism of claim 5, wherein the enzyme having 2,4-DHB dehydrogenase activity is a gene product encoded by a gene selected from the group consisting of IdhA from *Lactococcus lactis*, lldD from *Escherichia coli*, lldD from *E. coli* carrying a mutation at position Val108 (by reference to SEQ ID No. 122), mdh from *E. coli*, mdh from *Bacillus subtilis*, and mdh from *E. coli* carrying a mutation in at least one position selected from the group consisting of (by reference to SEQ ID No. 124): Ile12, Arg81, Lys82, Met85, Asp86, Val93, Ile117, Gly179, Thr211, and Met227 (by reference to SEQ ID No.126).

8. The modified microorganism of claim 7, wherein the enzyme having 2,4-DHB dehydrogenase activity is:
   encoded by a polynucleotide having the sequence of SEQ ID No. 119, SEQ ID No. 121, SEQ ID No. 153, SEQ ID No. 155, SEQ ID No. 157, SEQ ID No. 159, SEQ ID No. 161, SEQ ID No. 163, SEQ ID No. 165, SEQ ID No. 167, SEQ ID No. 169, SEQ ID No. 171, SEQ ID No. 173, or any sequence sharing a homology of at least 50% with the sequence of SEQ ID No. 119, SEQ ID No. 121, SEQ ID No. 153, SEQ ID No. 155, SEQ ID No. 157, SEQ ID No. 159, SEQ ID No. 161, SEQ ID No. 163, SEQ ID No. 165, SEQ ID No. 167, SEQ ID No. 169, SEQ ID No. 171, or SEQ ID No. 173, and/or
   a polypeptide having the sequence of SEQ ID No. 120, SEQ ID No. 122, SEQ ID No. 154, SEQ ID No. 156, SEQ ID No. 158, SEQ ID No. 160, SEQ ID No. 162, SEQ ID No. 164, SEQ ID No. 166, SEQ ID No. 168, SEQ ID No. 170, SEQ ID No. 172, SEQ ID No. 174, or any sequence sharing a homology of at least 50% with the sequence of SEQ ID No. 120, SEQ ID No. 122, SEQ ID No. 154, SEQ ID No. 156, SEQ ID No. 158, SEQ ID No. 160, SEQ ID No. 162, SEQ ID No. 164, SEQ ID No. 166, SEQ ID No. 168, SEQ ID No. 170, SEQ ID No. 172, or SEQ ID No. 174.

9. The modified microorganism of claim 1, wherein the enzyme having 2-oxo-4-hydroxybutyrate decarboxylase activity is an enzyme having a 2-keto acid decarboxylase activity.

10. The modified microorganism of claim 1, wherein the enzyme having 4-hydroxybutyrate decarboxylase activity is obtained by at least one mutation of an enzyme, said mutation improving activity and/or substrate affinity of the enzyme for OHB.

11. The modified microorganism of claim 9, wherein the enzyme having 2-oxo-4-hydroxybutyrate decarboxylase activity is a gene product encoded by a gene selected from the group consisting of PDC1, PDC5, PDC6, ARO10, and THI3 genes from *Saccharomyces cerevisiae*; kivD and kdcA genes from *Lactococcus lactis*; pdc gene from *Clostridium acetobutylicum*; PDC2 and PDC3 genes from *Arabidopsis thaliana*; PDC1, PDC2, and ARO10 genes from *Pichia stipitis*; pdc gene from *Zymomonas mobilis*; sucA gene from *Escherichia coli*; dxs gene from *Escherichia coli*; pdc gene from *Z. mobilis* carrying a mutation in at least one position selected from the group consisting of: Tyr290, Trp392, Gly413, and Ile476 (by reference to SEQ ID No.128); and kdcA gene from *L. lactis* carrying a mutation in at least one position selected from the group consisting of: Gln377, Phe381, Phe382, Gly402 Val461, Ile465, and Phe542 (by reference to SEQ ID No.130).

12. The modified microorganism of claim 11, wherein the enzyme having 4-hydroxybutyrate decarboxylase activity is encoded by a polynucleotide having the sequence of SEQ ID No. 129, SEQ ID No. 127, SEQ ID No. 207, SEQ ID No. 189, SEQ ID No. 191, SEQ ID No. 193, SEQ ID No. 195, SEQ ID No. 197, or any sequence sharing a homology of at least 50% with the sequence of SEQ ID No. 129, SEQ ID No. 127, SEQ ID No. 207, SEQ ID No. 189, SEQ ID No. 191, SEQ ID No. 193, SEQ ID No. 195, or SEQ ID No. 197, and/or a polypeptide having the sequence of SEQ ID No. 130, SEQ ID No. 128, SEQ ID No. 208, SEQ ID No. 190, SEQ ID No. 192, SEQ ID No. 194, SEQ ID No. 196, SEQ ID No. 198, or any sequence sharing a homology of at least 50% with the sequence of SEQ ID No. 130, SEQ ID No. 128, SEQ ID No. 208, SEQ ID No. 190, SEQ ID No. 192, SEQ ID No. 194, SEQ ID No. 196, or SEQ ID No. 198.

13. The modified microorganism of claim 1, wherein the enzyme having 3-hydroxypropionaldehyde reductase activity is an enzyme having hydroxyaldehyde reductase activity, alcohol dehydrogenase activity, lactaldehyde reductase activity, or methylglyoxal reductase activity.

14. The modified microorganism of claim 13, wherein the enzyme having 3-hydroxypropionaldehyde reductase activity is:

a gene product encoded by a gene selected from the group consisting of yqhD, fucO, dkgA, and dkgB genes from *Escherichia coli*, dhaT gene from *K. pneumoniae*, and ADH1 and ADH2 genes from *Saccharomyces cerevisiae*, or an enzyme having 3-hydroxypropionaldehyde reductase activity obtained by at least one mutation of an enzyme, said mutation improving activity and/or substrate affinity of the enzyme for 3-hydroxypropionaldehyde.

15. The modified microorganism according to claim 1, wherein the production of PDO is enhanced.

16. The modified microorganism according to claim 1, wherein the 2,4-dihydroxybutyrate dehydrogenase, 2-oxo-4-hydroxybutyrate decarboxylase, and/or 3-hydroxypropionaldehyde reductase activities, and/or enzymatic activities allowing the synthesis of DHB are enhanced.

17. The modified microorganism of claim 1, being a bacterium, a yeast, or a fungus.

18. The modified microorganism of claim 1, wherein the expression of:

at least one enzymatic activity selected from the group consisting of phosphoenolpyruvate carboxylase, phosphoenol pyruvate carboxykinase, isocitrate lyase, pyruvate carboxylase, and hexose symporter permease is increased, and/or at least one enzymatic activity selected from the group consisting of lactate dehydrogenase, alcohol dehydrogenase, acetate kinase, phosphate acetyltransferase, pyruvate oxidase, isocitrate lyase, fumarase, 2-oxoglutarate dehydrogenase, pyruvate kinase, malic enzyme, phosphoglucose isomerase, phosphoenolpyruvate carboxylase, phosphoenolpyruvate carboxykinase, pyruvate-formate lyase, succinic semialdehyde dehydrogenase, sugar-transporting phosphotransferase, ketohydroxyglutarate aldolase, homoserine-O-succinyl transferase, homoserine kinase, diaminopimelate decarboxylase, and methylglyoxal synthase is decreased.

19. The modified microorganism according to claim 17, wherein the modified microorganism is *Escherichia coli* that:

overexpresses at least one gene selected from the group consisting of ppc, pck, aceA, galP, asd, thrA, metL, and lysC from *E. coli*, and pycA from *L. lactis*, and/or has at least one deleted gene selected from the group consisting of IdhA, adhE, ackA, pta, poxB, focA, pflB, sad, gabABC, sfcA, maeB, ppc, pykA, pykF, mgsA, sucAB, ptsI, ptsG, pgi, fumABC, aldA, lldD, icIR, metA, thrB, lysA, and eda.

20. A method of production of PDO comprising:

contacting the modified microorganism of claim 1 with a carbon substrate in an appropriate culture medium, and recovering PDO from the culture medium.

21. The method of claim 20, wherein the PDO is further purified.

22. A modified microorganism for producing 1,3-propanediol (PDO) from a carbon substrate, the microorganism comprising:

a pathway for synthesis of 2,4-dihydroxybutyrate (DHB); and a three-step metabolic pathway comprising:
conversion of DHB to obtain 2-oxo-4-hydroxybutyrate (OHB) by an enzyme having DHB dehydrogenase activity,
decarboxylation of the OHB to obtain 3-hydroxypropionaldehyde by an enzyme having 2-oxo-4-hydroxybutyrate decarboxylase activity, and
reduction of the obtained 3-hydroxypropionaldehyde to obtain PDO with an enzyme having 3-hydroxypropionaldehyde reductase activity, wherein:
the gene encoding the enzyme having DHB dehydrogenase activity is selected from the group consisting of IdhA from *Lactococcus lactis*, lldD from *Escherichia coli*, lldD from *E. coli* carrying a mutation at position Val108 (by reference to SEQ ID No. 122), mdh from *E. coli*, mdh from *Bacillus subtilis*, and mdh from *E. coli* carrying a mutation in at least one position selected from the group consisting of (by reference to SEQ ID No. 124): Ile12, Arg81, Lys82, Met85, Asp86, Val93, Ile117, Gly179, Thr211, and Met227 (by reference to SEQ ID No.126);

the gene encoding the enzyme having 2-oxo-4-hydroxybutyrate decarboxylase activity is selected from the group consisting of PDC1, PDC5, PDC6, ARO10, and THI3 genes from *Saccharomyces cerevisiae*; kivD and kdcA genes from *Lactococcus lactis*; pdc gene from *Clostridium acetobutylicum*; PDC2 and PDC3 genes from *Arabidopsis thaliana*; PDC1, PDC2, and ARO10 genes from *Pichia stipitis*; pdc gene from *Zymomonas mobilis*; sucA gene from *Escherichia coli*; dxs gene from *Escherichia coli*; pdc gene from *Z. mobilis* carrying a mutation in at least one position selected from the group consisting of: Tyr290, Trp392, Gly413, and Ile476 (by reference to SEQ ID No.128); and kdcA gene from *L. lactis* carrying a mutation in at least one position selected from the group consisting of: Gln377, Phe381, Phe382, Gly402 Val461, Ile465, and Phe542 (by reference to SEQ ID No.130); and the enzyme having 3-hydroxypropionaldehyde reductase activity is:
a gene product encoded by a gene selected from the group consisting of yqhD, fucO, dkgA, and dkgB genes from *Escherichia coli*, dhaT gene from *K. pneumoniae*, and ADH1 and ADH2 genes from *Saccharomyces cerevisiae*, or
an enzyme having 3-hydroxypropionaldehyde reductase activity obtained by at least one mutation of an enzyme, said mutation improving activity and/or substrate affinity of the enzyme for 3-hydroxypropionaldehyde.

23. The method according to claim 22, wherein:
the enzyme having DHB dehydrogenase activity is Ec-Mdh R81A;

the enzyme having 2-oxo-4-hydroxybutyrate decarboxylase activity is Zm-Pdc; and the enzyme having 3-hydroxypropionaldehyde reductase activity is Ec-YqhD.

\* \* \* \* \*

SEQUENCE LISTING

<160> NUMBER OF SEQ ID NOS: 208

<210> SEQ ID NO 1
<211> LENGTH: 56
<212> TYPE: DNA
<213> ORGANISM: Artificial Sequence
<220> FEATURE:
<223> OTHER INFORMATION: Primer for amplification

<400> SEQUENCE: 1
gaaggttgcg cctacactaa gcatagttgt tgatgagtgt aggctggagc tgcttc        56

<210> SEQ ID NO 2
<211> LENGTH: 56
<212> TYPE: DNA
<213> ORGANISM: Artificial Sequence
<220> FEATURE:
<223> OTHER INFORMATION: Primer for amplification

<400> SEQUENCE: 2
ttaaaccagt tcgttcgggc aggtttcgcc tttttcatgg gaattagcca tggtcc        56

<210> SEQ ID NO 3
<211> LENGTH: 65
<212> TYPE: DNA
<213> ORGANISM: Artificial Sequence
<220> FEATURE:
<223> OTHER INFORMATION: Primer for amplification

<400> SEQUENCE: 3
atggctgtta ctaatgtcgc tgaacttaac gcactcgtag agcgtgtgta ggctggagct    60

```
gcttc                                                             65

<210> SEQ ID NO 4
<211> LENGTH: 65
<212> TYPE: DNA
<213> ORGANISM: Artificial Sequence
<220> FEATURE:
<223> OTHER INFORMATION: Primer for amplification

<400> SEQUENCE: 4
ttaagcggat tttttcgctt ttttctcagc tttagccgga gcagccatat gaatatcctc    60
cttag                                                             65

<210> SEQ ID NO 5
<211> LENGTH: 65
<212> TYPE: DNA
<213> ORGANISM: Artificial Sequence
<220> FEATURE:
<223> OTHER INFORMATION: Primer for amplification

<400> SEQUENCE: 5
atgtcgagta agttagtact ggttctgaac tgcggtagtt cttcagtgta ggctggagct    60
gcttc                                                             65

<210> SEQ ID NO 6
<211> LENGTH: 65
<212> TYPE: DNA
<213> ORGANISM: Artificial Sequence
<220> FEATURE:
<223> OTHER INFORMATION: Primer for amplification

<400> SEQUENCE: 6
tcaggcagtc aggcggctcg cgtcttgcgc gataaccagt tcttccatat gaatatcctc    60
cttag                                                             65

<210> SEQ ID NO 7
<211> LENGTH: 65
<212> TYPE: DNA
<213> ORGANISM: Artificial Sequence
<220> FEATURE:
<223> OTHER INFORMATION: Primer for amplification

<400> SEQUENCE: 7
ttactccgta tttgcataaa aaccatgcga gttacgggcc tataagtgta ggctggagct    60
gcttc                                                             65

<210> SEQ ID NO 8
<211> LENGTH: 65
<212> TYPE: DNA
<213> ORGANISM: Artificial Sequence
<220> FEATURE:
<223> OTHER INFORMATION: Primer for amplification

<400> SEQUENCE: 8
atagattgag tgaaggtacg agtaataacg tcctgctgct gttctcatat gaatatcctc    60
cttag                                                             65

<210> SEQ ID NO 9
<211> LENGTH: 65
<212> TYPE: DNA
<213> ORGANISM: Artificial Sequence
<220> FEATURE:
```

<223> OTHER INFORMATION: Primer for amplification

<400> SEQUENCE: 9
gtgtcccgta ttattatgct gatccctacc ggaaccagcg tcggtgtgta ggctggagct    60
gcttc    65

<210> SEQ ID NO 10
<211> LENGTH: 65
<212> TYPE: DNA
<213> ORGANISM: Artificial Sequence
<220> FEATURE:
<223> OTHER INFORMATION: Primer for amplification

<400> SEQUENCE: 10
ttactgctgc tgtgcagact gaatcgcagt cagcgcgatg gtgtacatat gaatatcctc    60
cttag    65

<210> SEQ ID NO 11
<211> LENGTH: 65
<212> TYPE: DNA
<213> ORGANISM: Artificial Sequence
<220> FEATURE:
<223> OTHER INFORMATION: Primer for amplification

<400> SEQUENCE: 11
atgaaacaaa cggttgcagc ttatatcgcc aaaacactcg aatcggtgta ggctggagct    60
gcttc    65

<210> SEQ ID NO 12
<211> LENGTH: 65
<212> TYPE: DNA
<213> ORGANISM: Artificial Sequence
<220> FEATURE:
<223> OTHER INFORMATION: Primer for amplification

<400> SEQUENCE: 12
ttaccttagc cagtttgttt tcgccagttc gatcacttca tcacccatat gaatatcctc    60
cttag    65

<210> SEQ ID NO 13
<211> LENGTH: 65
<212> TYPE: DNA
<213> ORGANISM: Artificial Sequence
<220> FEATURE:
<223> OTHER INFORMATION: Primer for amplification

<400> SEQUENCE: 13
atgaccatta ctccggcaac tcatgcaatt tcgataaatc ctgccgtgta ggctggagct    60
gcttc    65

<210> SEQ ID NO 14
<211> LENGTH: 65
<212> TYPE: DNA
<213> ORGANISM: Artificial Sequence
<220> FEATURE:
<223> OTHER INFORMATION: Primer for amplification

<400> SEQUENCE: 14
tcagatccgg tctttccaca ccgtctggat attacagaat tcgtgcatat gaatatcctc    60
cttag    65

```
<210> SEQ ID NO 15
<211> LENGTH: 65
<212> TYPE: DNA
<213> ORGANISM: Artificial Sequence
<220> FEATURE:
<223> OTHER INFORMATION: Primer for amplification

<400> SEQUENCE: 15
atgaaactta acgacagtaa cttattccgc cagcaggcgt tgattgtgta ggctggagct    60
gcttc                                                               65

<210> SEQ ID NO 16
<211> LENGTH: 65
<212> TYPE: DNA
<213> ORGANISM: Artificial Sequence
<220> FEATURE:
<223> OTHER INFORMATION: Primer for amplification

<400> SEQUENCE: 16
ttaaagaccg atgcacatat atttgatttc taagtaatct tcgatcatat gaatatcctc    60
cttag                                                               65

<210> SEQ ID NO 17
<211> LENGTH: 65
<212> TYPE: DNA
<213> ORGANISM: Artificial Sequence
<220> FEATURE:
<223> OTHER INFORMATION: Primer for amplification

<400> SEQUENCE: 17
atggaccaga agctgttaac ggatttccgc tcagaactac tcgatgtgta ggctggagct    60
gcttc                                                               65

<210> SEQ ID NO 18
<211> LENGTH: 65
<212> TYPE: DNA
<213> ORGANISM: Artificial Sequence
<220> FEATURE:
<223> OTHER INFORMATION: Primer for amplification

<400> SEQUENCE: 18
tcaggtgtgt ttaaagctgt tctgctgggc aataccctgc agtttcatat gaatatcctc    60
cttag                                                               65

<210> SEQ ID NO 19
<211> LENGTH: 65
<212> TYPE: DNA
<213> ORGANISM: Artificial Sequence
<220> FEATURE:
<223> OTHER INFORMATION: Primer for amplification

<400> SEQUENCE: 19
atggataaga agcaagtaac ggatttaagg tcggaactac tcgatgtgta ggctggagct    60
gcttc                                                               65

<210> SEQ ID NO 20
<211> LENGTH: 65
<212> TYPE: DNA
<213> ORGANISM: Artificial Sequence
<220> FEATURE:
<223> OTHER INFORMATION: Primer for amplification

<400> SEQUENCE: 20
```
tcaggtatgt ttaaagctgt tctgttgggc aataccctgc agtttcatat gaatatcctc    60
cttag                                                                65

<210> SEQ ID NO 21
<211> LENGTH: 65
<212> TYPE: DNA
<213> ORGANISM: Artificial Sequence
<220> FEATURE:
<223> OTHER INFORMATION: Primer for amplification

<400> SEQUENCE: 21
atggctacat cagtacagac aggtaaagct aagcagctca cattagtgta ggctggagct    60
gcttc                                                                65

<210> SEQ ID NO 22
<211> LENGTH: 65
<212> TYPE: DNA
<213> ORGANISM: Artificial Sequence
<220> FEATURE:
<223> OTHER INFORMATION: Primer for amplification

<400> SEQUENCE: 22
ttagtgtttc ttgtcattca tcacaatata gtgtggtgaa cgtgccatat gaatatcctc    60
cttag                                                                65

<210> SEQ ID NO 23
<211> LENGTH: 65
<212> TYPE: DNA
<213> ORGANISM: Artificial Sequence
<220> FEATURE:
<223> OTHER INFORMATION: Primer for amplification

<400> SEQUENCE: 23
atggaaccaa aaacaaaaaa acagcgttcg ctttatatcc cttacgtgta ggctggagct    60
gcttc                                                                65

<210> SEQ ID NO 24
<211> LENGTH: 65
<212> TYPE: DNA
<213> ORGANISM: Artificial Sequence
<220> FEATURE:
<223> OTHER INFORMATION: Primer for amplification

<400> SEQUENCE: 24
ttagatggag gtacggcggt agtcgcggta ttcggcttgc cagaacatat gaatatcctc    60
cttag                                                                65

<210> SEQ ID NO 25
<211> LENGTH: 65
<212> TYPE: DNA
<213> ORGANISM: Artificial Sequence
<220> FEATURE:
<223> OTHER INFORMATION: Primer for amplification

<400> SEQUENCE: 25
atggatgacc agttaaaaca aagtgcactt gatttccatg aatttgtgta ggctggagct    60
gcttc                                                                65

<210> SEQ ID NO 26
<211> LENGTH: 65
<212> TYPE: DNA
<213> ORGANISM: Artificial Sequence

```
<220> FEATURE:
<223> OTHER INFORMATION: Primer for amplification

<400> SEQUENCE: 26
ttacagcggt tgggtttgcg cttctaccac ggccagcgcc accatcatat gaatatcctc    60
cttag                                                                65

<210> SEQ ID NO 27
<211> LENGTH: 65
<212> TYPE: DNA
<213> ORGANISM: Artificial Sequence
<220> FEATURE:
<223> OTHER INFORMATION: Primer for amplification

<400> SEQUENCE: 27
atgtccagaa ggcttcgcag aacaaaaatc gttaccacgt taggcgtgta ggctggagct    60
gcttc                                                                65

<210> SEQ ID NO 28
<211> LENGTH: 65
<212> TYPE: DNA
<213> ORGANISM: Artificial Sequence
<220> FEATURE:
<223> OTHER INFORMATION: Primer for amplification

<400> SEQUENCE: 28
ttactctacc gttaaaatac gcgtggtatt agtagaaccc acggtcatat gaatatcctc    60
cttag                                                                65

<210> SEQ ID NO 29
<211> LENGTH: 65
<212> TYPE: DNA
<213> ORGANISM: Artificial Sequence
<220> FEATURE:
<223> OTHER INFORMATION: Primer for amplification

<400> SEQUENCE: 29
atgaaaaaga ccaaaattgt ttgcaccatc ggaccgaaaa ccgaagtgta ggctggagct    60
gcttc                                                                65

<210> SEQ ID NO 30
<211> LENGTH: 65
<212> TYPE: DNA
<213> ORGANISM: Artificial Sequence
<220> FEATURE:
<223> OTHER INFORMATION: Primer for amplification

<400> SEQUENCE: 30
ttacaggacg tgaacagatg cggtgttagt agtgccgctc ggtaccatat gaatatcctc    60
cttag                                                                65

<210> SEQ ID NO 31
<211> LENGTH: 65
<212> TYPE: DNA
<213> ORGANISM: Artificial Sequence
<220> FEATURE:
<223> OTHER INFORMATION: Primer for amplification

<400> SEQUENCE: 31
atggaactga cgactcgcac tttacctgcg cggaaacata ttgcggtgta ggctggagct    60
gcttc                                                                65
```

<210> SEQ ID NO 32
<211> LENGTH: 65
<212> TYPE: DNA
<213> ORGANISM: Artificial Sequence
<220> FEATURE:
<223> OTHER INFORMATION: Primer for amplification

<400> SEQUENCE: 32
ttacttcaga cggtccgcga gataacgctg ataatcgggg atcagcatat gaatatcctc    60
cttag    65

<210> SEQ ID NO 33
<211> LENGTH: 65
<212> TYPE: DNA
<213> ORGANISM: Artificial Sequence
<220> FEATURE:
<223> OTHER INFORMATION: Primer for amplification

<400> SEQUENCE: 33
atggtcgcac ccattcccgc gaaacgcggc agaaaacccg ccgttgtgta ggctggagct    60
gcttc    65

<210> SEQ ID NO 34
<211> LENGTH: 65
<212> TYPE: DNA
<213> ORGANISM: Artificial Sequence
<220> FEATURE:
<223> OTHER INFORMATION: Primer for amplification

<400> SEQUENCE: 34
tcagcgcatt ccaccgtacg ccagcgtcac ttccttcgcc gctttcatat gaatatcctc    60
cttag    65

<210> SEQ ID NO 35
<211> LENGTH: 65
<212> TYPE: DNA
<213> ORGANISM: Artificial Sequence
<220> FEATURE:
<223> OTHER INFORMATION: Primer for amplification

<400> SEQUENCE: 35
atggaaagta aagtagttgt tccggcacaa ggcaagaaga tcaccgtgta ggctggagct    60
gcttc    65

<210> SEQ ID NO 36
<211> LENGTH: 65
<212> TYPE: DNA
<213> ORGANISM: Artificial Sequence
<220> FEATURE:
<223> OTHER INFORMATION: Primer for amplification

<400> SEQUENCE: 36
ttacatgttt tcgatgatcg cgtcaccaaa ctctgaacat ttcagcatat gaatatcctc    60
cttag    65

<210> SEQ ID NO 37
<211> LENGTH: 65
<212> TYPE: DNA
<213> ORGANISM: Artificial Sequence
<220> FEATURE:
<223> OTHER INFORMATION: Primer for amplification

<400> SEQUENCE: 37
atgcagaaca gcgctttgaa agcctggttg gactcttctt acctcgtgta ggctggagct    60
gcttc    65

<210> SEQ ID NO 38
<211> LENGTH: 65
<212> TYPE: DNA
<213> ORGANISM: Artificial Sequence
<220> FEATURE:
<223> OTHER INFORMATION: Primer for amplification

<400> SEQUENCE: 38
ttattcgacg ttcagcgcgt cattaaccag atcttgttgc tgtttcatat gaatatcctc    60
cttag    65

<210> SEQ ID NO 39
<211> LENGTH: 65
<212> TYPE: DNA
<213> ORGANISM: Artificial Sequence
<220> FEATURE:
<223> OTHER INFORMATION: Primer for amplification

<400> SEQUENCE: 39
atgagtagcg tagatattct ggtccctgac ctgcctgaat ccgtagtgta ggctggagct    60
gcttc    65

<210> SEQ ID NO 40
<211> LENGTH: 65
<212> TYPE: DNA
<213> ORGANISM: Artificial Sequence
<220> FEATURE:
<223> OTHER INFORMATION: Primer for amplification

<400> SEQUENCE: 40
ctacacgtcc agcagcagac gcgtcggatc ttccagcaac tctttcatat gaatatcctc    60
cttag    65

<210> SEQ ID NO 41
<211> LENGTH: 65
<212> TYPE: DNA
<213> ORGANISM: Artificial Sequence
<220> FEATURE:
<223> OTHER INFORMATION: Primer for amplification

<400> SEQUENCE: 41
gtgcaaacct ttcaagccga tcttgccatt gtaggcgccg gtggcgtgta ggctggagct    60
gcttc    65

<210> SEQ ID NO 42
<211> LENGTH: 65
<212> TYPE: DNA
<213> ORGANISM: Artificial Sequence
<220> FEATURE:
<223> OTHER INFORMATION: Primer for amplification

<400> SEQUENCE: 42
tcagccattc gccttctcct tcttattggc tgcttccgcc ttatccatat gaatatcctc    60
cttag    65

<210> SEQ ID NO 43
<211> LENGTH: 65
<212> TYPE: DNA

```
<213> ORGANISM: Artificial Sequence
<220> FEATURE:
<223> OTHER INFORMATION: Primer for amplification

<400> SEQUENCE: 43
atggctgaga tgaaaaacct gaaaattgag gtggtgcgct ataacgtgta ggctggagct    60
gcttc                                                               65

<210> SEQ ID NO 44
<211> LENGTH: 65
<212> TYPE: DNA
<213> ORGANISM: Artificial Sequence
<220> FEATURE:
<223> OTHER INFORMATION: Primer for amplification

<400> SEQUENCE: 44
ttagcgtggt tcagggtcg cgataagaaa gtctttcgaa ctttccatat gaatatcctc    60
cttag                                                               65

<210> SEQ ID NO 45
<211> LENGTH: 65
<212> TYPE: DNA
<213> ORGANISM: Artificial Sequence
<220> FEATURE:
<223> OTHER INFORMATION: Primer for amplification

<400> SEQUENCE: 45
atgacgacta aacgtaaacc gtatgtacgg ccaatgacgt ccaccgtgta ggctggagct    60
gcttc                                                               65

<210> SEQ ID NO 46
<211> LENGTH: 65
<212> TYPE: DNA
<213> ORGANISM: Artificial Sequence
<220> FEATURE:
<223> OTHER INFORMATION: Primer for amplification

<400> SEQUENCE: 46
ttaccagtac agggcaacaa acaggattac gatggtggca accaccatat gaatatcctc    60
cttag                                                               65

<210> SEQ ID NO 47
<211> LENGTH: 65
<212> TYPE: DNA
<213> ORGANISM: Artificial Sequence
<220> FEATURE:
<223> OTHER INFORMATION: Primer for amplification

<400> SEQUENCE: 47
atgattaatc caaatccaaa gcgttctgac gaaccggtat tctgggtgta ggctggagct    60
gcttc                                                               65

<210> SEQ ID NO 48
<211> LENGTH: 65
<212> TYPE: DNA
<213> ORGANISM: Artificial Sequence
<220> FEATURE:
<223> OTHER INFORMATION: Primer for amplification

<400> SEQUENCE: 48
ttagattgta acgacaccaa tcagcgtgac aactgtcagg atagccatat gaatatcctc    60
cttag                                                               65
```

<210> SEQ ID NO 49
<211> LENGTH: 65
<212> TYPE: DNA
<213> ORGANISM: Artificial Sequence
<220> FEATURE:
<223> OTHER INFORMATION: Primer for amplification

<400> SEQUENCE: 49
atgatttcag gcattttagc atccccgggt atcgctttcg gtaaagtgta ggctggagct    60
gcttc                                                               65

<210> SEQ ID NO 50
<211> LENGTH: 65
<212> TYPE: DNA
<213> ORGANISM: Artificial Sequence
<220> FEATURE:
<223> OTHER INFORMATION: Primer for amplification

<400> SEQUENCE: 50
ttagcagatt gttttttctt caatgaactt gttaaccagc gtcatcatat gaatatcctc    60
cttag                                                               65

<210> SEQ ID NO 51
<211> LENGTH: 65
<212> TYPE: DNA
<213> ORGANISM: Artificial Sequence
<220> FEATURE:
<223> OTHER INFORMATION: Primer for amplification

<400> SEQUENCE: 51
atgtttaaga atgcatttgc taacctgcaa aaggtcggta aatcggtgta ggctggagct    60
gcttc                                                               65

<210> SEQ ID NO 52
<211> LENGTH: 65
<212> TYPE: DNA
<213> ORGANISM: Artificial Sequence
<220> FEATURE:
<223> OTHER INFORMATION: Primer for amplification

<400> SEQUENCE: 52
ttagtggtta cggatgtact catccatctc ggttttcagg ttatccatat gaatatcctc    60
cttag                                                               65

<210> SEQ ID NO 53
<211> LENGTH: 65
<212> TYPE: DNA
<213> ORGANISM: Artificial Sequence
<220> FEATURE:
<223> OTHER INFORMATION: Primer for amplification

<400> SEQUENCE: 53
gtgaaaccag taacgttata cgatgtcgca gagtatgccg gtgtcgtgta ggctggagct    60
gcttc                                                               65

<210> SEQ ID NO 54
<211> LENGTH: 65
<212> TYPE: DNA
<213> ORGANISM: Artificial Sequence
<220> FEATURE:
<223> OTHER INFORMATION: Primer for amplification

<400> SEQUENCE: 54
tcactgcccg ctttccagtc gggaaacctg tcgtgccagc tgcatcatat gaatatcctc    60
cttag    65

<210> SEQ ID NO 55
<211> LENGTH: 65
<212> TYPE: DNA
<213> ORGANISM: Artificial Sequence
<220> FEATURE:
<223> OTHER INFORMATION: Primer for amplification

<400> SEQUENCE: 55
atgaaaaaca tcaatccaac gcagaccgct gcctggcagg cactagtgta ggctggagct    60
gcttc    65

<210> SEQ ID NO 56
<211> LENGTH: 65
<212> TYPE: DNA
<213> ORGANISM: Artificial Sequence
<220> FEATURE:
<223> OTHER INFORMATION: Primer for amplification

<400> SEQUENCE: 56
ttaaccgcgc cacgctttat agcggttaat cagaccattg gtcgacatat gaatatcctc    60
cttag    65

<210> SEQ ID NO 57
<211> LENGTH: 65
<212> TYPE: DNA
<213> ORGANISM: Artificial Sequence
<220> FEATURE:
<223> OTHER INFORMATION: Primer for amplification

<400> SEQUENCE: 57
atgaaaaact ggaaaacaag tgcagaatca atcctgacca ccggcgtgta ggctggagct    60
gcttc    65

<210> SEQ ID NO 58
<211> LENGTH: 65
<212> TYPE: DNA
<213> ORGANISM: Artificial Sequence
<220> FEATURE:
<223> OTHER INFORMATION: Primer for amplification

<400> SEQUENCE: 58
ctcgatcggg cattttgact tttacagctt agcgccttct acagccatat gaatatcctc    60
cttag    65

<210> SEQ ID NO 59
<211> LENGTH: 20
<212> TYPE: DNA
<213> ORGANISM: Artificial Sequence
<220> FEATURE:
<223> OTHER INFORMATION: Primer for amplification

<400> SEQUENCE: 59
cggtgccctg aatgaactgc    20

<210> SEQ ID NO 60
<211> LENGTH: 20
<212> TYPE: DNA
<213> ORGANISM: Artificial Sequence

```
<220> FEATURE:
<223> OTHER INFORMATION: Primer for amplification

<400> SEQUENCE: 60
cagtcatagc cgaatagcct                                                 20

<210> SEQ ID NO 61
<211> LENGTH: 20
<212> TYPE: DNA
<213> ORGANISM: Artificial Sequence
<220> FEATURE:
<223> OTHER INFORMATION: Primer for amplification

<400> SEQUENCE: 61
atacgtgtcc cgagcggtag                                                 20

<210> SEQ ID NO 62
<211> LENGTH: 20
<212> TYPE: DNA
<213> ORGANISM: Artificial Sequence
<220> FEATURE:
<223> OTHER INFORMATION: Primer for amplification

<400> SEQUENCE: 62
tacacatccc gccatcagca                                                 20

<210> SEQ ID NO 63
<211> LENGTH: 20
<212> TYPE: DNA
<213> ORGANISM: Artificial Sequence
<220> FEATURE:
<223> OTHER INFORMATION: Primer for amplification

<400> SEQUENCE: 63
gaagtaaacg ggaaaatcaa                                                 20

<210> SEQ ID NO 64
<211> LENGTH: 20
<212> TYPE: DNA
<213> ORGANISM: Artificial Sequence
<220> FEATURE:
<223> OTHER INFORMATION: Primer for amplification

<400> SEQUENCE: 64
agaagtggca taagaaaacg                                                 20

<210> SEQ ID NO 65
<211> LENGTH: 20
<212> TYPE: DNA
<213> ORGANISM: Artificial Sequence
<220> FEATURE:
<223> OTHER INFORMATION: Primer for amplification

<400> SEQUENCE: 65
ccattggctg aaaattacgc                                                 20

<210> SEQ ID NO 66
<211> LENGTH: 20
<212> TYPE: DNA
<213> ORGANISM: Artificial Sequence
<220> FEATURE:
<223> OTHER INFORMATION: Primer for amplification

<400> SEQUENCE: 66
gttccattgc acggatcacg                                                 20
```

<210> SEQ ID NO 67
<211> LENGTH: 20
<212> TYPE: DNA
<213> ORGANISM: Artificial Sequence
<220> FEATURE:
<223> OTHER INFORMATION: Primer for amplification

<400> SEQUENCE: 67
atgccgtaga agccgccagt                                               20

<210> SEQ ID NO 68
<211> LENGTH: 20
<212> TYPE: DNA
<213> ORGANISM: Artificial Sequence
<220> FEATURE:
<223> OTHER INFORMATION: Primer for amplification

<400> SEQUENCE: 68
tgttggtgcg cagctcgaag                                               20

<210> SEQ ID NO 69
<211> LENGTH: 20
<212> TYPE: DNA
<213> ORGANISM: Artificial Sequence
<220> FEATURE:
<223> OTHER INFORMATION: Primer for amplification

<400> SEQUENCE: 69
gcaaatctgg tttcatcaac                                               20

<210> SEQ ID NO 70
<211> LENGTH: 20
<212> TYPE: DNA
<213> ORGANISM: Artificial Sequence
<220> FEATURE:
<223> OTHER INFORMATION: Primer for amplification

<400> SEQUENCE: 70
tcccttgcac aaaacaaagt                                               20

<210> SEQ ID NO 71
<211> LENGTH: 20
<212> TYPE: DNA
<213> ORGANISM: Artificial Sequence
<220> FEATURE:
<223> OTHER INFORMATION: Primer for amplification

<400> SEQUENCE: 71
ggatttggtt ctcgcataat                                               20

<210> SEQ ID NO 72
<211> LENGTH: 20
<212> TYPE: DNA
<213> ORGANISM: Artificial Sequence
<220> FEATURE:
<223> OTHER INFORMATION: Primer for amplification

<400> SEQUENCE: 72
agcattaacg gtagggtcgt                                               20

<210> SEQ ID NO 73
<211> LENGTH: 20
<212> TYPE: DNA
<213> ORGANISM: Artificial Sequence
<220> FEATURE:
<223> OTHER INFORMATION: Primer for amplification

<400> SEQUENCE: 73
gctgattctc gcgaataaac                                              20

<210> SEQ ID NO 74
<211> LENGTH: 20
<212> TYPE: DNA
<213> ORGANISM: Artificial Sequence
<220> FEATURE:
<223> OTHER INFORMATION: Primer for amplification

<400> SEQUENCE: 74
aaaaacgttc ttgcgcgtct                                              20

<210> SEQ ID NO 75
<211> LENGTH: 20
<212> TYPE: DNA
<213> ORGANISM: Artificial Sequence
<220> FEATURE:
<223> OTHER INFORMATION: Primer for amplification

<400> SEQUENCE: 75
tctgtttgtc accaccccgc                                              20

<210> SEQ ID NO 76
<211> LENGTH: 20
<212> TYPE: DNA
<213> ORGANISM: Artificial Sequence
<220> FEATURE:
<223> OTHER INFORMATION: Primer for amplification

<400> SEQUENCE: 76
aagccagcac ctggaagcag                                              20

<210> SEQ ID NO 77
<211> LENGTH: 20
<212> TYPE: DNA
<213> ORGANISM: Artificial Sequence
<220> FEATURE:
<223> OTHER INFORMATION: Primer for amplification

<400> SEQUENCE: 77
aagagctgcc gcaggaggat                                              20

<210> SEQ ID NO 78
<211> LENGTH: 20
<212> TYPE: DNA
<213> ORGANISM: Artificial Sequence
<220> FEATURE:
<223> OTHER INFORMATION: Primer for amplification

<400> SEQUENCE: 78
gccgccctct taagtcaaat                                              20

<210> SEQ ID NO 79
<211> LENGTH: 20
<212> TYPE: DNA
<213> ORGANISM: Artificial Sequence
<220> FEATURE:
<223> OTHER INFORMATION: Primer for amplification

<400> SEQUENCE: 79
ggattttagc aatattcgct                                              20

<210> SEQ ID NO 80

```
<211> LENGTH: 20
<212> TYPE: DNA
<213> ORGANISM: Artificial Sequence
<220> FEATURE:
<223> OTHER INFORMATION: Primer for amplification

<400> SEQUENCE: 80
cctaatagca ggaagaagac                                             20

<210> SEQ ID NO 81
<211> LENGTH: 20
<212> TYPE: DNA
<213> ORGANISM: Artificial Sequence
<220> FEATURE:
<223> OTHER INFORMATION: Primer for amplification

<400> SEQUENCE: 81
gctgaactgt tgctggaaga                                             20

<210> SEQ ID NO 82
<211> LENGTH: 20
<212> TYPE: DNA
<213> ORGANISM: Artificial Sequence
<220> FEATURE:
<223> OTHER INFORMATION: Primer for amplification

<400> SEQUENCE: 82
ggcgtgcttt tacaactaca                                             20

<210> SEQ ID NO 83
<211> LENGTH: 20
<212> TYPE: DNA
<213> ORGANISM: Artificial Sequence
<220> FEATURE:
<223> OTHER INFORMATION: Primer for amplification

<400> SEQUENCE: 83
tagtaaataa cccaaccggc                                             20

<210> SEQ ID NO 84
<211> LENGTH: 20
<212> TYPE: DNA
<213> ORGANISM: Artificial Sequence
<220> FEATURE:
<223> OTHER INFORMATION: Primer for amplification

<400> SEQUENCE: 84
tcagtgagcg cagtgtttta                                             20

<210> SEQ ID NO 85
<211> LENGTH: 20
<212> TYPE: DNA
<213> ORGANISM: Artificial Sequence
<220> FEATURE:
<223> OTHER INFORMATION: Primer for amplification

<400> SEQUENCE: 85
attaatggtg agagtttgga                                             20

<210> SEQ ID NO 86
<211> LENGTH: 20
<212> TYPE: DNA
<213> ORGANISM: Artificial Sequence
<220> FEATURE:
<223> OTHER INFORMATION: Primer for amplification

<400> SEQUENCE: 86
```
tgcttttttt tattattcgc                                              20

<210> SEQ ID NO 87
<211> LENGTH: 20
<212> TYPE: DNA
<213> ORGANISM: Artificial Sequence
<220> FEATURE:
<223> OTHER INFORMATION: Primer for amplification

<400> SEQUENCE: 87
tttatatgcc catggtttct                                              20

<210> SEQ ID NO 88
<211> LENGTH: 20
<212> TYPE: DNA
<213> ORGANISM: Artificial Sequence
<220> FEATURE:
<223> OTHER INFORMATION: Primer for amplification

<400> SEQUENCE: 88
atctgttaga ggcggatgat                                              20

<210> SEQ ID NO 89
<211> LENGTH: 20
<212> TYPE: DNA
<213> ORGANISM: Artificial Sequence
<220> FEATURE:
<223> OTHER INFORMATION: Primer for amplification

<400> SEQUENCE: 89
ctggaacgtt aaatctttga                                              20

<210> SEQ ID NO 90
<211> LENGTH: 20
<212> TYPE: DNA
<213> ORGANISM: Artificial Sequence
<220> FEATURE:
<223> OTHER INFORMATION: Primer for amplification

<400> SEQUENCE: 90
ccagtttagt agctttcatt                                              20

<210> SEQ ID NO 91
<211> LENGTH: 25
<212> TYPE: DNA
<213> ORGANISM: Artificial Sequence
<220> FEATURE:
<223> OTHER INFORMATION: Primer for amplification

<400> SEQUENCE: 91
gatttgttca acattaactc atcgg                                        25

<210> SEQ ID NO 92
<211> LENGTH: 20
<212> TYPE: DNA
<213> ORGANISM: Artificial Sequence
<220> FEATURE:
<223> OTHER INFORMATION: Primer for amplification

<400> SEQUENCE: 92
tgcgattaac agacaccctt                                              20

<210> SEQ ID NO 93
<211> LENGTH: 20
<212> TYPE: DNA

<213> ORGANISM: Artificial Sequence
<220> FEATURE:
<223> OTHER INFORMATION: Primer for amplification

<400> SEQUENCE: 93
tctcaggtgc tcacagaaca                                               20

<210> SEQ ID NO 94
<211> LENGTH: 20
<212> TYPE: DNA
<213> ORGANISM: Artificial Sequence
<220> FEATURE:
<223> OTHER INFORMATION: Primer for amplification

<400> SEQUENCE: 94
tatggaagag gcgctactgc                                               20

<210> SEQ ID NO 95
<211> LENGTH: 20
<212> TYPE: DNA
<213> ORGANISM: Artificial Sequence
<220> FEATURE:
<223> OTHER INFORMATION: Primer for amplification

<400> SEQUENCE: 95
cgacctgctg cataaacacc                                               20

<210> SEQ ID NO 96
<211> LENGTH: 20
<212> TYPE: DNA
<213> ORGANISM: Artificial Sequence
<220> FEATURE:
<223> OTHER INFORMATION: Primer for amplification

<400> SEQUENCE: 96
tgaacgctaa ggtgattgca                                               20

<210> SEQ ID NO 97
<211> LENGTH: 20
<212> TYPE: DNA
<213> ORGANISM: Artificial Sequence
<220> FEATURE:
<223> OTHER INFORMATION: Primer for amplification

<400> SEQUENCE: 97
acgtagacaa gagctcgcaa                                               20

<210> SEQ ID NO 98
<211> LENGTH: 20
<212> TYPE: DNA
<213> ORGANISM: Artificial Sequence
<220> FEATURE:
<223> OTHER INFORMATION: Primer for amplification

<400> SEQUENCE: 98
catcacgtac gactgcgtcg                                               20

<210> SEQ ID NO 99
<211> LENGTH: 19
<212> TYPE: DNA
<213> ORGANISM: Artificial Sequence
<220> FEATURE:
<223> OTHER INFORMATION: Primer for amplification

<400> SEQUENCE: 99
tgcaactttg tgctgagca                                                19

<210> SEQ ID NO 100
<211> LENGTH: 20
<212> TYPE: DNA
<213> ORGANISM: Artificial Sequence
<220> FEATURE:
<223> OTHER INFORMATION: Primer for amplification

<400> SEQUENCE: 100
tatcgcttcc gggcattgtc                                               20

<210> SEQ ID NO 101
<211> LENGTH: 25
<212> TYPE: DNA
<213> ORGANISM: Artificial Sequence
<220> FEATURE:
<223> OTHER INFORMATION: Primer for amplification

<400> SEQUENCE: 101
aaatcgatct cgtcaaattt cagac                                         25

<210> SEQ ID NO 102
<211> LENGTH: 20
<212> TYPE: DNA
<213> ORGANISM: Artificial Sequence
<220> FEATURE:
<223> OTHER INFORMATION: Primer for amplification

<400> SEQUENCE: 102
aggaaccaca aatcgccata                                               20

<210> SEQ ID NO 103
<211> LENGTH: 20
<212> TYPE: DNA
<213> ORGANISM: Artificial Sequence
<220> FEATURE:
<223> OTHER INFORMATION: Primer for amplification

<400> SEQUENCE: 103
gacgtgaaga ttactacgct                                               20

<210> SEQ ID NO 104
<211> LENGTH: 20
<212> TYPE: DNA
<213> ORGANISM: Artificial Sequence
<220> FEATURE:
<223> OTHER INFORMATION: Primer for amplification

<400> SEQUENCE: 104
agttcaatgc tgaaccacac                                               20

<210> SEQ ID NO 105
<211> LENGTH: 25
<212> TYPE: DNA
<213> ORGANISM: Artificial Sequence
<220> FEATURE:
<223> OTHER INFORMATION: Primer for amplification

<400> SEQUENCE: 105
tagccgcgac cacggtaaga aggag                                         25

<210> SEQ ID NO 106
<211> LENGTH: 20
<212> TYPE: DNA
<213> ORGANISM: Artificial Sequence
<220> FEATURE:

<223> OTHER INFORMATION: Primer for amplification

<400> SEQUENCE: 106
cagcgcatca cccggaaaca                                                      20

<210> SEQ ID NO 107
<211> LENGTH: 20
<212> TYPE: DNA
<213> ORGANISM: Artificial Sequence
<220> FEATURE:
<223> OTHER INFORMATION: Primer for amplification

<400> SEQUENCE: 107
atcgtgatca ttaacctgat                                                      20

<210> SEQ ID NO 108
<211> LENGTH: 20
<212> TYPE: DNA
<213> ORGANISM: Artificial Sequence
<220> FEATURE:
<223> OTHER INFORMATION: Primer for amplification

<400> SEQUENCE: 108
ttaccctgat aaattaccgc                                                      20

<210> SEQ ID NO 109
<211> LENGTH: 20
<212> TYPE: DNA
<213> ORGANISM: Artificial Sequence
<220> FEATURE:
<223> OTHER INFORMATION: Primer for amplification

<400> SEQUENCE: 109
gaatctggtg tatatggcga                                                      20

<210> SEQ ID NO 110
<211> LENGTH: 20
<212> TYPE: DNA
<213> ORGANISM: Artificial Sequence
<220> FEATURE:
<223> OTHER INFORMATION: Primer for amplification

<400> SEQUENCE: 110
tcttcgctat tacgccagct                                                      20

<210> SEQ ID NO 111
<211> LENGTH: 20
<212> TYPE: DNA
<213> ORGANISM: Artificial Sequence
<220> FEATURE:
<223> OTHER INFORMATION: Primer for amplification

<400> SEQUENCE: 111
ttgtcaacga tggggtcatg                                                      20

<210> SEQ ID NO 112
<211> LENGTH: 20
<212> TYPE: DNA
<213> ORGANISM: Artificial Sequence
<220> FEATURE:
<223> OTHER INFORMATION: Primer for amplification

<400> SEQUENCE: 112
aaaaatgccg acataacgtc                                                      20

<210> SEQ ID NO 113
<211> LENGTH: 20
<212> TYPE: DNA
<213> ORGANISM: Artificial Sequence
<220> FEATURE:
<223> OTHER INFORMATION: Primer for amplification

<400> SEQUENCE: 113
ccatccgttg aatgagtttt                                              20

<210> SEQ ID NO 114
<211> LENGTH: 20
<212> TYPE: DNA
<213> ORGANISM: Artificial Sequence
<220> FEATURE:
<223> OTHER INFORMATION: Primer for amplification

<400> SEQUENCE: 114
tggtgttaac tggcaaaatc                                              20

<210> SEQ ID NO 115
<211> LENGTH: 20
<212> TYPE: DNA
<213> ORGANISM: Artificial Sequence
<220> FEATURE:
<223> OTHER INFORMATION: Primer for amplification

<400> SEQUENCE: 115
gtgacttcca acggcaaaag                                              20

<210> SEQ ID NO 116
<211> LENGTH: 20
<212> TYPE: DNA
<213> ORGANISM: Artificial Sequence
<220> FEATURE:
<223> OTHER INFORMATION: Primer for amplification

<400> SEQUENCE: 116
ccgttggttt gatagcaata                                              20

<210> SEQ ID NO 117
<211> LENGTH: 20
<212> TYPE: DNA
<213> ORGANISM: Artificial Sequence
<220> FEATURE:
<223> OTHER INFORMATION: Primer for amplification

<400> SEQUENCE: 117
gacagacagg cgaactgacg                                              20

<210> SEQ ID NO 118
<211> LENGTH: 20
<212> TYPE: DNA
<213> ORGANISM: Artificial Sequence
<220> FEATURE:
<223> OTHER INFORMATION: Primer for amplification

<400> SEQUENCE: 118
gcgcagattt gcagattcgt                                              20

<210> SEQ ID NO 119
<211> LENGTH: 978
<212> TYPE: DNA
<213> ORGANISM: Lactococcus lactis

<400> SEQUENCE: 119

```
atggctgata acaacgtaa aaaagttatc cttgtaggtg acggtgctgt aggttcatca    60
tacgctttg ctcttgtaaa ccaagggatt gcacaagaat taggaattgt tgaccttttt   120
aaagaaaaaa ctcaaggaga tgcagaagac ctttctcatg ccttggcatt tacttcacct   180
aaaaagattt actctgcaga ctactctgat gcaagcgacg ctgacctcgt agtcttgact   240
tctggtgctc cacaaaaacc aggtgaaact cgtcttgacc ttgttgaaaa aaatcttcgt   300
atcactaaag atgttgtcac taaaattgtt gcttcaggtt tcaaaggaat cttccttgtt   360
gctgctaacc cagttgatat cttgacatac gctacttgga aattctcagg tttccctaaa   420
aaccgcgttg taggttcagg tacttcactt gatactgcac gtttccgtca agcattggca   480
gaaaaagttg atgttgacgc tcgttcaatc cacgcataca tcatgggtga acacggtgac   540
tcagaatttg ccgtttggtc acacgctaac gttgctggtg ttaaattgga acaatggttc   600
caagaaaatg actaccttaa cgaagctgaa atcgttgaat gtttgaatc tgtacgtgat   660
gctgcttact caatcatcgc taaaaaaggt gcaacattct atggtgtcgc tgtagctctt   720
gctcgtatta ctaaagcaat tcttgatgat gaacatgcag tacttccagt atcagtattc   780
caagatggac aatatggcgt aagcgactgc taccttggtc aaccagctgt agttggtgct   840
gaaggtgttg ttaaccccaat ccacattcca ttgaatgatg ctgaaatgca aaaaatggaa   900
gcttctggtg ctcaattgaa agcaatcatt gacgaagctt tgctaaaga gaatttgct   960
tctgcagtta aaaactaa                                                 978
```

<210> SEQ ID NO 120
<211> LENGTH: 325
<212> TYPE: PRT
<213> ORGANISM: Lactococcus lactis

<400> SEQUENCE: 120

```
Met Ala Asp Lys Gln Arg Lys Lys Val Ile Leu Val Gly Asp Gly Ala
1               5                   10                  15
Val Gly Ser Ser Tyr Ala Phe Ala Leu Val Asn Gln Gly Ile Ala Gln
                20                  25                  30
Glu Leu Gly Ile Val Asp Leu Phe Lys Glu Lys Thr Gln Gly Asp Ala
            35                  40                  45
Glu Asp Leu Ser His Ala Leu Ala Phe Thr Ser Pro Lys Lys Ile Tyr
        50                  55                  60
Ser Ala Asp Tyr Ser Asp Ala Ser Asp Ala Asp Leu Val Val Leu Thr
65                  70                  75                  80
Ser Gly Ala Pro Gln Lys Pro Gly Glu Thr Arg Leu Asp Leu Val Glu
                85                  90                  95
Lys Asn Leu Arg Ile Thr Lys Asp Val Val Thr Lys Ile Val Ala Ser
                100                 105                 110
Gly Phe Lys Gly Ile Phe Leu Val Ala Ala Asn Pro Val Asp Ile Leu
            115                 120                 125
Thr Tyr Ala Thr Trp Lys Phe Ser Gly Phe Pro Lys Asn Arg Val Val
        130                 135                 140
Gly Ser Gly Thr Ser Leu Asp Thr Ala Arg Phe Arg Gln Ala Leu Ala
145                 150                 155                 160
Glu Lys Val Asp Val Asp Ala Arg Ser Ile His Ala Tyr Ile Met Gly
                165                 170                 175
Glu His Gly Asp Ser Glu Phe Ala Val Trp Ser His Ala Asn Val Ala
            180                 185                 190
Gly Val Lys Leu Glu Gln Trp Phe Gln Glu Asn Asp Tyr Leu Asn Glu
```

```
              195                 200                 205
Ala Glu Ile Val Glu Leu Phe Glu Ser Val Arg Asp Ala Ala Tyr Ser
    210                 215                 220

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
                245                 250                 255

Val Ser Val Phe Gln Asp Gly Gln Tyr Gly Val Ser Asp Cys Tyr Leu
            260                 265                 270

Gly Gln Pro Ala Val Val Gly Ala Glu Gly Val Val Asn Pro Ile His
        275                 280                 285

Ile Pro Leu Asn Asp Ala Glu Met Gln Lys Met Glu Ala Ser Gly Ala
    290                 295                 300

Gln Leu Lys Ala Ile Ile Asp Glu Ala Phe Ala Lys Glu Glu Phe Ala
305                 310                 315                 320

Ser Ala Val Lys Asn
            325

<210> SEQ ID NO 121
<211> LENGTH: 1191
<212> TYPE: DNA
<213> ORGANISM: Escherichia coli

<400> SEQUENCE: 121
atgattattt ccgcagccag cgattatcgc gccgcagcgc aacgcattct gccgccgttc      60
ctgttccact atatggatgg tgtgcatat tctgaataca cgctgcgccg caacgtggaa     120
gatttgtcag aagtggcgct gcgccagcgt attctgaaaa acatgtccga cttaagcctg     180
gaaacgacgc tgtttaatga aaattgtcg atgccggtgg cactggctcc ggtgggtttg     240
tgtggcatgt atgcgcgtcg tggcgaagtt caggcagcca aagcggcgga cgcgcatggt     300
attccgttta ctctctcgac ggtttccgtt tgcccgattg aagaagtcgc gccagccatc     360
aagcgcccaa tgtggttcca gctttatgta ctgcgcgatc gcggctttat gcgtaacgcg     420
ctggagcgag caaaagcagc gggttgttcg acgctggttt tcaccgtgga tatgccgaca     480
ccgggcgcac gctaccgtga tgcgcattca ggtatgagcg cccgaacgc ggcaatgcgc     540
cgctacttgc aagcggtgac acatccgcaa tgggcgtggg atgtgggcct gaacggtcgt     600
ccacatgatt taggtaatat ctcagcttat ctcggcaaac cgaccggact ggaagattac     660
atcggctggc tggggaataa cttcgatccg tccatctcat ggaaagacct tgaatggatc     720
cgcgatttct gggatggccc gatggtgatc aaagggatcc tcgatccgga agatgcgcgc     780
gatgcagtac gttttggtgc tgatggaatt gtggtttcta accacggtgg ccgccagctg     840
gacggtgtac tctcttccgc ccgtgcactg cctgctattg cagatgcggt gaaaggtgat     900
atagccattc tggcggatag cggaattcgt aacgggcttg atgtcgtgcg tatgattgcg     960
ctcggtgccg acaccgtact gctgggtcgt gctttcttgt atgcgctggc aacagcgggc    1020
caggcgggtg tagctaacct gctaaatctg atcgaaaaag agatgaaagt ggcgatgacg    1080
ctgactggcg cgaaatcgat cagcgaaatt acgcaagatt cgctggtgca ggggctgggt    1140
aaagagttgc ctgcggcact ggctcccatg gcgaaaggga atgcggcata g              1191

<210> SEQ ID NO 122
<211> LENGTH: 396
<212> TYPE: PRT
<213> ORGANISM: Escherichia coli
```

<400> SEQUENCE: 122

Met Ile Ile Ser Ala Ala Ser Asp Tyr Arg Ala Ala Gln Arg Ile
1               5                   10                  15

Leu Pro Pro Phe Leu Phe His Tyr Met Asp Gly Gly Ala Tyr Ser Glu
            20                  25                  30

Tyr Thr Leu Arg Arg Asn Val Glu Asp Leu Ser Glu Val Ala Leu Arg
            35                  40                  45

Gln Arg Ile Leu Lys Asn Met Ser Asp Leu Ser Leu Glu Thr Thr Leu
50                      55                  60

Phe Asn Glu Lys Leu Ser Met Pro Val Ala Leu Ala Pro Val Gly Leu
65                  70                  75                  80

Cys Gly Met Tyr Ala Arg Arg Gly Glu Val Gln Ala Ala Lys Ala Ala
                85                  90                  95

Asp Ala His Gly Ile Pro Phe Thr Leu Ser Thr Val Ser Val Cys Pro
                100                 105                 110

Ile Glu Glu Val Ala Pro Ala Ile Lys Arg Pro Met Trp Phe Gln Leu
            115                 120                 125

Tyr Val Leu Arg Asp Arg Gly Phe Met Arg Asn Ala Leu Glu Arg Ala
130                     135                 140

Lys Ala Ala Gly Cys Ser Thr Leu Val Phe Thr Val Asp Met Pro Thr
145                 150                 155                 160

Pro Gly Ala Arg Tyr Arg Asp Ala His Ser Gly Met Ser Gly Pro Asn
                165                 170                 175

Ala Ala Met Arg Arg Tyr Leu Gln Ala Val Thr His Pro Gln Trp Ala
            180                 185                 190

Trp Asp Val Gly Leu Asn Gly Arg Pro His Asp Leu Gly Asn Ile Ser
        195                 200                 205

Ala Tyr Leu Gly Lys Pro Thr Gly Leu Glu Asp Tyr Ile Gly Trp Leu
210                 215                 220

Gly Asn Asn Phe Asp Pro Ser Ile Ser Trp Lys Asp Leu Glu Trp Ile
225                 230                 235                 240

Arg Asp Phe Trp Asp Gly Pro Met Val Ile Lys Gly Ile Leu Asp Pro
                245                 250                 255

Glu Asp Ala Arg Asp Ala Val Arg Phe Gly Ala Asp Gly Ile Val Val
                260                 265                 270

Ser Asn His Gly Gly Arg Gln Leu Asp Gly Val Leu Ser Ser Ala Arg
            275                 280                 285

Ala Leu Pro Ala Ile Ala Asp Ala Val Lys Gly Asp Ile Ala Ile Leu
            290                 295                 300

Ala Asp Ser Gly Ile Arg Asn Gly Leu Asp Val Val Arg Met Ile Ala
305                 310                 315                 320

Leu Gly Ala Asp Thr Val Leu Leu Gly Arg Ala Phe Leu Tyr Ala Leu
                325                 330                 335

Ala Thr Ala Gly Gln Ala Gly Val Ala Asn Leu Leu Asn Leu Ile Glu
            340                 345                 350

Lys Glu Met Lys Val Ala Met Thr Leu Thr Gly Ala Lys Ser Ile Ser
            355                 360                 365

Glu Ile Thr Gln Asp Ser Leu Val Gln Gly Leu Gly Lys Glu Leu Pro
            370                 375                 380

Ala Ala Leu Ala Pro Met Ala Lys Gly Asn Ala Ala
385                 390                 395

<210> SEQ ID NO 123
<211> LENGTH: 939
<212> TYPE: DNA
<213> ORGANISM: Escherichia coli

<400> SEQUENCE: 123

```
atgaaagtcg cagtcctcgg cgctgctggc ggtattggcc aggcgcttgc actactgtta    60
aaaacccaac tgccttcagg ttcagaactc tctctgtatg atatcgctcc agtgactccc   120
ggtgtggctg tcgatctgag ccatatccct actgctgtga aaatcaaagg tttttctggt   180
gaagatgcga ctccggcgct ggaaggcgca gatgtcgttc ttatctctgc aggcgtagcg   240
cgtaaaccgg gtatggatcg ttccgacctg tttaacgtta acgccggcat cgtgaaaaac   300
ctggtacagc aagttgcgaa aacctgcccg aaagcgtgca ttggtattat cactaacccg   360
gttaacacca cagttgcaat tgctgctgaa gtgctgaaaa agccggtgt ttatgacaaa    420
aacaaactgt tcggcgttac cacgctggat atcattcgtt ccaacacctt tgttgcggaa   480
ctgaaaggca acagccagg cgaagttgaa gtgccggtta ttggcggtca ctctggtgtt    540
accattctgc cgctgctgtc acaggttcct ggcgttagtt ttaccgagca ggaagtggct   600
gatctgacca aacgcatcca gaacgcgggt accgaagtgg ttgaagcgaa ggccggtggc   660
gggtctgcaa ccctgtctat gggccaggca gctgcacgtt ttggtctgtc tctggttcgt   720
gcactgcagg gcgaacaagg cgttgtcgaa tgtgcctacg ttgaaggcga cggtcagtac   780
gcccgttttct tctctcaacc gctgctgctg ggtaaaaacg gcgtggaaga gcgtaaatct   840
atcggtaccc tgagcgcatt tgaacagaac gcgctggaag gtatgctgga tacgctgaag   900
aaagatatcg ccctgggcga agagttcgtt aataagtaa                         939
```

<210> SEQ ID NO 124
<211> LENGTH: 312
<212> TYPE: PRT
<213> ORGANISM: Escherichia coli

<400> SEQUENCE: 124

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
                20                  25                  30

Tyr Asp Ile Ala Pro Val Thr Pro Gly Val Ala Val Asp Leu Ser His
            35                  40                  45

Ile Pro Thr Ala Val Lys Ile Lys Gly Phe Ser Gly Glu Asp Ala Thr
        50                  55                  60

Pro Ala Leu Glu Gly Ala Asp Val Val Leu Ile Ser Ala Gly Val Ala
65                  70                  75                  80

Arg Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175
```

His Ser Gly Val Thr Ile Leu Pro Leu Leu Ser Gln Val Pro Gly Val
            180                 185                 190
Ser Phe Thr Glu Gln Glu Val Ala Asp Leu Thr Lys Arg Ile Gln Asn
        195                 200                 205
Ala Gly Thr Glu Val Val Glu Ala Lys Ala Gly Gly Ser Ala Thr
    210                 215                 220
Leu Ser Met Gly Gln Ala Ala Ala Arg Phe Gly Leu Ser Leu Val Arg
225                 230                 235                 240
Ala Leu Gln Gly Glu Gln Gly Val Val Glu Cys Ala Tyr Val Glu Gly
                245                 250                 255
Asp Gly Gln Tyr Ala Arg Phe Phe Ser Gln Pro Leu Leu Leu Gly Lys
            260                 265                 270
Asn Gly Val Glu Glu Arg Lys Ser Ile Gly Thr Leu Ser Ala Phe Glu
        275                 280                 285
Gln Asn Ala Leu Glu Gly Met Leu Asp Thr Leu Lys Lys Asp Ile Ala
    290                 295                 300
Leu Gly Glu Glu Phe Val Asn Lys
305                 310

<210> SEQ ID NO 125
<211> LENGTH: 939
<212> TYPE: DNA
<213> ORGANISM: Bacillus subtilis

<400> SEQUENCE: 125
atgggaaata ctcgtaaaaa agtttctgtt atcggagcag gttttaccgg agctacaact      60
gcattttttaa tcgctcaaaa agagctggca gacgttgttc ttgttgacat tccgcaattg     120
gagaacccga caagggaaa agcgcttgat atgcttgaag caagcccggt tcaaggcttt      180
gacgcaaaaa ttacgggaac atccaattac gaggatacag ccggctctga cattgttgtc     240
attacagccg gtatcgcaag aaaacctggt atgagcagag atgatctggt ctctacaaac     300
gaaaagatta tgagaagcgt tacgcaggaa atcgtgaaat attctcctga ctctattatt     360
gtggtgctga caaatcctgt tgatgcaatg acatacgcgg tgtacaaaga atcaggcttc     420
cctaaagagc gtgtaatcgg ccagtcaggt gtgcttgata cggcaagatt cagaacattt     480
gtggcagagg aattaaacct gtcagtgaaa gatgtgactg gtttcgtact cggcggacac     540
ggtgacgata tggttccgct tgtgcgttat tcttatgctg gcggtatccc gcttgaaact     600
cttattccga agaacggat tgacgcaatt gtggagcgca ctagaaaagg cggaggcgaa       660
atcgtgaatc ttcttggaaa cggaagcgcg tattatgcgc ctgcggcttc tctgacagaa     720
atggtcgaag cgatcttgaa agatcagcgc cgcgtccttc ctacaattgc ttatcttgaa     780
ggggaatacg gctatgaagg catctacctt ggtgttccta caattgtagg cggcaacggt     840
cttgagcaaa tcattgaact tgaactgaca gactatgaaa gagcgcagct gaataaatca     900
gttgaatctg tcaaaaatgt catgaaagta ttatcctaa                            939

<210> SEQ ID NO 126
<211> LENGTH: 312
<212> TYPE: PRT
<213> ORGANISM: Bacillus subtilis

<400> SEQUENCE: 126

Met Gly Asn Thr Arg Lys Lys Val Ser Val Ile Gly Ala Gly Phe Thr
1               5                   10                  15

Gly Ala Thr Thr Ala Phe Leu Ile Ala Gln Lys Glu Leu Ala Asp Val
            20                  25                  30

Val Leu Val Asp Ile Pro Gln Leu Glu Asn Pro Thr Lys Gly Lys Ala
        35                  40                  45

Leu Asp Met Leu Glu Ala Ser Pro Val Gln Gly Phe Asp Ala Lys Ile
    50                  55                  60

Thr Gly Thr Ser Asn Tyr Glu Asp Thr Ala Gly Ser Asp Ile Val Val
65                  70                  75                  80

Ile Thr Ala Gly Ile Ala Arg Lys Pro Gly Met Ser Arg Asp Asp Leu
                85                  90                  95

Val Ser Thr Asn Glu Lys Ile Met Arg Ser Val Thr Gln Glu Ile Val
            100                 105                 110

Lys Tyr Ser Pro Asp Ser Ile Ile Val Val Leu Thr Asn Pro Val Asp
        115                 120                 125

Ala Met Thr Tyr Ala Val Tyr Lys Glu Ser Gly Phe Pro Lys Glu Arg
    130                 135                 140

Val Ile Gly Gln Ser Gly Val Leu Asp Thr Ala Arg Phe Arg Thr Phe
145                 150                 155                 160

Val Ala Glu Glu Leu Asn Leu Ser Val Lys Asp Val Thr Gly Phe Val
                165                 170                 175

Leu Gly Gly His Gly Asp Asp Met Val Pro Leu Val Arg Tyr Ser Tyr
            180                 185                 190

Ala Gly Gly Ile Pro Leu Glu Thr Leu Ile Pro Lys Glu Arg Ile Asp
        195                 200                 205

Ala Ile Val Glu Arg Thr Arg Lys Gly Gly Glu Ile Val Asn Leu
    210                 215                 220

Leu Gly Asn Gly Ser Ala Tyr Tyr Ala Pro Ala Ala Ser Leu Thr Glu
225                 230                 235                 240

Met Val Glu Ala Ile Leu Lys Asp Gln Arg Arg Val Leu Pro Thr Ile
                245                 250                 255

Ala Tyr Leu Glu Gly Glu Tyr Gly Tyr Glu Gly Ile Tyr Leu Gly Val
            260                 265                 270

Pro Thr Ile Val Gly Gly Asn Gly Leu Glu Gln Ile Ile Glu Leu Glu
        275                 280                 285

Leu Thr Asp Tyr Glu Arg Ala Gln Leu Asn Lys Ser Val Glu Ser Val
    290                 295                 300

Lys Asn Val Met Lys Val Leu Ser
305                 310

<210> SEQ ID NO 127
<211> LENGTH: 1707
<212> TYPE: DNA
<213> ORGANISM: Zymomonas mobilis

<400> SEQUENCE: 127
atgagttata ctgtcggtac ctatttagcg gagcggcttg tccagattgg tctcaagcat    60
cacttcgcag tcgcgggcga ctacaacctc gtccttcttg acaacctgct tttgaacaaa   120
aacatggagc aggtttattg ctgtaacgaa ctgaactgcg gtttcagtgc agaaggttat   180
gctcgtgcca aggcgcagc agcagccgtc gttacctaca cgtcggtgc ctttccgca    240 tttgatgcta tcggtggcgc ctatgcagaa aaccttccgg ttatcctgat ctccggtgct   300
ccgaacaaca atgatcacgc tgctggtcac gtgttgcatc acgctcttgg caaaaccgac   360
tatcactatc agttggaaat ggccaagaac atcacggccg ccgctgaagc gatttacacc   420

```
ccggaagaag ctccggctaa aatcgatcac gtgattaaaa ctgctcttcg tgagaagaag    480
ccggtttatc tcgaaatcgc ttgcaacatt gcttccatgc cctgcgccgc tcctggaccg    540
gcaagcgcat tgttcaatga cgaagccagc gacgaagctt ctttgaatgc agcggttgaa    600
gaaaccctga aattcatcgc caaccgcgac aaagttgccg tcctcgtcgg cagcaagctg    660
cgcgcagctg gtgctgaaga agctgctgtc aaatttgctg atgctctcgg tggcgcagtt    720
gctaccatgg ctgctgcaaa aagcttcttt ccagaagaaa acccgcatta tcatcggcacc   780
tcatggggtg aagtcagcta tccgggcgtt gaaaagacga tgaaagaagc cgatgcggtt    840
atcgctctgg ctcctgtctt caacgactac tccaccactg gttggacgga tattcctgat    900
cctaagaaac tggttctcgc tgaaccgcgt tctgtcgtcg ttaacggcat tcgcttcccc    960
agcgtccatc tgaaagacta tctgacccgt ttggctcaga agtttccaa gaaaaccggt     1020
gcattggact tcttcaaatc cctcaatgca ggtgaactga agaaagccgc tccggctgat    1080
ccgagtgctc cgttggtcaa cgcagaaatc gcccgccaag tcgaagctct tctgaccccg    1140
aacacgacgg ttattgctga aaccggtgac tcttggttca atgctcagcg catgaagctc    1200
ccgaacggtg ctcgcgttga atatgaaatg cagtggggtc acattggttg gtccgttcct    1260
gccgccttcg gttatgccgt cggtgctccg gaacgtcgca catcctcat ggttggtgat     1320
ggttccttcc agctgacggc tcaggaagtc gctcagatgg ttcgcctgaa actgccggtt    1380
atcatcttct tgatcaataa ctatggttac accatcgaag ttatgatcca tgatggtccg    1440
tacaacaaca tcaagaactg ggattatgcc ggtctgatgg aagtgttcaa cggtaacggt    1500
ggttatgaca gcggtgctgg taaaggcctg aaggctaaaa ccggtggcga actggcagaa    1560
gctatcaagg ttgctctggc aaacaccgac ggcccaaccc tgatcgaatg cttcatcggt    1620
cgtgaagact gcactgaaga attggtcaaa tggggtaagc gcgttgctgc cgccaacagc    1680
cgtaagcctg ttaacaagct cctctag                                       1707
```

<210> SEQ ID NO 128
<211> LENGTH: 568
<212> TYPE: PRT
<213> ORGANISM: Zymomonas mobilis

<400> SEQUENCE: 128

```
Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140
```

```
Pro Ala Lys Ile Asp His Val Ile Lys Thr Ala Leu Arg Glu Lys Lys
145                 150                 155                 160
Pro Val Tyr Leu Glu Ile Ala Cys Asn Ile Ala Ser Met Pro Cys Ala
                165                 170                 175
Ala Pro Gly Pro Ala Ser Ala Leu Phe Asn Asp Glu Ala Ser Asp Glu
            180                 185                 190
Ala Ser Leu Asn Ala Ala Val Glu Glu Thr Leu Lys Phe Ile Ala Asn
        195                 200                 205
Arg Asp Lys Val Ala Val Leu Val Gly Ser Lys Leu Arg Ala Ala Gly
    210                 215                 220
Ala Glu Glu Ala Ala Val Lys Phe Ala Asp Ala Leu Gly Gly Ala Val
225                 230                 235                 240
Ala Thr Met Ala Ala Lys Ser Phe Phe Pro Glu Glu Asn Pro His
                245                 250                 255
Tyr Ile Gly Thr Ser Trp Gly Glu Val Ser Tyr Pro Gly Val Glu Lys
            260                 265                 270
Thr Met Lys Glu Ala Asp Ala Val Ile Ala Leu Ala Pro Val Phe Asn
        275                 280                 285
Asp Tyr Ser Thr Thr Gly Trp Thr Asp Ile Pro Asp Pro Lys Lys Leu
    290                 295                 300
Val Leu Ala Glu Pro Arg Ser Val Val Asn Gly Ile Arg Phe Pro
305                 310                 315                 320
Ser Val His Leu Lys Asp Tyr Leu Thr Arg Leu Ala Gln Lys Val Ser
                325                 330                 335
Lys Lys Thr Gly Ala Leu Asp Phe Phe Lys Ser Leu Asn Ala Gly Glu
            340                 345                 350
Leu Lys Lys Ala Ala Pro Ala Asp Pro Ser Ala Pro Leu Val Asn Ala
        355                 360                 365
Glu Ile Ala Arg Gln Val Glu Ala Leu Leu Thr Pro Asn Thr Thr Val
    370                 375                 380
Ile Ala Glu Thr Gly Asp Ser Trp Phe Asn Ala Gln Arg Met Lys Leu
385                 390                 395                 400
Pro Asn Gly Ala Arg Val Glu Tyr Glu Met Gln Trp Gly His Ile Gly
                405                 410                 415
Trp Ser Val Pro Ala Ala Phe Gly Tyr Ala Val Gly Ala Pro Glu Arg
            420                 425                 430
Arg Asn Ile Leu Met Val Gly Asp Gly Ser Phe Gln Leu Thr Ala Gln
        435                 440                 445
Glu Val Ala Gln Met Val Arg Leu Lys Leu Pro Val Ile Ile Phe Leu
    450                 455                 460
Ile Asn Asn Tyr Gly Tyr Thr Ile Glu Val Met Ile His Asp Gly Pro
465                 470                 475                 480
Tyr Asn Asn Ile Lys Asn Trp Asp Tyr Ala Gly Leu Met Glu Val Phe
                485                 490                 495
Asn Gly Asn Gly Gly Tyr Asp Ser Gly Ala Gly Lys Gly Leu Lys Ala
            500                 505                 510
Lys Thr Gly Gly Glu Leu Ala Glu Ala Ile Lys Val Ala Leu Ala Asn
        515                 520                 525
Thr Asp Gly Pro Thr Leu Ile Glu Cys Phe Ile Gly Arg Glu Asp Cys
    530                 535                 540
Thr Glu Glu Leu Val Lys Trp Gly Lys Arg Val Ala Ala Ala Asn Ser
545                 550                 555                 560
Arg Lys Pro Val Asn Lys Leu Leu
```

<210> SEQ ID NO 129
<211> LENGTH: 1644
<212> TYPE: DNA
<213> ORGANISM: Lactococcus lactis

<400> SEQUENCE: 129

```
atgtataccg ttggggatta tctgctggat cgcttgcatg agttaggcat tgaagaaatt      60
ttcggcgtac ctggtgacta taatctccag tttcttgatc agatcatctc acgcgaagat     120
atgaaatgga ttggtaatgc caatgaactg aatgccagct atatggctga cggttatgcg     180
cgtactaaga aagcggcagc ctttctgacg acctttggcg taggcgagtt aagcgccatt     240
aacggactcg ctggctccta tgctgagaac ttgccggtag tcgaaatcgt gggctctcca     300
acgtccaaag tacaaaatga cggaaaattc gtgcatcata ccctcgcgga tggtgacttt     360
aaacacttta tgaaaatgca tgaaccggta acagccgcgc gtaccctgct gactgcggag     420
aatgcgacct acgaaattga tcgcgtttta agccagctgt taaaagaacg caaacccgtc     480
tacatcaatc tgcctgttga tgtagcagcc gctaaagctg agaaaccggc gcttagtctg     540
gaaaaggagt cgagcaccac caatacgacc gaacaagtga ttctgtccaa aattgaagaa     600
tcccttaaaa acgcacagaa accggtggtt attgccgggc atgaagtgat tagctttggg     660
ttggagaaaa ccgtcactca gttcgtcagt gaaaccaaat tgccgattac cacgctgaac     720
tttggtaaga gcgcggttga cgagagcttg ccatcgttcc tggggatcta aacggtaag      780
ctgtctgaaa tttcgctgaa gactttgtg gaatcagcgg atttcatttt gatgctgggt       840
gtgaaactca cggattcttc gactggggca tttacccacc atctggacga aaacaaaatg     900
atcagcttga acatcgacga gggcattatc ttcaacaagg tggtcgaaga tttcgatttt     960
cgtgcagtgg tgtccagtct ctcggaactg aagggtattg aatatgaggg tcagtacatc    1020
gataaacagt atgaagagtt catcccgtca tctgccctc tgagccaaga ccgcctttgg     1080
caggcagtgg aaagcctcac acagtccaat gaaacgatcg ttgcagaaca aggtactagt    1140
ttctttggcg caagcacgat cttcctgaaa tcgaactcac ggttcatcgg acaaccgctg    1200
tggggcagta ttggctatac gttccagcg gcgttaggat cacagattgc ggataaggaa     1260
agtcgtcacc tgttattcat tggcgatggt tctcttcaac ttacggtcca ggaactgggc    1320
ctgtccattc gcgagaaact gaacccgatt tgctttatca tcaacaatga cggctacaca    1380
gtggagcgcg aaattcacgg cccgacccag agttacaatg acattcccat gtggaactac    1440
agcaaattac cagaaacctt tggtgccaca gaagatcgtg ttgtctctaa atcgtgcgc      1500
actgagaacg aatttgtttc ggttatgaaa gaagcgcaag cggatgtgaa tcggatgtat    1560
tggattgaac tggtcctgga gaaagaagat gccccgaaac tgctgaagaa aatgggcaaa    1620
ctgtttgctg aacagaacaa ataa                                           1644
```

<210> SEQ ID NO 130
<211> LENGTH: 547
<212> TYPE: PRT
<213> ORGANISM: Lactococcus lactis

<400> SEQUENCE: 130

```
Met Tyr Thr Val Gly Asp Tyr Leu Leu Asp Arg Leu His Glu Leu Gly
1               5                   10                  15
Ile Glu Glu Ile Phe Gly Val Pro Gly Asp Tyr Asn Leu Gln Phe Leu
            20                  25                  30
```

-continued

```
Asp Gln Ile Ile Ser Arg Glu Asp Met Lys Trp Ile Gly Asn Ala Asn
         35                  40                  45
Glu Leu Asn Ala Ser Tyr Met Ala Asp Gly Tyr Ala Arg Thr Lys Lys
 50                  55                  60
Ala Ala Ala Phe Leu Thr Thr Phe Gly Val Gly Glu Leu Ser Ala Ile
 65              70                  75                      80
Asn Gly Leu Ala Gly Ser Tyr Ala Glu Asn Leu Pro Val Val Glu Ile
                 85                  90                  95
Val Gly Ser Pro Thr Ser Lys Val Gln Asn Asp Gly Lys Phe Val His
             100                 105                 110
His Thr Leu Ala Asp Gly Asp Phe Lys His Phe Met Lys Met His Glu
         115                 120                 125
Pro Val Thr Ala Ala Arg Thr Leu Leu Thr Ala Glu Asn Ala Thr Tyr
     130                 135                 140
Glu Ile Asp Arg Val Leu Ser Gln Leu Leu Lys Glu Arg Lys Pro Val
145                 150                 155                 160
Tyr Ile Asn Leu Pro Val Asp Val Ala Ala Ala Lys Ala Glu Lys Pro
                 165                 170                 175
Ala Leu Ser Leu Glu Lys Glu Ser Ser Thr Asn Thr Thr Glu Gln
             180                 185                 190
Val Ile Leu Ser Lys Ile Glu Glu Ser Leu Lys Asn Ala Gln Lys Pro
         195                 200                 205
Val Val Ile Ala Gly His Glu Val Ile Ser Phe Gly Leu Glu Lys Thr
     210                 215                 220
Val Thr Gln Phe Val Ser Glu Thr Lys Leu Pro Ile Thr Thr Leu Asn
225                 230                 235                 240
Phe Gly Lys Ser Ala Val Asp Glu Ser Leu Pro Ser Phe Leu Gly Ile
                 245                 250                 255
Tyr Asn Gly Lys Leu Ser Glu Ile Ser Leu Lys Asn Phe Val Glu Ser
             260                 265                 270
Ala Asp Phe Ile Leu Met Leu Gly Val Lys Leu Thr Asp Ser Ser Thr
         275                 280                 285
Gly Ala Phe Thr His His Leu Asp Glu Asn Lys Met Ile Ser Leu Asn
     290                 295                 300
Ile Asp Glu Gly Ile Ile Phe Asn Lys Val Val Glu Asp Phe Asp Phe
305                 310                 315                 320
Arg Ala Val Val Ser Ser Leu Ser Glu Leu Lys Gly Ile Glu Tyr Glu
                 325                 330                 335
Gly Gln Tyr Ile Asp Lys Gln Tyr Glu Phe Ile Pro Ser Ser Ala
             340                 345                 350
Pro Leu Ser Gln Asp Arg Leu Trp Gln Ala Val Glu Ser Leu Thr Gln
         355                 360                 365
Ser Asn Glu Thr Ile Val Ala Glu Gln Gly Thr Ser Phe Phe Gly Ala
     370                 375                 380
Ser Thr Ile Phe Leu Lys Ser Asn Ser Arg Phe Ile Gly Gln Pro Leu
385                 390                 395                 400
Trp Gly Ser Ile Gly Tyr Thr Phe Pro Ala Ala Leu Gly Ser Gln Ile
                 405                 410                 415
Ala Asp Lys Glu Ser Arg His Leu Leu Phe Ile Gly Asp Gly Ser Leu
             420                 425                 430
Gln Leu Thr Val Gln Glu Leu Gly Leu Ser Ile Arg Glu Lys Leu Asn
         435                 440                 445
```

```
Pro Ile Cys Phe Ile Ile Asn Asn Asp Gly Tyr Thr Val Glu Arg Glu
    450                 455                 460
Ile His Gly Pro Thr Gln Ser Tyr Asn Asp Ile Pro Met Trp Asn Tyr
465                 470                 475                 480
Ser Lys Leu Pro Glu Thr Phe Gly Ala Thr Glu Asp Arg Val Val Ser
                485                 490                 495
Lys Ile Val Arg Thr Glu Asn Glu Phe Val Ser Val Met Lys Glu Ala
            500                 505                 510
Gln Ala Asp Val Asn Arg Met Tyr Trp Ile Glu Leu Val Leu Glu Lys
        515                 520                 525
Glu Asp Ala Pro Lys Leu Leu Lys Lys Met Gly Lys Leu Phe Ala Glu
    530                 535                 540
Gln Asn Lys
545
```

<210> SEQ ID NO 131
<211> LENGTH: 27
<212> TYPE: DNA
<213> ORGANISM: Artificial Sequence
<220> FEATURE:
<223> OTHER INFORMATION: Primer for amplification

<400> SEQUENCE: 131
tataatcata tgaaagtcgc agtcctc                                    27

<210> SEQ ID NO 132
<211> LENGTH: 30
<212> TYPE: DNA
<213> ORGANISM: Artificial Sequence
<220> FEATURE:
<223> OTHER INFORMATION: Primer for amplification

<400> SEQUENCE: 132
tataatggat ccttacttat taacgaactc                                 30

<210> SEQ ID NO 133
<211> LENGTH: 33
<212> TYPE: DNA
<213> ORGANISM: Artificial Sequence
<220> FEATURE:
<223> OTHER INFORMATION: Primer for amplification

<400> SEQUENCE: 133
tataatcata tggctgataa acaacgtaaa aaa                             33

<210> SEQ ID NO 134
<211> LENGTH: 36
<212> TYPE: DNA
<213> ORGANISM: Artificial Sequence
<220> FEATURE:
<223> OTHER INFORMATION: Primer for amplification

<400> SEQUENCE: 134
tataatggat ccttagtttt taactgcaga agcaaa                          36

<210> SEQ ID NO 135
<211> LENGTH: 27
<212> TYPE: DNA
<213> ORGANISM: Artificial Sequence
<220> FEATURE:
<223> OTHER INFORMATION: Primer for amplification

<400> SEQUENCE: 135

```
catatgggaa atactcgtaa aaaagtt                                               27
```

<210> SEQ ID NO 136
<211> LENGTH: 27
<212> TYPE: DNA
<213> ORGANISM: Artificial Sequence
<220> FEATURE:
<223> OTHER INFORMATION: Primer for amplification

<400> SEQUENCE: 136

```
ggatccttag gataatactt tcatgac                                               27
```

<210> SEQ ID NO 137
<211> LENGTH: 24
<212> TYPE: DNA
<213> ORGANISM: Artificial Sequence
<220> FEATURE:
<223> OTHER INFORMATION: Primer for amplification

<400> SEQUENCE: 137

```
catatgatta tttccgcagc cagc                                                  24
```

<210> SEQ ID NO 138
<211> LENGTH: 25
<212> TYPE: DNA
<213> ORGANISM: Artificial Sequence
<220> FEATURE:
<223> OTHER INFORMATION: Primer for amplification

<400> SEQUENCE: 138

```
agatctctat gccgcattcc ctttc                                                 25
```

<210> SEQ ID NO 139
<211> LENGTH: 41
<212> TYPE: DNA
<213> ORGANISM: Artificial Sequence
<220> FEATURE:
<223> OTHER INFORMATION: Primer for amplification

<400> SEQUENCE: 139

```
ttacagccgg tatcgcagca aaacccggga tgagcagaga t                               41
```

<210> SEQ ID NO 140
<211> LENGTH: 41
<212> TYPE: DNA
<213> ORGANISM: Artificial Sequence
<220> FEATURE:
<223> OTHER INFORMATION: Primer for amplification

<400> SEQUENCE: 140

```
atctctgctc atcccgggtt ttgctgcgat accggctgta a                               41
```

<210> SEQ ID NO 141
<211> LENGTH: 43
<212> TYPE: DNA
<213> ORGANISM: Artificial Sequence
<220> FEATURE:
<223> OTHER INFORMATION: Primer for amplification
<220> FEATURE:
<221> NAME/KEY: misc_feature
<222> LOCATION: (21)..(22)
<223> OTHER INFORMATION: n is a, c, g, or t

<400> SEQUENCE: 141

```
ttatctctgc aggcgtagcg nnkaaacccg ggatggatcg ttc                             43
```

<210> SEQ ID NO 142
<211> LENGTH: 43
<212> TYPE: DNA
<213> ORGANISM: Artificial Sequence
<220> FEATURE:
<223> OTHER INFORMATION: Primer for amplification
<220> FEATURE:
<221> NAME/KEY: misc_feature
<222> LOCATION: (22)..(23)
<223> OTHER INFORMATION: n is a, c, g, or t

<400> SEQUENCE: 142
gaacgatcca tcccgggttt mnncgctacg cctgcagaga taa            43

<210> SEQ ID NO 143
<211> LENGTH: 50
<212> TYPE: DNA
<213> ORGANISM: Artificial Sequence
<220> FEATURE:
<223> OTHER INFORMATION: Primer for amplification

<400> SEQUENCE: 143
ttatctctgc aggcgtagcg gctaaaccgg gtgaggatcg ttccgacctg            50

<210> SEQ ID NO 144
<211> LENGTH: 50
<212> TYPE: DNA
<213> ORGANISM: Artificial Sequence
<220> FEATURE:
<223> OTHER INFORMATION: Primer for amplification

<400> SEQUENCE: 144
caggtcggaa cgatcctcac ccggtttagc cgctacgcct gcagagataa            50

<210> SEQ ID NO 145
<211> LENGTH: 50
<212> TYPE: DNA
<213> ORGANISM: Artificial Sequence
<220> FEATURE:
<223> OTHER INFORMATION: Primer for amplification

<400> SEQUENCE: 145
ttatctctgc aggcgtagcg gctaaaccgg gtcaggatcg ttccgacctg            50

<210> SEQ ID NO 146
<211> LENGTH: 50
<212> TYPE: DNA
<213> ORGANISM: Artificial Sequence
<220> FEATURE:
<223> OTHER INFORMATION: Primer for amplification

<400> SEQUENCE: 146
caggtcggaa cgatcctgac ccggtttagc cgctacgcct gcagagataa            50

<210> SEQ ID NO 147
<211> LENGTH: 46
<212> TYPE: DNA
<213> ORGANISM: Artificial Sequence
<220> FEATURE:
<223> OTHER INFORMATION: Primer for amplification

<400> SEQUENCE: 147
gtcgcagtcc tcggcgccgc tggcggtgtc ggccaggcgc ttgcac            46

<210> SEQ ID NO 148
<211> LENGTH: 46
<212> TYPE: DNA

```
<213> ORGANISM: Artificial Sequence
<220> FEATURE:
<223> OTHER INFORMATION: Primer for amplification

<400> SEQUENCE: 148
gtgcaagcgc ctggccgaca ccgccagcgg cgccgaggac tgcgac              46

<210> SEQ ID NO 149
<211> LENGTH: 45
<212> TYPE: DNA
<213> ORGANISM: Artificial Sequence
<220> FEATURE:
<223> OTHER INFORMATION: Primer for amplification

<400> SEQUENCE: 149
ccggttattg gcggccactc tgatgttacc attctgccgc tgctg               45

<210> SEQ ID NO 150
<211> LENGTH: 45
<212> TYPE: DNA
<213> ORGANISM: Artificial Sequence
<220> FEATURE:
<223> OTHER INFORMATION: Primer for amplification

<400> SEQUENCE: 150
cagcagcggc agaatggtaa catcagagtg gccgccaata accgg               45

<210> SEQ ID NO 151
<211> LENGTH: 39
<212> TYPE: DNA
<213> ORGANISM: Artificial Sequence
<220> FEATURE:
<223> OTHER INFORMATION: Primer for amplification

<400> SEQUENCE: 151
ggcgtagcgg ctaaaccggg tatgtctcgt tccgacctg                      39

<210> SEQ ID NO 152
<211> LENGTH: 39
<212> TYPE: DNA
<213> ORGANISM: Artificial Sequence
<220> FEATURE:
<223> OTHER INFORMATION: Primer for amplification

<400> SEQUENCE: 152
caggtcggaa cgagacatac ccggtttagc cgctacgcc                      39

<210> SEQ ID NO 153
<211> LENGTH: 939
<212> TYPE: DNA
<213> ORGANISM: Bacillus subtilis

<400> SEQUENCE: 153
atgggaaata ctcgtaaaaa agtttctgtt atcggagcag gttttaccgg agctacaact      60
gcatttttaa tcgctcaaaa agagctggca gacgttgttc ttgttgacat tccgcaattg     120
gagaacccga caaagggaaa agcgcttgat atgcttgaag caagcccggt tcaaggcttt     180
gacgcaaaaa ttacgggaac atccaattac gaggatacag ccggctctga cattgttgtc     240
attacagccg gtatcgcatg caaacccggc atgagcagag atgatctggt ctctacaaac     300
gaaaagatta tgagaagcgt tacgcaggaa atcgtgaaat attctcctga ctctattatt     360
gtggtgctga caaatcctgt tgatgcaatg acatacgcgg tgtacaaaga atcaggcttc     420
cctaaagagc gtgtaatcgg ccagtcaggt gtgcttgata cggcaagatt cagaacattt     480
```

```
gtggcagagg aattaaacct gtcagtgaaa gatgtgactg gtttcgtact cggcggacac    540
ggtgacgata tggttccgct tgtgcgttat tcttatgctg gcggtatccc gcttgaaact    600
cttattccga agaacggat tgacgcaatt gtggagcgca ctagaaaagg cggaggcgaa     660
atcgtgaatc ttcttggaaa cggaagcgcg tattatgcgc ctgcggcttc tctgacagaa   720
atggtcgaag cgatcttgaa agatcagcgc cgcgtccttc ctacaattgc ttatcttgaa   780
ggggaatacg gctatgaagg catctacctt ggtgttccta caattgtagg cggcaacggt   840
cttgagcaaa tcattgaact tgaactgaca gactatgaaa gagcgcagct gaataaatca   900
gttgaatctg tcaaaaatgt catgaaagta ttatcctaa                          939
```

<210> SEQ ID NO 154
<211> LENGTH: 312
<212> TYPE: PRT
<213> ORGANISM: Bacillus subtilis

<400> SEQUENCE: 154

```
Met Gly Asn Thr Arg Lys Lys Val Ser Val Ile Gly Ala Gly Phe Thr
1               5                   10                  15

Gly Ala Thr Thr Ala Phe Leu Ile Ala Gln Lys Glu Leu Ala Asp Val
            20                  25                  30

Val Leu Val Asp Ile Pro Gln Leu Glu Asn Pro Thr Lys Gly Lys Ala
        35                  40                  45

Leu Asp Met Leu Glu Ala Ser Pro Val Gln Gly Phe Asp Ala Lys Ile
    50                  55                  60

Thr Gly Thr Ser Asn Tyr Glu Asp Thr Ala Gly Ser Asp Ile Val Val
65                  70                  75                  80

Ile Thr Ala Gly Ile Ala Cys Lys Pro Gly Met Ser Arg Asp Asp Leu
                85                  90                  95

Val Ser Thr Asn Glu Lys Ile Met Arg Ser Val Thr Gln Glu Ile Val
            100                 105                 110

Lys Tyr Ser Pro Asp Ser Ile Ile Val Val Leu Thr Asn Pro Val Asp
        115                 120                 125

Ala Met Thr Tyr Ala Val Tyr Lys Glu Ser Gly Phe Pro Lys Glu Arg
    130                 135                 140

Val Ile Gly Gln Ser Gly Val Leu Asp Thr Ala Arg Phe Arg Thr Phe
145                 150                 155                 160

Val Ala Glu Glu Leu Asn Leu Ser Val Lys Asp Val Thr Gly Phe Val
                165                 170                 175

Leu Gly Gly His Gly Asp Asp Met Val Pro Leu Val Arg Tyr Ser Tyr
            180                 185                 190

Ala Gly Gly Ile Pro Leu Glu Thr Leu Ile Pro Lys Glu Arg Ile Asp
        195                 200                 205

Ala Ile Val Glu Arg Thr Arg Lys Gly Gly Glu Ile Val Asn Leu
    210                 215                 220

Leu Gly Asn Gly Ser Ala Tyr Tyr Ala Pro Ala Ala Ser Leu Thr Glu
225                 230                 235                 240

Met Val Glu Ala Ile Leu Lys Asp Gln Arg Arg Val Leu Pro Thr Ile
                245                 250                 255

Ala Tyr Leu Glu Gly Glu Tyr Gly Tyr Glu Gly Ile Tyr Leu Gly Val
            260                 265                 270

Pro Thr Ile Val Gly Gly Asn Gly Leu Glu Gln Ile Ile Glu Leu Glu
        275                 280                 285
```

Leu Thr Asp Tyr Glu Arg Ala Gln Leu Asn Lys Ser Val Glu Ser Val
        290                 295                 300

Lys Asn Val Met Lys Val Leu Ser
305                 310

<210> SEQ ID NO 155
<211> LENGTH: 939
<212> TYPE: DNA
<213> ORGANISM: Escherichia coli

<400> SEQUENCE: 155

```
atgaaagtcg cagtcctcgg cgctgctggc ggtattggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg ttttctggt     180
gaagatgcga ctccggcgct ggaaggcgca gatgtcgttc ttatctctgc aggcgtagcg     240
gctaaacccg ggatggatcg ttccgacctg tttaacgtta acgccggcat cgtgaaaaac     300
ctggtacagc aagttgcgaa aacctgcccg aaagcgtgca ttggtattat cactaacccg     360
gttaacacca cagttgcaat tgctgctgaa gtgctgaaaa agccggtgt ttatgacaaa      420
aacaaactgt tcggcgttac cacgctggat atcattcgtt ccaacacctt tgttgcggaa     480
ctgaaaggca acagccagg cgaagttgaa gtgccggtta ttggcggtca ctctggtgtt      540
accattctgc cgctgctgtc acaggttcct ggcgttagtt ttaccgagca ggaagtggct     600
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt     720
gcactgcagg gcgaacaagg cgttgtcgaa tgtgcctacg ttgaaggcga cggtcagtac     780
gcccgtttct tctctcaacc gctgctgctg ggtaaaaacg gcgtggaaga gcgtaaatct     840
atcggtaccc tgagcgcatt tgaacagaac gcgctggaag gtatgctgga tacgctgaag     900
aaagatatcg ccctgggcga agagttcgtt aataagtaa                           939
```

<210> SEQ ID NO 156
<211> LENGTH: 312
<212> TYPE: PRT
<213> ORGANISM: Escherichia coli

<400> SEQUENCE: 156

Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
            165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
            195                 200                 205

Ala Gly Thr Glu Val Val Glu Ala Lys Ala Gly Gly Ser Ala Thr
        210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Cys Ala Tyr Val Glu Gly
                245                 250                 255

Asp Gly Gln Tyr Ala Arg Phe Phe Ser Gln Pro Leu Leu Gly Lys
            260                 265                 270

Asn Gly Val Glu Glu Arg Lys Ser Ile Gly Thr Leu Ser Ala Phe Glu
            275                 280                 285

Gln Asn Ala Leu Glu Gly Met Leu Asp Thr Leu Lys Lys Asp Ile Ala
        290                 295                 300

Leu Gly Glu Glu Phe Val Asn Lys
305                 310

<210> SEQ ID NO 157
<211> LENGTH: 939
<212> TYPE: DNA
<213> ORGANISM: Escherichia coli

<400> SEQUENCE: 157
atgaaagtcg cagtcctcgg cgctgctggc ggtattggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg ttttctggt     180 gaagatgcga ctccggcgct ggaaggcgca gatgtcgttc ttatctctgc aggcgtagcg     240
gctaaaccgg tcaggatcg ttccgacctg tttaacgtta acgccggcat cgtgaaaaac     300
ctggtacagc aagttgcgaa aacctgcccg aaagcgtgca ttggtattat cactaacccg     360
gttaacacca cagttgcaat tgctgctgaa gtgctgaaaa agccggtgt ttatgacaaa     420 aacaaactgt tcggcgttac cacgctggat atcattcgtt ccaacacctt gttgcggaa     480 ctgaaaggca acagccagg cgaagttgaa gtgccggtta ttggcggtca ctctggtgtt     540
accattctgc cgctgctgtc acaggttcct ggcgttagtt ttaccgagca ggaagtggct     600
gatctgacca aacgcatcca gaacgcgggt actgaagtgg ttgaagcgaa ggccggtggc     660
gggtctgcaa ccctgtctat gggccaggca gctgcacgtt ttggtctgtc tctggttcgt     720
gcactgcagg gcgaacaagg cgttgtcgaa tgtgcctacg ttgaaggcga cggtcagtac     780
gcccgtttct tctctcaacc gctgctgctg ggtaaaaacg cgtggaaga gcgtaaatct     840 atcggtaccc tgagcgcatt tgaacagaac gcgctggaag gtatgctgga tacgctgaag     900
aaagatatcg ccctgggcga agagttcgtt aataagtaa                            939

<210> SEQ ID NO 158
<211> LENGTH: 312
<212> TYPE: PRT

<213> ORGANISM: Escherichia coli

<400> SEQUENCE: 158

```
Met Lys Val Ala Val Leu Gly Ala Ala Gly Gly Ile Gly Gln Ala Leu
1               5                   10                  15
Ala Leu Leu Leu Lys Thr Gln Leu Pro Ser Gly Ser Glu Leu Ser Leu
            20                  25                  30
Tyr Asp Ile Ala Pro Val Thr Pro Gly Val Ala Val Asp Leu Ser His
        35                  40                  45
Ile Pro Thr Ala Val Lys Ile Lys Gly Phe Ser Gly Glu Asp Ala Thr
    50                  55                  60
Pro Ala Leu Glu Gly Ala Asp Val Val Leu Ile Ser Ala Gly Val Ala
65                  70                  75                  80
Ala Lys Pro Gly Gln Asp Arg Ser Asp Leu Phe Asn Val Asn Ala Gly
                85                  90                  95
Ile Val Lys Asn Leu Val Gln Gln Val Ala Lys Thr Cys Pro Lys Ala
            100                 105                 110
Cys Ile Gly Ile Ile Thr Asn Pro Val Asn Thr Thr Val Ala Ile Ala
        115                 120                 125
Ala Glu Val Leu Lys Lys Ala Gly Val Tyr Asp Lys Asn Lys Leu Phe
    130                 135                 140
Gly Val Thr Thr Leu Asp Ile Ile Arg Ser Asn Thr Phe Val Ala Glu
145                 150                 155                 160
Leu Lys Gly Lys Gln Pro Gly Glu Val Glu Val Pro Val Ile Gly Gly
                165                 170                 175
His Ser Gly Val Thr Ile Leu Pro Leu Leu Ser Gln Val Pro Gly Val
            180                 185                 190
Ser Phe Thr Glu Gln Glu Val Ala Asp Leu Thr Lys Arg Ile Gln Asn
        195                 200                 205
Ala Gly Thr Glu Val Val Glu Ala Lys Ala Gly Gly Ser Ala Thr
    210                 215                 220
Leu Ser Met Gly Gln Ala Ala Arg Phe Gly Leu Ser Leu Val Arg
225                 230                 235                 240
Ala Leu Gln Gly Glu Gln Gly Val Val Glu Cys Ala Tyr Val Glu Gly
                245                 250                 255
Asp Gly Gln Tyr Ala Arg Phe Phe Ser Gln Pro Leu Leu Gly Lys
            260                 265                 270
Asn Gly Val Glu Glu Arg Lys Ser Ile Gly Thr Leu Ser Ala Phe Glu
        275                 280                 285
Gln Asn Ala Leu Glu Gly Met Leu Asp Thr Leu Lys Lys Asp Ile Ala
    290                 295                 300
Leu Gly Glu Glu Phe Val Asn Lys
305                 310
```

<210> SEQ ID NO 159
<211> LENGTH: 939
<212> TYPE: DNA
<213> ORGANISM: Escherichia coli

<400> SEQUENCE: 159

```
atgaaagtcg cagtcctcgg cgctgctggc ggtattggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg ttttctggt     180 gaagatgcga ctccggcgct ggaaggcgca gatgtcgttc ttatctctgc aggcgtagcg     240
```

```
gctaaaccgg gtgaggatcg ttccgacctg tttaacgtta acgccggcat cgtgaaaaac    300
ctggtacagc aagttgcgaa aacctgcccg aaagcgtgca ttggtattat cactaacccg    360
gttaacacca cagttgcaat tgctgctgaa gtgctgaaaa agccggtgt ttatgacaaa    420 aacaaactgt tcggcgttac cacgctggat atcattcgtt ccaacacctt tgttgcggaa    480
ctgaaaggca aacagccagg cgaagttgaa gtgccggtta ttggcggtca ctctggtgtt    540
accattctgc cgctgctgtc acaggttcct ggcgttagtt ttaccgagca ggaagtggct    600
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt    720
gcactgcagg gcgaacaagg cgttgtcgaa tgtgcctacg ttgaaggcga cggtcagtac    780
gcccgtttct ctctcaacc gctgctgctg ggtaaaaacg gcgtggaaga gcgtaaatct    840
atcggtaccc tgagcgcatt tgaacagaac gcgctggaag gtatgctgga tacgctgaag    900
aaagatatcg ccctgggcga agagttcgtt aataagtaa                           939
```

<210> SEQ ID NO 160
<211> LENGTH: 312
<212> TYPE: PRT
<213> ORGANISM: Escherichia coli

<400> SEQUENCE: 160

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Glu Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Lys Ala Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
```

```
                    245                 250                 255
Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
            275                 280                 285

Gln Asn Ala Leu Glu Gly Met Leu Asp Thr Leu Lys Lys Asp Ile Ala
        290                 295                 300

Leu Gly Glu Glu Phe Val Asn Lys
305                 310

<210> SEQ ID NO 161
<211> LENGTH: 939
<212> TYPE: DNA
<213> ORGANISM: Escherichia coli

<400> SEQUENCE: 161
atgaaagtcg cagtcctcgg cgctgctggc ggtgtcggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg ttttttctggt    180 gaagatgcga ctccggcgct ggaaggcgca gatgtcgttc ttatctctgc aggcgtagcg     240
gctaaacccg gatggatcg ttccgacctg tttaacgtta acgccggcat cgtgaaaaac      300
ctggtacagc aagttgcgaa acctgcccg aaagcgtgca ttggtattat cactaacccg      360
gttaacacca cagttgcaat tgctgctgaa gtgctgaaaa agccggtgt ttatgacaaa      420 aacaaactgt tcggcgttac cacgctggat atcattcgtt ccaacacctt gttgcggaa     480 ctgaaaggca acagccagg cgaagttgaa gtgccggtta ttggcggtca ctctggtgtt     540
accattctgc cgctgctgtc acaggttcct ggcgttagtt ttaccgagca ggaagtggct    600
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt    720
gcactgcagg gcgaacaagg cgttgtcgaa tgtgcctacg ttgaaggcga cggtcagtac    780
gcccgttcct tctctcaacc gctgctgctg ggtaaaaacg cgtgggaaga cgtaaatct    840 atcggtaccc tgagcgcatt tgaacagaac gcgctggaag gtatgctgga tacgctgaag    900
aaagatatcg ccctgggcga agagttcgtt aataagtaa                           939

<210> SEQ ID NO 162
<211> LENGTH: 312
<212> TYPE: PRT
<213> ORGANISM: Escherichia coli

<400> SEQUENCE: 162

Met Lys Val Ala Val Leu Gly Ala Ala Gly Gly Val Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Met Asp Arg Ser Asp Leu Phe Asn Val Asn Ala Gly
                85                  90                  95
```

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
    290                 295                 300

Leu Gly Glu Glu Phe Val Asn Lys
305                 310

<210> SEQ ID NO 163
<211> LENGTH: 939
<212> TYPE: DNA
<213> ORGANISM: Escherichia coli

<400> SEQUENCE: 163
atgaaagtcg cagtcctcgg cgccgctggc ggtgtcggcc aggcgcttgc actactgtta    60 aaacccaac tgccttcagg ttcagaactc tctctgtatg atatcgctcc agtgactccc    120
ggtgtggctg tcgatctgag ccatatccct actgctgtga aaatcaaagg ttttttctggt   180 gaagatgcga ctccggcgct ggaaggcgca gatgtcgttc ttatctctgc aggcgtagcg    240
gctaaaccgg tcaggatcg ttccgacctg tttaacgtta acgccggcat cgtgaaaaac    300
ctggtacagc aagttgcgaa acctgcccg aaagcgtgca ttggtattat cactaacccg    360
gttaacacca cagttgcaat tgctgctgaa gtgctgaaaa agccggtgt ttatgacaaa    420 aacaaactgt tcggcgttac cacgctggat atcattcgtt ccaacacctt tgttgcggaa    480
ctgaaaggca acagccagg cgaagttgaa gtgccggtta ttggcggtca ctctggtgtt    540
accattctgc cgctgctgtc acaggttcct ggcgttagtt ttaccgagca ggaagtggct    600
gatctgacca acgcatcca gaacgcgggt actgaagtgg ttgaagcgaa ggccggtggc    660
gggtctgcaa ccctgtctat gggccaggca gctgcacgtt ttggtctgtc tctggttcgt    720
gcactgcagg gcgaacaagg cgttgtcgaa tgtgcctacg ttgaaggcga cggtcagtac    780
gcccgtttct tctctcaacc gctgctgctg ggtaaaaacg gcgtggaaga gcgtaaatct    840

```
atcggtaccc tgagcgcatt tgaacagaac gcgctggaag gtatgctgga tacgctgaag    900
aaagatatcg ccctgggcga agagttcgtt aataagtaa                           939
```

<210> SEQ ID NO 164
<211> LENGTH: 312
<212> TYPE: PRT
<213> ORGANISM: Escherichia coli

<400> SEQUENCE: 164

| Met | Lys | Val | Ala | Val | Leu | Gly | Ala | Ala | Gly | Val | Gly | Gln | Ala | Leu |
|---|---|---|---|---|---|---|---|---|---|---|---|---|---|---|
| 1 | | | | 5 | | | | | 10 | | | | | 15 |

Ala Leu Leu Leu Lys Thr Gln Leu Pro Ser Gly Ser Glu Leu Ser Leu
        20                  25                  30

Tyr Asp Ile Ala Pro Val Thr Pro Gly Val Ala Val Asp Leu Ser His
            35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Gln Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Gly Lys
            260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
    290                 295                 300

Leu Gly Glu Glu Phe Val Asn Lys
305                 310

<210> SEQ ID NO 165
<211> LENGTH: 939
<212> TYPE: DNA
<213> ORGANISM: Escherichia coli

<400> SEQUENCE: 165

```
atgaaagtcg cagtcctcgg cgccgctggc ggtgtcggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg ttttttctggt    180
gaagatgcga ctccggcgct ggaaggcgca gatgtcgttc ttatctctgc aggcgtagcg     240
gctaaaccgg gtgaggatcg ttccgacctg tttaacgtta acgccggcat cgtgaaaaac     300
ctggtacagc aagttgcgaa aacctgcccg aaagcgtgca ttggtattat cactaacccg     360
gttaacacca cagttgcaat tgctgctgaa gtgctgaaaa agccggtgt ttatgacaaa      420
aacaaactgt tcggcgttac cacgctggat atcattcgtt ccaacacctt tgttgcggaa     480
ctgaaaggca acagccagg cgaagttgaa gtgccggtta ttggcggtca ctctggtgtt      540
accattctgc cgctgctgtc acaggttcct ggcgttagtt ttaccgagca ggaagtggct     600
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt    720
gcactgcagg gcgaacaagg cgttgtcgaa tgtgcctacg ttgaaggcga cggtcagtac    780
gcccgttttct tctctcaacc gctgctgctg gtaaaaaacg gcgtggaaga gcgtaaatct    840
atcggtaccc tgagcgcatt tgaacagaac gcgctggaag gtatgctgga tacgctgaag    900
aaagatatcg ccctgggcga agagttcgtt aataagtaa                            939

<210> SEQ ID NO 166
<211> LENGTH: 312
<212> TYPE: PRT
<213> ORGANISM: Escherichia coli

<400> SEQUENCE: 166

Met Lys Val Ala Val Leu Gly Ala Ala Gly Gly Val Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Glu Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205
```

Ala Gly Thr Glu Val Val Glu Ala Lys Ala Gly Gly Ser Ala Thr
    210             215                 220

Leu Ser Met Gly Gln Ala Ala Arg Phe Gly Leu Ser Leu Val Arg
225             230                 235                 240

Ala Leu Gln Gly Glu Gln Gly Val Val Glu Cys Ala Tyr Val Glu Gly
            245                 250                 255

Asp Gly Gln Tyr Ala Arg Phe Phe Ser Gln Pro Leu Leu Gly Lys
            260                 265                 270

Asn Gly Val Glu Glu Arg Lys Ser Ile Gly Thr Leu Ser Ala Phe Glu
            275                 280                 285

Gln Asn Ala Leu Glu Gly Met Leu Asp Thr Leu Lys Lys Asp Ile Ala
            290                 295                 300

Leu Gly Glu Glu Phe Val Asn Lys
305             310

<210> SEQ ID NO 167
<211> LENGTH: 939
<212> TYPE: DNA
<213> ORGANISM: Escherichia coli

<400> SEQUENCE: 167
atgaaagtcg cagtcctcgg cgctgctggc ggtattggcc aggcgcttgc actactgtta      60
aaacccaac tgccttcagg ttcagaactc tctctgtatg atatcgctcc agtgactccc      120
ggtgtggctg tcgatctgag ccatatccct actgctgtga aaatcaaagg tttttctggt      180
gaagatgcga ctccggcgct ggaaggcgca gatgtcgttc ttatctctgc aggcgtagcg      240
gctaaacccg ggatggatcg ttccgacctg tttaacgtta acgccggcat cgtgaaaaac      300
ctggtacagc aagttgcgaa acctgcccg aaagcgtgca ttggtattat cactaacccg      360
gttaacacca cagttgcaat tgctgctgaa gtgctgaaaa agccggtgt ttatgacaaa      420
aacaaactgt tcggcgttac cacgctggat atcattcgtt ccaacacctt tgttgcggaa      480
ctgaaaggca acagccagg cgaagttgaa gtgccggtta ttggcggcca ctctgatgtt      540
accattctgc cgctgctgtc acaggttcct ggcgttagtt ttaccgagca ggaagtggct      600
gatctgacca aacgcatcca gaacgcgggt actgaagtgg ttgaagcgaa ggccggtggc      660
gggtctgcaa ccctgtctat gggccaggca gctgcacgtt ttggtctgtc tctggttcgt      720
gcactgcagg gcgaacaagg cgttgtcgaa tgtgcctacg ttgaaggcga cggtcagtac      780
gcccgtttct tctctcaacc gctgctgctg ggtaaaaacg gcgtggaaga gcgtaaatct      840
atcggtaccc tgagcgcatt tgaacagaac gcgctggaag gtatgctgga tacgctgaag      900
aaagatatcg ccctgggcga agagttcgtt aataagtaa                             939

<210> SEQ ID NO 168
<211> LENGTH: 312
<212> TYPE: PRT
<213> ORGANISM: Escherichia coli

<400> SEQUENCE: 168

Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
                20                  25                  30

Tyr Asp Ile Ala Pro Val Thr Pro Gly Val Ala Val Asp Leu Ser His
            35                  40                  45

```
Ile Pro Thr Ala Val Lys Ile Lys Gly Phe Ser Gly Glu Asp Ala Thr
 50                  55                  60
Pro Ala Leu Glu Gly Ala Asp Val Val Leu Ile Ser Ala Gly Val Ala
 65                  70                  75                  80
Ala Lys Pro Gly Met Asp Arg Ser Asp Leu Phe Asn Val Asn Ala Gly
                 85                  90                  95
Ile Val Lys Asn Leu Val Gln Gln Val Ala Lys Thr Cys Pro Lys Ala
            100                 105                 110
Cys Ile Gly Ile Ile Thr Asn Pro Val Asn Thr Thr Val Ala Ile Ala
            115                 120                 125
Ala Glu Val Leu Lys Lys Ala Gly Val Tyr Asp Lys Asn Lys Leu Phe
130                 135                 140
Gly Val Thr Thr Leu Asp Ile Ile Arg Ser Asn Thr Phe Val Ala Glu
145                 150                 155                 160
Leu Lys Gly Lys Gln Pro Gly Glu Val Glu Val Pro Val Ile Gly Gly
                165                 170                 175
His Ser Asp Val Thr Ile Leu Pro Leu Leu Ser Gln Val Pro Gly Val
            180                 185                 190
Ser Phe Thr Glu Gln Glu Val Ala Asp Leu Thr Lys Arg Ile Gln Asn
            195                 200                 205
Ala Gly Thr Glu Val Val Glu Ala Lys Ala Gly Gly Gly Ser Ala Thr
210                 215                 220
Leu Ser Met Gly Gln Ala Ala Ala Arg Phe Gly Leu Ser Leu Val Arg
225                 230                 235                 240
Ala Leu Gln Gly Glu Gln Gly Val Val Glu Cys Ala Tyr Val Glu Gly
                245                 250                 255
Asp Gly Gln Tyr Ala Arg Phe Phe Ser Gln Pro Leu Leu Gly Lys
            260                 265                 270
Asn Gly Val Glu Glu Arg Lys Ser Ile Gly Thr Leu Ser Ala Phe Glu
            275                 280                 285
Gln Asn Ala Leu Glu Gly Met Leu Asp Thr Leu Lys Lys Asp Ile Ala
290                 295                 300
Leu Gly Glu Glu Phe Val Asn Lys
305                 310

<210> SEQ ID NO 169
<211> LENGTH: 939
<212> TYPE: DNA
<213> ORGANISM: Escherichia coli

<400> SEQUENCE: 169
atgaaagtcg cagtcctcgg cgctgctggc ggtattggcc aggcgcttgc actactgtta    60 aaacccaac tgccttcagg ttcagaactc tctctgtatg atatcgctcc agtgactccc    120
ggtgtggctg tcgatctgag ccatatccct actgctgtga aaatcaaagg ttttctggt    180 gaagatgcga ctccggcgct ggaaggcgca gatgtcgttc ttatctctgc aggcgtagcg    240
gctaaacccg ggatgtctcg ttccgacctg tttaacgtta acgccggcat cgtgaaaaac    300
ctggtacagc aagttgcgaa acctgcccg aaagcgtgca ttggtattat cactaacccg    360
gttaacacca cagttgcaat tgctgctgaa gtgctgaaaa agccggtgt ttatgacaaa    420 aacaaactgt tcggcgttac cacgctggat atcattcgtt ccaacacctt tgttgcggaa    480
ctgaaaggca acagccagg cgaagttgaa gtgccggtta ttggcggtca ctctggtgtt    540
accattctgc cgctgctgtc acaggttcct ggcgttagtt ttaccgagca ggaagtggct    600
```

```
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt    720
gcactgcagg gcgaacaagg cgttgtcgaa tgtgcctacg ttgaaggcga cggtcagtac    780
gcccgtttct tctctcaacc gctgctgctg ggtaaaaacg gcgtggaaga gcgtaaatct    840
atcggtaccc tgagcgcatt tgaacagaac gcgctggaag gtatgctgga tacgctgaag    900
aaagatatcg ccctgggcga agagttcgtt aataagtaa                           939
```

<210> SEQ ID NO 170
<211> LENGTH: 312
<212> TYPE: PRT
<213> ORGANISM: Escherichia coli

<400> SEQUENCE: 170

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Met Ser Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
    210                 215                 220

Leu Ser Met Gly Gln Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
    290                 295                 300

Leu Gly Glu Glu Phe Val Asn Lys
305                 310
```

<210> SEQ ID NO 171
<211> LENGTH: 939
<212> TYPE: DNA
<213> ORGANISM: Escherichia coli

<400> SEQUENCE: 171

```
atgaaagtcg cagtcctcgg cgctgctggc ggtattggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg ttttctggt      180
gaagatgcga ctccggcgct ggaaggcgca gatgtcgttc ttatctctgc aggcgtagcg     240
gctaaacccg ggatgtctcg ttccgacctg tttaacgtta acgccggcat cgtgaaaaac     300
ctggtacagc aagttgcgaa acctgcccg aaagcgtgca ttggtattat cactaacccg     360
gttaacacca cagttgcaat tgctgctgaa gtgctgaaaa agccggtgt ttatgacaaa      420
aacaaactgt tcggcgttac cacgctggat atcattcgtt ccaacacctt tgttgcggaa     480
ctgaaaggca acagccagg cgaagttgaa gtgccggtta ttggcggcca ctctgatgtt      540
accattctgc cgctgctgtc acaggttcct ggcgttagtt ttaccgagca ggaagtggct     600
gatctgacca aacgcatcca gaacgcgggt actgaagtgg ttgaagcgaa ggccggtggc     660
gggtctgcaa ccctgtctat gggccaggca gctgcacgtt ttggtctgtc tctggttcgt     720
gcactgcagg gcgaacaagg cgttgtcgaa tgtgcctacg ttgaaggcga cggtcagtac     780
gcccgttct tctctcaacc gctgctgctg ggtaaaaacg gcgtggaaga gcgtaaatct      840
atcggtaccc tgagcgcatt tgaacagaac gcgctggaag gtatgctgga tacgctgaag     900
aaagatatcg ccctgggcga agagttcgtt aataagtaa                            939
```

<210> SEQ ID NO 172
<211> LENGTH: 312
<212> TYPE: PRT
<213> ORGANISM: Escherichia coli

<400> SEQUENCE: 172

```
Met Lys Val Ala Val Leu Gly Ala Ala Gly Gly Ile Gly Gln Ala Leu
  1               5                  10                  15

Ala Leu Leu Leu Lys Thr Gln Leu Pro Ser Gly Ser Glu Leu Ser Leu
                 20                  25                  30

Tyr Asp Ile Ala Pro Val Thr Pro Gly Val Ala Val Asp Leu Ser His
             35                  40                  45

Ile Pro Thr Ala Val Lys Ile Lys Gly Phe Ser Gly Glu Asp Ala Thr
         50                  55                  60

Pro Ala Leu Glu Gly Ala Asp Val Val Leu Ile Ser Ala Gly Val Ala
 65                  70                  75                  80

Ala Lys Pro Gly Met Ser Arg Ser Asp Leu Phe Asn Val Asn Ala Gly
                 85                  90                  95

Ile Val Lys Asn Leu Val Gln Gln Val Ala Lys Thr Cys Pro Lys Ala
                100                 105                 110

Cys Ile Gly Ile Ile Thr Asn Pro Val Asn Thr Thr Val Ala Ile Ala
            115                 120                 125

Ala Glu Val Leu Lys Lys Ala Gly Val Tyr Asp Lys Asn Lys Leu Phe
        130                 135                 140

Gly Val Thr Thr Leu Asp Ile Ile Arg Ser Asn Thr Phe Val Ala Glu
145                 150                 155                 160
```

| | | | | | | | | | | | |
|---|---|---|---|---|---|---|---|---|---|---|---|
|Leu|Lys|Gly|Lys|Gln|Pro|Gly|Glu|Val|Glu|Val|Pro|Val|Ile|Gly|Gly|
| | | | |165| | | |170| | | |175| | | |

His Ser Asp Val Thr Ile Leu Pro Leu Leu Ser Gln Val Pro Gly Val
          180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
        210                 215                 220

Leu Ser Met Gly Gln Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
            275                 280                 285

Gln Asn Ala Leu Glu Gly Met Leu Asp Thr Leu Lys Lys Asp Ile Ala
        290                 295                 300

Leu Gly Glu Glu Phe Val Asn Lys
305                 310

<210> SEQ ID NO 173
<211> LENGTH: 1191
<212> TYPE: DNA
<213> ORGANISM: Escherichia coli

<400> SEQUENCE: 173

```
atgattattt ccgcagccag cgattatcgc gccgcagcgc aacgcattct gccgccgttc      60
ctgttccact atatggatgg tgtgcatat tctgaataca cgctgcgccg caacgtggaa     120
gatttgtcag aagtggcgct gcgccagcgt attctgaaaa acatgtccga cttaagcctg     180
gaaacgacgc tgtttaatga aaattgtcg atgccggtgg cactggctcc ggtgggtttg     240
tgtggcatgt atgcgcgtcg tggcgaagtt caggcagcca aagcggcgga cgcgcatggt     300
attccgttta ctctgtcgac gtgttccgtt tgcccgattg aagaagtcgc gccagccatc     360
aagcgcccaa tgtggttcca gctttatgta ctgcgcgatc gcggctttat gcgtaacgcg     420
ctggagcgag caaaagcagc gggttgttcg acgctggttt tcaccgtgga tatgccgaca     480
ccgggcgcac gctaccgtga tgcgcattca ggtatgagcg gcccgaacgc ggcaatgcgc     540
cgctacttgc aagcggtgac acatccgcaa tgggcgtggg atgtgggcct gaacggtcgt     600
ccacatgatt taggtaatat ctcagcttat ctcggcaaac cgaccggact ggaagattac     660
atcggctggc tggggaataa cttcgatccg tccatctcat ggaaagacct tgaatggatc     720
cgcgatttct gggatggccc gatggtgatc aaagggatcc tcgatccgga agatgcgcgc     780
gatgcagtac gttttggtgc tgatggaatt gtggtttcta accacggtgg ccgccagctg     840
gacggtgtac tctcttccgc ccgtgcactg cctgctattg cagatgcggt gaaaggtgat     900
atagccattc tggcggatag cggaattcgt aacgggcttg atgtcgtgcg tatgattgcg     960
ctcggtgccg acaccgtact gctgggtcgt gctttcttgt atgcgctggc aacagcgggc    1020
caggcgggtg tagctaacct gctaaatctg atcgaaaaag agatgaaagt ggcgatgacg    1080
ctgactggcg cgaaatcgat cagcgaaatt acgcaagatt cgctggtgca ggggctgggt    1140
aaagagttgc tgcggcact ggctcccatg gcgaagggca tgcggcata g              1191
```

<210> SEQ ID NO 174
<211> LENGTH: 396
<212> TYPE: PRT
<213> ORGANISM: Escherichia coli

<400> SEQUENCE: 174

Met Ile Ile Ser Ala Ala Ser Asp Tyr Arg Ala Ala Gln Arg Ile
1               5                   10                  15

Leu Pro Pro Phe Leu Phe His Tyr Met Asp Gly Gly Ala Tyr Ser Glu
            20                  25                  30

Tyr Thr Leu Arg Arg Asn Val Glu Asp Leu Ser Glu Val Ala Leu Arg
                35                  40                  45

Gln Arg Ile Leu Lys Asn Met Ser Asp Leu Ser Leu Glu Thr Thr Leu
    50                  55                  60

Phe Asn Glu Lys Leu Ser Met Pro Val Ala Leu Ala Pro Val Gly Leu
65                  70                  75                  80

Cys Gly Met Tyr Ala Arg Arg Gly Glu Val Gln Ala Ala Lys Ala Ala
                85                  90                  95

Asp Ala His Gly Ile Pro Phe Thr Leu Ser Thr Cys Ser Val Cys Pro
            100                 105                 110

Ile Glu Glu Val Ala Pro Ala Ile Lys Arg Pro Met Trp Phe Gln Leu
        115                 120                 125

Tyr Val Leu Arg Asp Arg Gly Phe Met Arg Asn Ala Leu Glu Arg Ala
    130                 135                 140

Lys Ala Ala Gly Cys Ser Thr Leu Val Phe Thr Val Asp Met Pro Thr
145                 150                 155                 160

Pro Gly Ala Arg Tyr Arg Asp Ala His Ser Gly Met Ser Gly Pro Asn
                165                 170                 175

Ala Ala Met Arg Arg Tyr Leu Gln Ala Val Thr His Pro Gln Trp Ala
            180                 185                 190

Trp Asp Val Gly Leu Asn Gly Arg Pro His Asp Leu Gly Asn Ile Ser
        195                 200                 205

Ala Tyr Leu Gly Lys Pro Thr Gly Leu Glu Asp Tyr Ile Gly Trp Leu
    210                 215                 220

Gly Asn Asn Phe Asp Pro Ser Ile Ser Trp Lys Asp Leu Glu Trp Ile
225                 230                 235                 240

Arg Asp Phe Trp Asp Gly Pro Met Val Ile Lys Gly Ile Leu Asp Pro
                245                 250                 255

Glu Asp Ala Arg Asp Ala Val Arg Phe Gly Ala Asp Gly Ile Val Val
            260                 265                 270

Ser Asn His Gly Gly Arg Gln Leu Asp Gly Val Leu Ser Ser Ala Arg
        275                 280                 285

Ala Leu Pro Ala Ile Ala Asp Ala Val Lys Gly Asp Ile Ala Ile Leu
    290                 295                 300

Ala Asp Ser Gly Ile Arg Asn Gly Leu Asp Val Val Arg Met Ile Ala
305                 310                 315                 320

Leu Gly Ala Asp Thr Val Leu Leu Gly Arg Ala Phe Leu Tyr Ala Leu
                325                 330                 335

Ala Thr Ala Gly Gln Ala Gly Val Ala Asn Leu Leu Asn Leu Ile Glu
            340                 345                 350

Lys Glu Met Lys Val Ala Met Thr Leu Thr Gly Ala Lys Ser Ile Ser
        355                 360                 365

Glu Ile Thr Gln Asp Ser Leu Val Gln Gly Leu Gly Lys Glu Leu Pro
    370                 375                 380

-continued

Ala Ala Leu Ala Pro Met Ala Lys Gly Asn Ala Ala
385                 390                 395

<210> SEQ ID NO 175
<211> LENGTH: 26
<212> TYPE: DNA
<213> ORGANISM: Artificial Sequence
<220> FEATURE:
<223> OTHER INFORMATION: Primer for amplification

<400> SEQUENCE: 175
catatgtctg aaattacttt gggtaa                                   26

<210> SEQ ID NO 176
<211> LENGTH: 24
<212> TYPE: DNA
<213> ORGANISM: Artificial Sequence
<220> FEATURE:
<223> OTHER INFORMATION: Primer for amplification

<400> SEQUENCE: 176
ggatccttat tgcttagcgt tggt                                     24

<210> SEQ ID NO 177
<211> LENGTH: 24
<212> TYPE: DNA
<213> ORGANISM: Artificial Sequence
<220> FEATURE:
<223> OTHER INFORMATION: Primer for amplification

<400> SEQUENCE: 177
catatgagtt atactgtcgg tacc                                     24

<210> SEQ ID NO 178
<211> LENGTH: 24
<212> TYPE: DNA
<213> ORGANISM: Artificial Sequence
<220> FEATURE:
<223> OTHER INFORMATION: Primer for amplification

<400> SEQUENCE: 178
ggatccctag aggagcttgt taac                                     24

<210> SEQ ID NO 179
<211> LENGTH: 49
<212> TYPE: DNA
<213> ORGANISM: Artificial Sequence
<220> FEATURE:
<223> OTHER INFORMATION: Primer for amplification

<400> SEQUENCE: 179
gttattgctg aaaccggtga ctctcagttc aatgcgcagc gcatgaagc           49

<210> SEQ ID NO 180
<211> LENGTH: 49
<212> TYPE: DNA
<213> ORGANISM: Artificial Sequence
<220> FEATURE:
<223> OTHER INFORMATION: Primer for amplification

<400> SEQUENCE: 180
gcttcatgcg ctgcgcattg aactgagagt caccggtttc agcaataac           49

<210> SEQ ID NO 181
<211> LENGTH: 54
<212> TYPE: DNA

<213> ORGANISM: Artificial Sequence
<220> FEATURE:
<223> OTHER INFORMATION: Primer for amplification

<400> SEQUENCE: 181
acggttattg ctgaaaccgg tgactctta ttcaatgcgc agcgcatgaa gctc        54

<210> SEQ ID NO 182
<211> LENGTH: 54
<212> TYPE: DNA
<213> ORGANISM: Artificial Sequence
<220> FEATURE:
<223> OTHER INFORMATION: Primer for amplification

<400> SEQUENCE: 182
gagcttcatg cgctgcgcat tgaataaaga gtcaccggtt tcagcaataa ccgt        54

<210> SEQ ID NO 183
<211> LENGTH: 48
<212> TYPE: DNA
<213> ORGANISM: Artificial Sequence
<220> FEATURE:
<223> OTHER INFORMATION: Primer for amplification

<400> SEQUENCE: 183
tatgaaatgc agtggaacca cattggttgg tcggtacctg ccgccttc        48

<210> SEQ ID NO 184
<211> LENGTH: 48
<212> TYPE: DNA
<213> ORGANISM: Artificial Sequence
<220> FEATURE:
<223> OTHER INFORMATION: Primer for amplification

<400> SEQUENCE: 184
gaaggcggca ggtaccgacc aaccaatgtg gttccactgc atttcata        48

<210> SEQ ID NO 185
<211> LENGTH: 42
<212> TYPE: DNA
<213> ORGANISM: Artificial Sequence
<220> FEATURE:
<223> OTHER INFORMATION: Primer for amplification

<400> SEQUENCE: 185
ggacaaccgc tgtggtccag tattgggtat acgtttccag cg        42

<210> SEQ ID NO 186
<211> LENGTH: 42
<212> TYPE: DNA
<213> ORGANISM: Artificial Sequence
<220> FEATURE:
<223> OTHER INFORMATION: Primer for amplification

<400> SEQUENCE: 186
cgctggaaac gtatacccaa tactggacca cagcggttgt cc        42

<210> SEQ ID NO 187
<211> LENGTH: 49
<212> TYPE: DNA
<213> ORGANISM: Artificial Sequence
<220> FEATURE:
<223> OTHER INFORMATION: Primer for amplification

<400> SEQUENCE: 187
tttgctttat cattaataat gacggctaca caatcgagcg cgaaattca        49

<210> SEQ ID NO 188
<211> LENGTH: 49
<212> TYPE: DNA
<213> ORGANISM: Artificial Sequence
<220> FEATURE:
<223> OTHER INFORMATION: Primer for amplification

<400> SEQUENCE: 188
tgaatttcgc gctcgattgt gtagccgtca ttattaatga taaagcaaa        49

<210> SEQ ID NO 189
<211> LENGTH: 1707
<212> TYPE: DNA
<213> ORGANISM: Zymomonas mobilis

<400> SEQUENCE: 189
atgagttata ctgtcggtac ctatttagcg gagcggcttg tccagattgg tctcaagcat        60
cacttcgcag tcgcgggcga ctacaacctc gtccttcttg acaacctgct tttgaacaaa       120
aacatggagc aggtttattg ctgtaacgaa ctgaactgcg gtttcagtgc agaaggttat       180
gctcgtgcca aggcgcagc agcagccgtc gttacctaca cgtcggtgc gctttccgca        240
tttgatgcta tcggtggcgc ctatgcagaa accttccgg ttatcctgat ctccggtgct       300
ccgaacaaca atgatcacgc tgctggtcac gtgttcatc acgctcttgg caaaaccgac       360
tatcactatc agttggaaat ggccaagaac atcacggccg ccgctgaagc gatttacacc       420
ccggaagaag ctccggctaa aatcgatcac gtgattaaaa ctgctcttcg tgagaagaag       480
ccggtttatc tcgaaatcgc ttgcaacatt gcttccatgc cctgcgccgc tcctggaccg       540
gcaagcgcat tgttcaatga cgaagccagc gacgaagctt ctttgaatgc agcggttgaa       600
gaaaccctga aattcatcgc caaccgcgac aaagttgccg tcctcgtcgg cagcaagctg       660
cgcgcagctg gtgctgaaga gctgctgtc aaatttgctg atgctctcgg tggcgcagtt       720
gctaccatgg ctgctgcaaa aagcttcttt ccagaagaaa acccgcatta catcggcacc       780
tcatggggtg aagtcagcta tccgggcgtt gaaaagacga tgaaagaagc cgatgcggtt       840
atcgctctgg ctcctgtctt caacgactac tccaccactg gttggacgga tattcctgat       900
cctaagaaac tggttctcgc tgaaccgcgt tctgtcgtcg ttaacggcat tcgcttcccc       960
agcgtccatc tgaaagacta tctgacccgt ttggctcaga agtttccaa gaaaaccggt      1020
gcattggact tcttcaaatc cctcaatgca ggtgaactga gaaagccgc tccggctgat      1080
ccgagtgctc cgttggtcaa cgcagaaatc gcccgccaag tcgaagctct tctgaccccg      1140
aacacgacgg ttattgctga accggtgac tctgacttca tgcgcagcg catgaagctc      1200
ccgaacggtc ctcgcgttga atatgaaatg cagtggggtc acattggttg gtccgttcct      1260
gccgccttcg gttatgccgt cggtgctccg gaacgtcgca acatcctcat ggttggtgat      1320
ggttccttcc agctgacggc tcaggaagtc gctcagatgg ttcgcctgaa actgccggtt      1380
atcatcttct tgatcaataa ctatggttac accatcgaag ttatgatcca tgatggtccg      1440
tacaacaaca tcaagaactg ggattatgcc ggtctgatgg aagtgttcaa cggtaacggt      1500
ggttatgaca gcgtgctgg taaggcctg aaggctaaaa ccggtggcga actggcagaa      1560
gctatcaagg ttgctctggc aaacaccgac ggcccaaccc tgatcgaatg cttcatcggt      1620
cgtgaagact gcactgaaga attggtcaaa tgggtaagc gcgttgctgc cgccaacagc      1680
cgtaagcctg ttaacaagct cctctag                                         1707

-continued

```
<210> SEQ ID NO 190
<211> LENGTH: 568
<212> TYPE: PRT
<213> ORGANISM: Zymomonas mobilis

<400> SEQUENCE: 190
```

| | | | | | | | | | | | | | | |
|---|---|---|---|---|---|---|---|---|---|---|---|---|---|---|
| Met | Ser | Tyr | Thr | Val | Gly | Thr | Tyr | Leu | Ala | Glu | Arg | Leu | Val | Gln | Ile |
| 1 | | | | 5 | | | | | 10 | | | | | 15 | |
| Gly | Leu | Lys | His | His | Phe | Ala | Val | Ala | Gly | Asp | Tyr | Asn | Leu | Val | Leu |
| | | | 20 | | | | | 25 | | | | | 30 | | |
| Leu | Asp | Asn | Leu | Leu | Asn | Lys | Asn | Met | Glu | Gln | Val | Tyr | Cys | Cys |
| | | 35 | | | | | 40 | | | | | 45 | | |
| Asn | Glu | Leu | Asn | Cys | Gly | Phe | Ser | Ala | Glu | Gly | Tyr | Ala | Arg | Ala | Lys |
| | 50 | | | | | 55 | | | | | 60 | | | | |
| Gly | Ala | Ala | Ala | Val | Val | Thr | Tyr | Ser | Val | Gly | Ala | Leu | Ser | Ala |
| 65 | | | | | 70 | | | | | 75 | | | | | 80 |
| Phe | Asp | Ala | Ile | Gly | Gly | Ala | Tyr | Ala | Glu | Asn | Leu | Pro | Val | Ile | Leu |
| | | | | 85 | | | | | 90 | | | | | 95 | |
| Ile | Ser | Gly | Ala | Pro | Asn | Asn | Asn | Asp | His | Ala | Ala | Gly | His | Val | Leu |
| | | | 100 | | | | | 105 | | | | | 110 | | |
| His | His | Ala | Leu | Gly | Lys | Thr | Asp | Tyr | His | Tyr | Gln | Leu | Glu | Met | Ala |
| | | | 115 | | | | | 120 | | | | | 125 | | |
| Lys | Asn | Ile | Thr | Ala | Ala | Ala | Glu | Ala | Ile | Tyr | Thr | Pro | Glu | Glu | Ala |
| | 130 | | | | | 135 | | | | | 140 | | | | |
| Pro | Ala | Lys | Ile | Asp | His | Val | Ile | Lys | Thr | Ala | Leu | Arg | Glu | Lys | Lys |
| 145 | | | | | 150 | | | | | 155 | | | | | 160 |
| Pro | Val | Tyr | Leu | Glu | Ile | Ala | Cys | Asn | Ile | Ala | Ser | Met | Pro | Cys | Ala |
| | | | | 165 | | | | | 170 | | | | | 175 | |
| Ala | Pro | Gly | Pro | Ala | Ser | Ala | Leu | Phe | Asn | Asp | Glu | Ala | Ser | Asp | Glu |
| | | | 180 | | | | | 185 | | | | | 190 | | |
| Ala | Ser | Leu | Asn | Ala | Ala | Val | Glu | Glu | Thr | Leu | Lys | Phe | Ile | Ala | Asn |
| | | | 195 | | | | | 200 | | | | | 205 | | |
| Arg | Asp | Lys | Val | Ala | Val | Leu | Val | Gly | Ser | Lys | Leu | Arg | Ala | Ala | Gly |
| | 210 | | | | | 215 | | | | | 220 | | | | |
| Ala | Glu | Glu | Ala | Ala | Val | Lys | Phe | Ala | Asp | Ala | Leu | Gly | Gly | Ala | Val |
| 225 | | | | | 230 | | | | | 235 | | | | | 240 |
| Ala | Thr | Met | Ala | Ala | Ala | Lys | Ser | Phe | Phe | Pro | Glu | Glu | Asn | Pro | His |
| | | | | 245 | | | | | 250 | | | | | 255 | |
| Tyr | Ile | Gly | Thr | Ser | Trp | Gly | Glu | Val | Ser | Tyr | Pro | Gly | Val | Glu | Lys |
| | | | 260 | | | | | 265 | | | | | 270 | | |
| Thr | Met | Lys | Glu | Ala | Asp | Ala | Val | Ile | Ala | Leu | Ala | Pro | Val | Phe | Asn |
| | | | 275 | | | | | 280 | | | | | 285 | | |
| Asp | Tyr | Ser | Thr | Thr | Gly | Trp | Thr | Asp | Ile | Pro | Asp | Pro | Lys | Lys | Leu |
| | 290 | | | | | 295 | | | | | 300 | | | | |
| Val | Leu | Ala | Glu | Pro | Arg | Ser | Val | Val | Asn | Gly | Ile | Arg | Phe | Pro |
| 305 | | | | | 310 | | | | | 315 | | | | | 320 |
| Ser | Val | His | Leu | Lys | Asp | Tyr | Leu | Thr | Arg | Leu | Ala | Gln | Lys | Val | Ser |
| | | | | 325 | | | | | 330 | | | | | 335 | |
| Lys | Lys | Thr | Gly | Ala | Leu | Asp | Phe | Phe | Lys | Ser | Leu | Asn | Ala | Gly | Glu |
| | | | 340 | | | | | 345 | | | | | 350 | | |
| Leu | Lys | Lys | Ala | Ala | Pro | Ala | Asp | Pro | Ser | Ala | Pro | Leu | Val | Asn | Ala |
| | | | 355 | | | | | 360 | | | | | 365 | | |
| Glu | Ile | Ala | Arg | Gln | Val | Glu | Ala | Leu | Leu | Thr | Pro | Asn | Thr | Thr | Val |
| | 370 | | | | | 375 | | | | | 380 | | | | |

```
Ile Ala Glu Thr Gly Asp Ser Gln Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
    450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565

<210> SEQ ID NO 191
<211> LENGTH: 1707
<212> TYPE: DNA
<213> ORGANISM: Zymomonas mobilis

<400> SEQUENCE: 191
atgagttata ctgtcggtac ctatttagcg gagcggcttg tccagattgg tctcaagcat     60
cacttcgcag tcgcgggcga ctacaacctc gtccttcttg acaacctgct tttgaacaaa    120
aacatggagc aggtttattg ctgtaacgaa ctgaactgcg gtttcagtgc agaaggttat    180
gctcgtgcca aggcgcagc agcagccgtc gttacctaca gcgtcggtgc gctttccgca    240
tttgatgcta tcggtggcgc ctatgcagaa accttccgg ttatcctgat ctccggtgct    300
ccgaacaaca tgatcacgc tgctggtcac gtgttgcatc acgctcttgg caaaaccgac    360
tatcactatc agttggaaat ggccaagaac atcacggccg ccgctgaagc gatttacacc    420
ccggaagaag ctccggctaa aatcgatcac gtgattaaaa ctgctcttcg tgagaagaag    480
ccggtttatc tcgaaatcgc ttgcaacatt gcttccatgc cctgcgccgc tcctggaccg    540
gcaagcgcat tgttcaatga cgaagccagc gacgaagctt ctttgaatgc agcggttgaa    600 gaaacccctga aattcatcgc caaccgcgac aaagttgccg tcctcgtcgg cagcaagctg    660
cgcgcagctg gtgctgaaga agctgctgtc aaatttgctg atgctctcgg tggcgcagtt    720
gctaccatgg ctgctgcaaa aagcttcttt ccagaagaaa accgcattta catcggcacc    780
tcatggggtg aagtcagcta tccgggcgtt gaaagacga tgaaagaagc cgatgcggtt    840
atcgctctgg ctcctgtctt caacgactac tccaccactg gttggacgga tattcctgat    900
cctaagaaac tggttctcgc tgaaccgcgt ctgtcgtcg ttaacggcat cgcttcccc    960 agcgtccatc tgaaagacta tctgacccgt ttggctcaga aagtttccaa gaaaaccggt    1020
```

```
gcattggact tcttcaaatc cctcaatgca ggtgaactga agaaagccgc tccggctgat    1080
ccgagtgctc cgttggtcaa cgcagaaatc gcccgccaag tcgaagctct tctgaccccg    1140
aacacgacgg ttattgctga aaccggtgac tctttattca atgcgcagcg catgaagctc    1200
ccgaacggtg ctcgcgttga atatgaaatg cagtggggtc acattggttg gtccgttcct    1260
gccgccttcg gttatgccgt cggtgctccg gaacgtcgca acatcctcat ggttggtgat    1320
ggttccttcc agctgacggc tcaggaagtc gctcagatgg ttcgcctgaa actgccggtt    1380
atcatcttct tgatcaataa ctatggttac accatcgaag ttatgatcca tgatggtccg    1440
tacaacaaca tcaagaactg ggattatgcc ggtctgatgg aagtgttcaa cggtaacggt    1500
ggttatgaca gcggtgctgg taaaggcctg aaggctaaaa ccggtggcga actggcagaa    1560
gctatcaagg ttgctctggc aaacaccgac ggcccaaccc tgatcgaatg cttcatcggt    1620
cgtgaagact gcactgaaga attggtcaaa tggggtaagc gcgttgctgc cgccaacagc    1680
cgtaagcctg ttaacaagct cctctag                                       1707
```

<210> SEQ ID NO 192
<211> LENGTH: 568
<212> TYPE: PRT
<213> ORGANISM: Zymomonas mobilis

<400> SEQUENCE: 192

```
Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Glu Ala Ala Val Lys Phe Ala Asp Ala Leu Gly Gly Ala Val
225                 230                 235                 240

Ala Thr Met Ala Ala Ala Lys Ser Phe Phe Pro Glu Glu Asn Pro His
                245                 250                 255
```

Tyr Ile Gly Thr Ser Trp Gly Glu Val Ser Tyr Pro Gly Val Glu Lys
                260                 265                 270

Thr Met Lys Glu Ala Asp Ala Val Ile Ala Leu Ala Pro Val Phe Asn
            275                 280                 285

Asp Tyr Ser Thr Thr Gly Trp Thr Asp Ile Pro Asp Pro Lys Lys Leu
        290                 295                 300

Val Leu Ala Glu Pro Arg Ser Val Val Asn Gly Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365

Glu Ile Ala Arg Gln Val Glu Ala Leu Leu Thr Pro Asn Thr Thr Val
    370                 375                 380

Ile Ala Glu Thr Gly Asp Ser Leu Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
    450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565

<210> SEQ ID NO 193
<211> LENGTH: 1707
<212> TYPE: DNA
<213> ORGANISM: Zymomonas mobilis

<400> SEQUENCE: 193
atgagttata ctgtcggtac ctatttagcg gagcggcttg tccagattgg tctcaagcat    60
cacttcgcag tcgcgggcga ctacaacctc gtccttcttg acaacctgct tttgaacaaa   120
aacatggagc aggtttattg ctgtaacgaa ctgaactgcg gtttcagtgc agaaggttat   180
gctcgtgcca aggcgcagc agcagccgtc gttacctaca cgtcggtgc gctttccgca   240 tttgatgcta tcggtggcgc ctatgcagaa aaccttccgg ttatcctgat ctccggtgct   300

```
ccgaacaaca atgatcacgc tgctggtcac gtgttgcatc acgctcttgg caaaaccgac    360
tatcactatc agttggaaat ggccaagaac atcacggccg ccgctgaagc gatttacacc    420
ccggaagaag ctccggctaa aatcgatcac gtgattaaaa ctgctcttcg tgagaagaag    480
ccggtttatc tcgaaatcgc ttgcaacatt gcttccatgc cctgcgccgc tcctggaccg    540
gcaagcgcat tgttcaatga cgaagccagc gacgaagctt ctttgaatgc agcggttgaa    600
gaaaccctga aattcatcgc caaccgcgac aaagttgccg tcctcgtcgg cagcaagctg    660
cgcgcagctg gtgctgaaga agctgctgtc aaatttgctg atgctctcgg tggcgcagtt    720
gctaccatgg ctgctgcaaa aagcttcttt ccagaagaaa acccgcatta tcatcggcacc    780 tcatggggtg aagtcagcta tccgggcgtt gaaaagacga tgaaagaagc cgatgcggtt    840
atcgctctgg ctcctgtctt caacgactac tccaccactg gttggacgga tattcctgat    900
cctaagaaac tggttctcgc tgaaccgcgt tctgtcgtcg ttaacggcat tcgcttcccc    960
agcgtccatc tgaaagacta tctgacccgt ttggctcaga agtttccaa gaaaaccggt   1020 gcattggact tcttcaaatc cctcaatgca ggtgaactga agaaagccgc tccggctgat   1080
ccgagtgctc cgttggtcaa cgcagaaatc gcccgccaag tcgaagctct tctgaccccg   1140
aacacgacgg ttattgctga aaccggtgac tcttggttca atgctcagcg catgaagctc   1200
ccgaacggtg ctcgcgttga atatgaaatg cagtggaacc acattggttg gtcggtacct   1260
gccgccttcg gttatgccgt cggtgctccg gaacgtcgca acatcctcat ggttggtgat   1320
ggttccttcc agctgacggc tcaggaagtc gctcagatgg ttcgcctgaa actgccggtt   1380
atcatcttct tgatcaataa ctatggttac accatcgaag ttatgatcca tgatggtccg   1440
tacaacaaca tcaagaactg ggattatgcc ggtctgatgg aagtgttcaa cggtaacggt   1500
ggttatgaca cgcgtgctgg taaaggcctg aaggctaaaa ccgtggcga actggcagaa   1560 gctatcaagg ttgctctggc aaacaccgac ggcccaaccc tgatcgaatg cttcatcggt   1620
cgtgaagact gcactgaaga attggtcaaa tgggtaagc gcgttgctgc cgccaacagc   1680
cgtaagcctg ttaacaagct cctctag                                       1707
```

<210> SEQ ID NO 194
<211> LENGTH: 568
<212> TYPE: PRT
<213> ORGANISM: Zymomonas mobilis

<400> SEQUENCE: 194

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

-continued

```
Lys Asn Ile Thr Ala Ala Ala Glu Ala Ile Tyr Thr Pro Glu Glu Ala
    130                 135                 140
Pro Ala Lys Ile Asp His Val Ile Lys Thr Ala Leu Arg Glu Lys Lys
145                 150                 155                 160
Pro Val Tyr Leu Glu Ile Ala Cys Asn Ile Ala Ser Met Pro Cys Ala
                165                 170                 175
Ala Pro Gly Pro Ala Ser Ala Leu Phe Asn Asp Glu Ala Ser Asp Glu
            180                 185                 190
Ala Ser Leu Asn Ala Ala Val Glu Glu Thr Leu Lys Phe Ile Ala Asn
        195                 200                 205
Arg Asp Lys Val Ala Val Leu Val Gly Ser Lys Leu Arg Ala Ala Gly
    210                 215                 220
Ala Glu Glu Ala Ala Val Lys Phe Ala Asp Ala Leu Gly Gly Ala Val
225                 230                 235                 240
Ala Thr Met Ala Ala Ala Lys Ser Phe Phe Pro Glu Glu Asn Pro His
                245                 250                 255
Tyr Ile Gly Thr Ser Trp Gly Glu Val Ser Tyr Pro Gly Val Glu Lys
            260                 265                 270
Thr Met Lys Glu Ala Asp Ala Val Ile Ala Leu Ala Pro Val Phe Asn
        275                 280                 285
Asp Tyr Ser Thr Thr Gly Trp Thr Asp Ile Pro Asp Pro Lys Lys Leu
    290                 295                 300
Val Leu Ala Glu Pro Arg Ser Val Val Asn Gly Ile Arg Phe Pro
305                 310                 315                 320
Ser Val His Leu Lys Asp Tyr Leu Thr Arg Leu Ala Gln Lys Val Ser
                325                 330                 335
Lys Lys Thr Gly Ala Leu Asp Phe Phe Lys Ser Leu Asn Ala Gly Glu
            340                 345                 350
Leu Lys Lys Ala Ala Pro Ala Asp Pro Ser Ala Pro Leu Val Asn Ala
        355                 360                 365
Glu Ile Ala Arg Gln Val Glu Ala Leu Leu Thr Pro Asn Thr Thr Val
    370                 375                 380
Ile Ala Glu Thr Gly Asp Ser Trp Phe Asn Ala Gln Arg Met Lys Leu
385                 390                 395                 400
Pro Asn Gly Ala Arg Val Glu Tyr Glu Met Gln Trp Asn His Ile Gly
                405                 410                 415
Trp Ser Val Pro Ala Ala Phe Gly Tyr Ala Val Gly Ala Pro Glu Arg
            420                 425                 430
Arg Asn Ile Leu Met Val Gly Asp Gly Ser Phe Gln Leu Thr Ala Gln
        435                 440                 445
Glu Val Ala Gln Met Val Arg Leu Lys Leu Pro Val Ile Ile Phe Leu
    450                 455                 460
Ile Asn Asn Tyr Gly Tyr Thr Ile Glu Val Met Ile His Asp Gly Pro
465                 470                 475                 480
Tyr Asn Asn Ile Lys Asn Trp Asp Tyr Ala Gly Leu Met Glu Val Phe
                485                 490                 495
Asn Gly Asn Gly Gly Tyr Asp Ser Gly Ala Gly Lys Gly Leu Lys Ala
            500                 505                 510
Lys Thr Gly Gly Glu Leu Ala Glu Ala Ile Lys Val Ala Leu Ala Asn
        515                 520                 525
Thr Asp Gly Pro Thr Leu Ile Glu Cys Phe Ile Gly Arg Glu Asp Cys
    530                 535                 540
```

Thr Glu Glu Leu Val Lys Trp Gly Lys Arg Val Ala Ala Ala Asn Ser
545                 550                 555                 560

Arg Lys Pro Val Asn Lys Leu Leu
            565

<210> SEQ ID NO 195
<211> LENGTH: 1644
<212> TYPE: DNA
<213> ORGANISM: Lactococcus lactis

<400> SEQUENCE: 195

| | | | | | |
|---|---|---|---|---|---|
| atgtataccg | ttggggatta | tctgctggat | cgcttgcatg | agttaggcat | tgaagaaatt | 60 |
| ttcggcgtac | ctggtgacta | taatctccag | tttcttgatc | agatcatctc | acgcgaagat | 120 |
| atgaaatgga | ttggtaatgc | caatgaactg | aatgccagct | atatggctga | cggttatgcg | 180 |
| cgtactaaga | aagcggcagc | ctttctgacg | acctttggcg | taggcgagtt | aagcgccatt | 240 |
| aacggactcg | ctggctccta | tgctgagaac | ttgccggtag | tcgaaatcgt | gggctctcca | 300 |
| acgtccaaag | tacaaaatga | cggaaaattc | gtgcatcata | ccctcgcgga | tggtgacttt | 360 |
| aaacacttta | tgaaaatgca | tgaaccggta | acagccgcgc | gtaccctgct | gactgcggag | 420 |
| aatgcgacct | acgaaattga | tcgcgtttta | agccagctgt | taaaagaacg | caaacccgtc | 480 |
| tacatcaatc | tgcctgttga | tgtagcagcc | gctaaagctg | agaaaccggc | gcttagtctg | 540 |
| gaaaaggagt | cgagcaccac | caatacgacc | gaacaagtga | ttctgtccaa | aattgaagaa | 600 |
| tcccttaaaa | acgcacagaa | accggtggtt | attgccgggc | atgaagtgat | tagctttggg | 660 |
| ttggagaaaa | ccgtcactca | gttcgtcagt | gaaaccaaat | tgccgattac | cacgctgaac | 720 |
| tttggtaaga | gcgcggttga | cgagagcttg | ccatcgttcc | tggggatcta | caacggtaag | 780 |
| ctgtctgaaa | tttcgctgaa | gaactttgtg | gaatcagcgg | attcatttt | gatgctgggt | 840 |
| gtgaaactca | cggattcttc | gactggggca | tttacccacc | atctggacga | aaacaaaatg | 900 |
| atcagcttga | acatcgacga | gggcattatc | ttcaacaagg | tggtcgaaga | tttcgatttt | 960 |
| cgtgcagtgg | tgtccagtct | ctcggaactg | aagggtattg | aatatgaggg | tcagtacatc | 1020 |
| gataaacagt | atgaagagtt | catcccgtca | tctgcccctc | tgagccaaga | ccgcctttgg | 1080 |
| caggcagtgg | aaagcctcac | acagtccaat | gaaacgatcg | ttgcagaaca | aggtactagt | 1140 |
| ttctttggcg | caagcacgat | cttcctgaaa | tcgaactcac | ggttcatcgg | acaaccgctg | 1200 |
| tggtccagta | ttgggtatac | gtttccagcg | gcgttaggat | cacagattgc | ggataaggaa | 1260 |
| agtcgtcacc | tgttattcat | tggcgatggt | tctcttcaac | ttacggtcca | ggaactgggc | 1320 |
| ctgtccattc | gcgagaaact | gaacccgatt | tgctttatca | tcaacaatga | cggctacaca | 1380 |
| gtggagcgcg | aaattcacgg | cccgacccag | agttacaatg | acattcccat | gtggaactac | 1440 |
| agcaaattac | cagaaacctt | tggtgccaca | gaagatcgtg | ttgtctctaa | aatcgtgcgc | 1500 |
| actgagaacg | aatttgtttc | ggttatgaaa | gaagcgcaag | cggatgtgaa | tcggatgtat | 1560 |
| tggattgaac | tggtcctgga | gaagaagat | gccccgaaac | tgctgaagaa | aatgggcaaa | 1620 |
| ctgtttgctg | aacagaacaa | ataa | | | | 1644 |

<210> SEQ ID NO 196
<211> LENGTH: 547
<212> TYPE: PRT
<213> ORGANISM: Lactococcus lactis

<400> SEQUENCE: 196

Met Tyr Thr Val Gly Asp Tyr Leu Leu Asp Arg Leu His Glu Leu Gly

-continued

```
1               5                   10                  15
Ile Glu Glu Ile Phe Gly Val Pro Gly Asp Tyr Asn Leu Gln Phe Leu
                20                  25                  30

Asp Gln Ile Ile Ser Arg Glu Asp Met Lys Trp Ile Gly Asn Ala Asn
                35                  40                  45

Glu Leu Asn Ala Ser Tyr Met Ala Asp Gly Tyr Ala Arg Thr Lys Lys
 50                 55                  60

Ala Ala Ala Phe Leu Thr Thr Phe Gly Val Gly Glu Leu Ser Ala Ile
 65                 70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
                100                 105                 110

His Thr Leu Ala Asp Gly Asp Phe Lys His Phe Met Lys Met His Glu
                115                 120                 125

Pro Val Thr Ala Ala Arg Thr Leu Leu Thr Ala Glu Asn Ala Thr Tyr
 130                135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Asn Thr Thr Glu Gln
                180                 185                 190

Val Ile Leu Ser Lys Ile Glu Glu Ser Leu Lys Asn Ala Gln Lys Pro
                195                 200                 205

Val Val Ile Ala Gly His Glu Val Ile Ser Phe Gly Leu Glu Lys Thr
                210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asp Glu Asn Lys Met Ile Ser Leu Asn
                290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Phe Ile Pro Ser Ser Ala
                340                 345                 350

Pro Leu Ser Gln Asp Arg Leu Trp Gln Ala Val Glu Ser Leu Thr Gln
                355                 360                 365

Ser Asn Glu Thr Ile Val Ala Glu Gln Gly Thr Ser Phe Phe Gly Ala
                370                 375                 380

Ser Thr Ile Phe Leu Lys Ser Asn Ser Arg Phe Ile Gly Gln Pro Leu
385                 390                 395                 400

Trp Ser Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430
```

```
Gln Leu Thr Val Gln Glu Leu Gly Leu Ser Ile Arg Glu Lys Leu Asn
            435                 440                 445
Pro Ile Cys Phe Ile Ile Asn Asp Gly Tyr Thr Val Glu Arg Glu
        450                 455                 460
Ile His Gly Pro Thr Gln Ser Tyr Asn Asp Ile Pro Met Trp Asn Tyr
465                 470                 475                 480
Ser Lys Leu Pro Glu Thr Phe Gly Ala Thr Glu Asp Arg Val Val Ser
                485                 490                 495
Lys Ile Val Arg Thr Glu Asn Glu Phe Val Ser Val Met Lys Glu Ala
                500                 505                 510
Gln Ala Asp Val Asn Arg Met Tyr Trp Ile Glu Leu Val Leu Glu Lys
                515                 520                 525
Glu Asp Ala Pro Lys Leu Leu Lys Lys Met Gly Lys Leu Phe Ala Glu
            530                 535                 540
Gln Asn Lys
545

<210> SEQ ID NO 197
<211> LENGTH: 1644
<212> TYPE: DNA
<213> ORGANISM: Lactococcus lactis

<400> SEQUENCE: 197
atgtataccg ttggggatta tctgctggat cgcttgcatg agttaggcat tgaagaaatt      60
ttcggcgtac ctggtgacta taatctccag tttcttgatc agatcatctc acgcgaagat     120
atgaaatgga ttggtaatgc caatgaactg aatgccagct atatggctga cggttatgcg     180
cgtactaaga aagcggcagc ctttctgacg acctttggcg taggcgagtt aagcgccatt     240
aacggactcg ctggctccta tgctgagaac ttgccggtag tcgaaatcgt gggctctcca     300
acgtccaaag tacaaaatga cggaaaaatt gtgcatcata ccctcgcgga tggtgacttt     360 aaacactttta tgaaaatgca tgaaccggta acagccgcgc gtaccctgct gactgcggag     420
aatgcgacct acgaaattga tcgcgttttta agccagctgt taaaagaacg caaacccgtc     480
tacatcaatc tgcctgttga tgtagcagcc gctaaagctg agaaaccggc gcttagtctg     540
gaaaaggagt cgagcaccac caatacgacc gaacaagtga ttctgtccaa aattgaagaa     600
tcccttaaaa acgcacagaa accggtggtt attgccgggc atgaagtgat tagctttggg     660
ttggagaaaa ccgtcactca gttcgtcagt gaaaccaaat tgccgattac cacgctgaac     720
tttggtaaga gcgcggttga cgagagcttg ccatcgttcc tggggatcta caacggtaag     780
ctgtctgaaa tttcgctgaa gaactttgtg gaatcagcgg atttcatttt tgatgctggt     840
gtgaaactca cggattcttc gactggggca tttacccacc atctggacga aaacaaaatg     900
atcagcttga acatcgacga gggcattatc ttcaacaagg tggtcgaaga tttcgatttt     960
cgtgcagtgg tgtccagtct ctcggaactg aagggtattg aatatgaggg tcagtacatc    1020
gataaacagt atgaagagtt catcccgtca tctgcccctc tgagccaaga ccgcctttgg    1080
caggcagtgg aaagcctcac acagtccaat gaaacgatcg ttgcagaaca aggtactagt    1140
ttctttggcg caagcacgat cttcctgaaa tcgaactcac ggttcatcgg acaaccgctg    1200
tggggcagta ttggctatac gtttccagcg gcgttaggat cacagattgc ggataaggaa    1260
agtcgtcacc tgttattcat tggcgatggt tctcttcaac ttcggtcca ggaactgggc    1320 ctgtccattc gcgagaaact gaacccgatt tgctttatca ttaataatga cggctacaca    1380
```

```
atcgagcgcg aaattcacgg cccgacccag agttacaatg acattcccat gtggaactac    1440
agcaaattac cagaaaccct tggtgccaca gaagatcgtg ttgtctctaa aatcgtgcgc    1500
actgagaacg aatttgtttc ggttatgaaa gaagcgcaag cggatgtgaa tcggatgtat    1560
tggattgaac tggtcctgga gaaagaagat gccccgaaac tgctgaagaa aatgggcaaa    1620
ctgtttgctg aacagaacaa ataa                                           1644

<210> SEQ ID NO 198
<211> LENGTH: 547
<212> TYPE: PRT
<213> ORGANISM: Lactococcus lactis

<400> SEQUENCE: 198

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
```

```
                325                 330                 335
Gly Gln Tyr Ile Asp Lys Gln Tyr Glu Glu Phe Ile Pro Ser Ser Ala
            340                 345                 350
Pro Leu Ser Gln Asp Arg Leu Trp Gln Ala Val Glu Ser Leu Thr Gln
        355                 360                 365
Ser Asn Glu Thr Ile Val Ala Glu Gln Gly Thr Ser Phe Phe Gly Ala
    370                 375                 380
Ser Thr Ile Phe Leu Lys Ser Asn Ser Arg Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ser Ile Arg Glu Lys Leu Asn
        435                 440                 445
Pro Ile Cys Phe Ile Ile Asn Asn Asp Gly Tyr Thr Ile Glu Arg Glu
    450                 455                 460
Ile His Gly Pro Thr Gln Ser Tyr Asn Asp Ile Pro Met Trp Asn Tyr
465                 470                 475                 480
Ser Lys Leu Pro Glu Thr Phe Gly Ala Thr Glu Asp Arg Val Val Ser
                485                 490                 495
Lys Ile Val Arg Thr Glu Asn Glu Phe Val Ser Val Met Lys Glu Ala
            500                 505                 510
Gln Ala Asp Val Asn Arg Met Tyr Trp Ile Glu Leu Val Leu Glu Lys
        515                 520                 525
Glu Asp Ala Pro Lys Leu Leu Lys Lys Met Gly Lys Leu Phe Ala Glu
    530                 535                 540
Gln Asn Lys
545

<210> SEQ ID NO 199
<211> LENGTH: 34
<212> TYPE: DNA
<213> ORGANISM: Artificial Sequence
<220> FEATURE:
<223> OTHER INFORMATION: Primer for amplification

<400> SEQUENCE: 199
tatcgtgcta gcatgaacaa ctttaatctg caca                              34

<210> SEQ ID NO 200
<211> LENGTH: 46
<212> TYPE: DNA
<213> ORGANISM: Artificial Sequence
<220> FEATURE:
<223> OTHER INFORMATION: Primer for amplification

<400> SEQUENCE: 200
tataatgaat tcttagcggg cggcttcgta tacggcgg ctgaca                   46

<210> SEQ ID NO 201
<211> LENGTH: 67
<212> TYPE: DNA
<213> ORGANISM: Artificial Sequence
<220> FEATURE:
<223> OTHER INFORMATION: Primer for amplification

<400> SEQUENCE: 201
tataatgagc tctttaactt taagaaggag atataccatg aacaacttta atctgcacac  60
```

-continued cccaacc                                                              67

<210> SEQ ID NO 202
<211> LENGTH: 30
<212> TYPE: DNA
<213> ORGANISM: Artificial Sequence
<220> FEATURE:
<223> OTHER INFORMATION: Primer for amplification

<400> SEQUENCE: 202
tataatggat ccttagcggg cggcttcgta                                     30

<210> SEQ ID NO 203
<211> LENGTH: 52
<212> TYPE: DNA
<213> ORGANISM: Artificial Sequence
<220> FEATURE:
<223> OTHER INFORMATION: Primer for amplification

<400> SEQUENCE: 203
gcccgctaag gatcctctag ggaggtctag aatgaaagtc gcagtcctcg gc            52

<210> SEQ ID NO 204
<211> LENGTH: 33
<212> TYPE: DNA
<213> ORGANISM: Artificial Sequence
<220> FEATURE:
<223> OTHER INFORMATION: Primer for amplification

<400> SEQUENCE: 204
cgagcctcct tacttattaa cgaactcttc gcc                                 33

<210> SEQ ID NO 205
<211> LENGTH: 40
<212> TYPE: DNA
<213> ORGANISM: Artificial Sequence
<220> FEATURE:
<223> OTHER INFORMATION: Primer for amplification

<400> SEQUENCE: 205
catagggagg ctcgagatgt ataccgttgg ggattatctg                          40

<210> SEQ ID NO 206
<211> LENGTH: 47
<212> TYPE: DNA
<213> ORGANISM: Artificial Sequence
<220> FEATURE:
<223> OTHER INFORMATION: Primer for amplification

<400> SEQUENCE: 206
cgccaaaaca gaagcttgac gtcctagagg agcttgttaa caggctt                  47

<210> SEQ ID NO 207
<211> LENGTH: 1692
<212> TYPE: DNA
<213> ORGANISM: Saccharomyces cerevisiae

<400> SEQUENCE: 207
atgtctgaaa ttactttggg taaatatttg ttcgaaagat aaagcaagt caacgttaac     60 accgttttcg gtttgccagg tgacttcaac ttgtccttgt tggacaagat ctacgaagtt   120
gaaggtatga gatgggctgg taacgccaac gaattgaacg ctgcttacgc cgctgatggt   180
tacgctcgta tcaagggtat gtcttgtatc atcaccacct tcggtgtcgg tgaattgtct   240

```
gctttgaacg gtattgccgg ttcttacgct gaacacgtcg gtgttttgca cgttgttggt    300
gtcccatcca tctctgctca agctaagcaa ttgttgttgc accacacctt gggtaacggt    360
gacttcactg ttttccacag aatgtctgcc aacatttctg aaaccactgc tatgatcact    420
gacattgcta ccgccccagc tgaaattgac agatgtatca gaaccactta cgtcacccaa    480
agaccagtct acttaggttt gccagctaac ttggtcgact tgaacgtccc agctaagttg    540
ttgcaaactc caattgacat gtctttgaag ccaaacgatg ctgaatccga aaaggaagtc    600
attgacacca tcttggcttt ggtcaaggat gctaagaacc cagttatctt ggctgatgct    660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca agaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat gggtaactt cttgcaagaa   1140 ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc aaagaagag agttatctta   1320 ttcattggtg acggttcttt gcaattgact gttcaagaaa tctccaccat gatcagatgg   1380
ggcttgaagc catacttgtt cgtcttgaac aacgatggtt acaccattga aaagttgatt   1440
cacggtccaa aggctcaata caacgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga aatcatgttg   1620
ccagtcttcg atgctccaca aaacttggtt gaacaagcta agttgactgc tgctaccaac   1680
gctaagcaat aa                                                       1692
```

<210> SEQ ID NO 208
<211> LENGTH: 563
<212> TYPE: PRT
<213> ORGANISM: Saccharomyces cerevisiae

<400> SEQUENCE: 208

```
Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110
```

```
Leu His His Thr Leu Gly Asn Gly Asp Phe Thr Val Phe His Arg Met
        115                 120                 125
Ser Ala Asn Ile Ser Glu Thr Thr Ala Met Ile Thr Asp Ile Ala Thr
130                 135                 140
Ala Pro Ala Glu Ile Asp Arg Cys Ile Arg Thr Thr Tyr Val Thr Gln
145                 150                 155                 160
Arg Pro Val Tyr Leu Gly Leu Pro Ala Asn Leu Val Asp Leu Asn Val
                165                 170                 175
Pro Ala Lys Leu Leu Gln Thr Pro Ile Asp Met Ser Leu Lys Pro Asn
            180                 185                 190
Asp Ala Glu Ser Glu Lys Glu Val Ile Asp Thr Ile Leu Ala Leu Val
        195                 200                 205
Lys Asp Ala Lys Asn Pro Val Ile Leu Ala Asp Ala Cys Cys Ser Arg
210                 215                 220
His Asp Val Lys Ala Glu Thr Lys Lys Leu Ile Asp Leu Thr Gln Phe
225                 230                 235                 240
Pro Ala Phe Val Thr Pro Met Gly Lys Gly Ser Ile Asp Glu Gln His
                245                 250                 255
Pro Arg Tyr Gly Gly Val Tyr Val Gly Thr Leu Ser Lys Pro Glu Val
            260                 265                 270
Lys Glu Ala Val Glu Ser Ala Asp Leu Ile Leu Ser Val Gly Ala Leu
        275                 280                 285
Leu Ser Asp Phe Asn Thr Gly Ser Phe Ser Tyr Ser Tyr Lys Thr Lys
        290                 295                 300
Asn Ile Val Glu Phe His Ser Asp His Met Lys Ile Arg Asn Ala Thr
305                 310                 315                 320
Phe Pro Gly Val Gln Met Lys Phe Val Leu Gln Lys Leu Leu Thr Thr
                325                 330                 335
Ile Ala Asp Ala Ala Lys Gly Tyr Lys Pro Val Ala Val Pro Ala Arg
            340                 345                 350
Thr Pro Ala Asn Ala Ala Val Pro Ala Ser Thr Pro Leu Lys Gln Glu
        355                 360                 365
Trp Met Trp Asn Gln Leu Gly Asn Phe Leu Gln Glu Gly Asp Val Val
370                 375                 380
Ile Ala Glu Thr Gly Thr Ser Ala Phe Gly Ile Asn Gln Thr Thr Phe
385                 390                 395                 400
Pro Asn Asn Thr Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
            420                 425                 430
Asp Pro Lys Lys Arg Val Ile Leu Phe Ile Gly Asp Gly Ser Leu Gln
        435                 440                 445
Leu Thr Val Gln Glu Ile Ser Thr Met Ile Arg Trp Gly Leu Lys Pro
        450                 455                 460
Tyr Leu Phe Val Leu Asn Asn Asp Gly Tyr Thr Ile Glu Lys Leu Ile
465                 470                 475                 480
His Gly Pro Lys Ala Gln Tyr Asn Glu Ile Gln Gly Trp Asp His Leu
                485                 490                 495
Ser Leu Leu Pro Thr Phe Gly Ala Lys Asp Tyr Glu Thr His Arg Val
            500                 505                 510
Ala Thr Thr Gly Glu Trp Asp Lys Leu Thr Gln Asp Lys Ser Phe Asn
        515                 520                 525
Asp Asn Ser Lys Ile Arg Met Ile Glu Ile Met Leu Pro Val Phe Asp
```

```
                    530                 535                 540
Ala Pro Gln Asn Leu Val Glu Gln Ala Lys Leu Thr Ala Ala Thr Asn
545                 550                 555                 560

Ala Lys Gln
```